US012569491B2

(12) United States Patent
Howerton et al.

(10) Patent No.: US 12,569,491 B2
(45) **Date of Patent: *Mar. 10, 2026**

(54) METHODS FOR TREATING TESTICULAR AND OVARIAN ADRENAL REST TUMORS

(71) Applicant: Spruce Biosciences, Inc., South San Francisco, CA (US)

(72) Inventors: Alexis Howerton, San Francisco, CA (US); Hal Gerber, San Francisco, CA (US)

(73) Assignee: SPRUCE BIOSCIENCES, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/043,275

(22) Filed: Jan. 31, 2025

(65) Prior Publication Data

US 2025/0177404 A1 Jun. 5, 2025

Related U.S. Application Data

(63) Continuation of application No. 18/941,832, filed on Nov. 8, 2024, which is a continuation of application No. 17/667,285, filed on Feb. 8, 2022, now abandoned, which is a continuation of application No. 17/081,694, filed on Oct. 27, 2020, now Pat. No. 11,304,950, which is a continuation of application No. PCT/US2019/029486, filed on Apr. 26, 2019.

(60) Provisional application No. 62/822,815, filed on Mar. 23, 2019, provisional application No. 62/663,951, filed on Apr. 27, 2018.

(51) Int. Cl.

| | |
|---|---|
| ***A61K 31/519*** | (2006.01) |
| ***A61K 9/00*** | (2006.01) |
| ***A61K 9/20*** | (2006.01) |
| ***A61K 9/48*** | (2006.01) |
| ***A61P 5/06*** | (2006.01) |
| ***A61P 5/08*** | (2006.01) |
| *A61K 45/06* | (2006.01) |

(52) U.S. Cl.

CPC .......... *A61K 31/519* (2013.01); *A61K 9/0053* (2013.01); *A61K 9/20* (2013.01); *A61K 9/48* (2013.01); *A61K 45/06* (2013.01); *A61P 5/06* (2018.01); *A61P 5/08* (2018.01)

(58) Field of Classification Search

CPC .............. A61K 31/519; A61K 31/5377; A61K 9/0053; A61K 9/20; A61K 9/2004; A61K 9/48; A61K 9/4841; A61P 5/06; A61P 5/08; A61P 35/00

See application file for complete search history.

(56) References Cited

U.S. PATENT DOCUMENTS

| | | | |
|---|---|---|---|
| 4,328,245 | A | 5/1982 | Yu et al. |
| 4,409,239 | A | 10/1983 | Yu |
| 4,410,545 | A | 10/1983 | Yu et al. |
| 4,861,760 | A | 8/1989 | Mazuel et al. |
| 4,911,920 | A | 3/1990 | Jani et al. |
| 5,212,162 | A | 5/1993 | Missel et al. |
| 5,403,841 | A | 4/1995 | Lang et al. |
| 6,586,456 | B1 | 7/2003 | Fontaine et al. |
| 8,030,304 | B2 | 10/2011 | Chen et al. |
| 8,563,718 | B2 | 10/2013 | Rizzo et al. |
| 10,849,908 | B2 | 12/2020 | Howerton et al. |
| 11,007,201 | B2 | 5/2021 | Howerton et al. |
| 11,304,950 | B2 | 4/2022 | Howerton et al. |
| 11,311,549 | B2 | 4/2022 | Howerton et al. |
| 11,344,557 | B2 | 5/2022 | Howerton et al. |
| 11,351,177 | B2 | 6/2022 | Howerton et al. |
| 11,708,372 | B2 | 7/2023 | Reddy et al. |
| 11,858,932 | B2 | 1/2024 | Barnes et al. |
| 12,098,152 | B2 | 9/2024 | Barnes et al. |
| 12,115,166 | B2 | 10/2024 | Howerton et al. |
| 2002/0013357 | A1 | 1/2002 | Nadkarni et al. |
| 2003/0008885 | A1 | 1/2003 | He et al. |
| 2005/0209250 | A1 | 9/2005 | Romano |
| 2006/0078623 | A1 | 4/2006 | Dhoot et al. |
| 2009/0076266 | A1 | 3/2009 | Daugulis et al. |
| 2010/0022560 | A1 | 1/2010 | Chen et al. |
| 2010/0155595 | A1 | 6/2010 | Ghoshal et al. |
| 2010/0196389 | A1 | 8/2010 | Evans-Freke |
| 2010/0222339 | A1 | 9/2010 | Chen et al. |
| 2011/0136865 | A1 | 6/2011 | Buntinx |
| 2011/0160168 | A1 | 6/2011 | Dhingra |
| 2011/0166345 | A1 | 7/2011 | Rizzo et al. |
| 2013/0045979 | A1 | 2/2013 | Sanfilippo |
| 2017/0020877 | A1 | 1/2017 | Grigoriadis |
| 2017/0333126 | A1 | 11/2017 | Sobotka |
| 2018/0110554 | A1 | 4/2018 | Zarins et al. |

(Continued)

FOREIGN PATENT DOCUMENTS

| | | | |
|---|---|---|---|
| CN | 101516835 | A | 8/2009 |
| CN | 101516887 | A | 8/2009 |

(Continued)

OTHER PUBLICATIONS

Markopoulos et. al., J. Clin. Endocrinol. Metab., vol. 96(3), pp. 623-631, publ. 2011 (Year: 2011).*
El-Maouche et. al., Lancet, vol. 309, pp. 2194-2210, publ. 2017 (Year: 2017).*
Al-Muhammed, J. et al. In-vivo studies on dexamethasone sodium phosphate liposomes. Journal of microencapsulation 13(3):293-306 (1996).
Berge, Stephen M. et al. Pharmaceutical Salts. Journal of Pharmaceutical Sciences 66(1):1-19 (1977).

(Continued)

*Primary Examiner* — Sarah Pihonak
(74) *Attorney, Agent, or Firm* — WILSON SONSINI GOODRICH & ROSATI

(57) ABSTRACT

Provided herein are compounds and pharmaceutical compositions for the prevention and treatment of testicular adrenal rest tumors (TART) or ovarian adrenal rest tumors (OART).

19 Claims, 14 Drawing Sheets

(56) References Cited

U.S. PATENT DOCUMENTS

| | | | |
|---|---|---|---|
| 2019/0262349 | A1 | 8/2019 | Howerton et al. |
| 2020/0255436 | A1 | 8/2020 | Howerton et al. |
| 2021/0015827 | A1 | 1/2021 | Howerton et al. |
| 2021/0038604 | A1 | 2/2021 | Howerton et al. |
| 2021/0137935 | A1 | 5/2021 | Howerton et al. |
| 2021/0322430 | A1 | 10/2021 | Howerton et al. |
| 2021/0361664 | A1 | 11/2021 | Howerton et al. |
| 2022/0133742 | A1 | 5/2022 | Ghosh et al. |
| 2022/0143037 | A1 | 5/2022 | Howerton et al. |
| 2022/0211711 | A1 | 7/2022 | Howerton et al. |
| 2023/0159533 | A1 | 5/2023 | Reddy et al. |
| 2023/0321112 | A1 | 10/2023 | Howerton et al. |
| 2023/0414627 | A1 | 12/2023 | Howerton et al. |
| 2024/0043432 | A1 | 2/2024 | Reddy et al. |
| 2024/0261300 | A1 | 8/2024 | Ghosh et al. |
| 2024/0293421 | A1 | 9/2024 | Reddy et al. |
| 2025/0064812 | A1 | 2/2025 | Howerton et al. |
| 2025/0177403 | A1 | 6/2025 | Howerton et al. |
| 2025/0195527 | A1 | 6/2025 | Howerton et al. |

FOREIGN PATENT DOCUMENTS

| | | | |
|---|---|---|---|
| CN | 106102740 | A | 11/2016 |
| EP | 2094709 | B1 | 9/2010 |
| EP | 3984523 | A1 | 4/2022 |
| EP | 3784233 | B1 | 6/2024 |
| JP | H0971528 | A | 3/1997 |
| JP | 2000302693 | A | 10/2000 |
| JP | 2010504344 | A | 2/2010 |
| JP | 2017503030 | A | 1/2017 |
| WO | WO-9413676 | A1 | 6/1994 |
| WO | WO-9722596 | A1 | 6/1997 |
| WO | WO-9729109 | A1 | 8/1997 |
| WO | WO-9730035 | A1 | 8/1997 |
| WO | WO-9732856 | A1 | 9/1997 |
| WO | WO-9803510 | A1 | 1/1998 |
| WO | WO-9808847 | A1 | 3/1998 |
| WO | WO-9813354 | A1 | 4/1998 |
| WO | WO-9902166 | A1 | 1/1999 |
| WO | WO-0040529 | A1 | 7/2000 |
| WO | WO-0041669 | A2 | 7/2000 |
| WO | WO-0059908 | A2 | 10/2000 |
| WO | WO-0123388 | A2 | 4/2001 |
| WO | WO-0192224 | A1 | 12/2001 |
| WO | WO-0204434 | A1 | 1/2002 |
| WO | WO-0208213 | A1 | 1/2002 |
| WO | WO-02072202 | A1 | 9/2002 |
| WO | WO-2005020910 | A2 | 3/2005 |
| WO | WO-2005063755 | A1 | 7/2005 |
| WO | WO-2005079868 | A2 | 9/2005 |
| WO | WO-2006102194 | A1 | 9/2006 |
| WO | WO-2007109853 | A1 | 10/2007 |
| WO | WO-2008036579 | A1 | 3/2008 |
| WO | WO-2010039678 | A1 | 4/2010 |
| WO | WO-2013160317 | A2 | 10/2013 |
| WO | WO-2015112642 | A1 | 7/2015 |
| WO | WO-2019036472 | A1 | 2/2019 |
| WO | WO-2019036503 | A1 | 2/2019 |
| WO | WO-2019210266 | A1 | 10/2019 |
| WO | WO-2020115555 | A2 | 6/2020 |
| WO | WO-2021016208 | A1 | 1/2021 |
| WO | WO-2022036123 | A1 | 2/2022 |
| WO | WO-2023091684 | A1 | 5/2023 |

OTHER PUBLICATIONS

Chen, Hua-dong et al. Ovarian adrenal rest tumors undetected by imaging studies and identified at surgery in three females with congenital adrenal hyperplasia unresponsive to increased hormone therapy dosage. Endocrine pathology 28(2):146-151 (2017).

Chonn, Archadio et al. Recent Advances in Liposomal Drug-delivery Systems. Current Opinion in Biotechnology 6(6):698-708 (1995).

Co-pending U.S. Appl. No. 18/941,832, inventors Howerton; Alexis et al., filed Nov. 8, 2024.

Co-pending U.S. Appl. No. 19/043,264, inventors Howerton; Alexis et al., filed Jan. 31, 2025.

Co-pending U.S. Appl. No. 19/043,303, inventors Howerton; Alexis et al., filed Jan. 31, 2025.

Eyles et al. Oral delivery and fate of poly(lactic acid) microsphere-encapsulated interferon in rats. J Pharm Pharmacol. 49(7):669-74 (1997).

Gao, Zhi-Hui et al. Controlled Release of a Contraceptive Steroid From Biodegradable and Injectable Gel Formulations: in Vitro Evaluation. Pharmaceutical research 12(6):857-863 (1995).

Jin et al. Testicular adrenal rest tumors in a patient with untreated congenital adrenal hyperplasia. Korean J Pediatr 2011;54(3):137-140.

Kaprara, et al. The corticotropin releasing factor system in cancer: expression and pathophysiological implications. Cellular and molecular life sciences 67(8):1293-1306 (2010).

Mendes-Dos-Santos et al. Prevalence of Testicular Adrenal Rest Tumor and Factors Associated with Its Development in Congenital Adrenal Hyperplasia. Hormone Res. In Paed. 90:161-168 (2018).

Munson, Peter et al. Ligand: a Versatile Computerized Approach for Characterization of Ligand-binding Systems. Analytical Biochemistry 107(1):220-239 (1980).

*Neurocrine Biosciences, Inc.* (Petitioner) v. *Spruce Biosciences, Inc.* (Patent Owner). Decision Granting Institution of Post-Grant Review of U.S. Pat. No. 11,007,201 dated Dec. 1, 2023 (pp. 1-38) (PGR2022-00025).

*Neurocrine Biosciences, Inc.* (Petitioner) v. *Spruce Biosciences, Inc.* (Patent Owner). Final Written Decision of Post-Grant Review of U.S. Pat. No. 10,849,908 dated Nov. 26, 2024 (pp. 1-62) (PGR2021-00088).

*Neurocrine Biosciences, Inc.* (Petitioner) v. *Spruce Biosciences, Inc.* (Patent Owner). Final Written Decision of Post-Grant Review of U.S. Pat. No. 11,007,201 dated Nov. 27, 2024 (pp. 1-60) (PGR2022-00025).

*Neurocrine Biosciences, Inc.* (Petitioner) v. *Spruce Biosciences, Inc.* (Patent Owner). Petition for Post Grant Review of U.S. Pat. No. 10,849,908 dated May 28, 2021 (pp. 1-90) (PGR2021-00088).

*Neurocrine Biosciences, Inc.* (Petitioner) v. *Spruce Biosciences, Inc.* (Patent Owner). Petition for Post Grant Review of U.S. Pat. No. 11,007,201 dated Feb. 18, 2022 (pp. 1-92) (PGR2022-00025).

Ostro, Mark J. et al. Use of Liposomes as Injectable-drug Delivery Systems. American Journal of Hospital Pharmacy 46(8):1576-1587 (1989).

PCT/US2019/029486 International Invitation to Pay Additional Fees dated Jun. 4, 2019.

PCT/US2019/029486 International Search Report and Written Opinion dated Aug. 12, 2019.

Rao. Recent developments of collagen-based materials for medical applications and drug delivery systems. J Biomater Sci Polym Ed. 7(7):623-45 (1995).

Reichman et al. Fertility in Patients with Congenital Adrenal Hyperplasia. Fertility and Sterility, vol. 101, No. 2, 2014. 301-309.

Reisch et al. Testicular adrenal rest tumors develop independently of long-term disease control: a longitudinal analysis of 50 adult men with congenital adrenal hyperplasia due to classic 21-hydroxylase deficiency. J. Clin. Endocrinol. Metab. 98(11):E1820-E1826 (2013).

Smeets et al. Molecular characterization of testicular adrenal rest tumors in congenital adrenal hyperplasia: lesions with both adrenocortical and Leydig cell features. JCEM 100(3):E524-E530 (2015).

Tiosano et al. Ovarian adrenal rest tumor in a congenital adrenal hyperplasia patient with adrenocorticotropin hypersecretion following adrenalectomy. Hormone Res. in Paediatrics 74:223-228 (2010).

U.S. Appl. No. 17/081,694 Office Action dated Feb. 26, 2021.

U.S. Appl. No. 17/081,694 Office Action dated Jun. 11, 2021.

U.S. Appl. No. 17/667,285 Office Action dated Dec. 29, 2023.

U.S. Appl. No. 17/667,285 Office Action dated Jun. 10, 2024.

Zaarour et al. Bilateral Ovary Adrenal Rest Tumor in a Congenital Adrenal Hyperplasia Following Adrenalectomy. Endocrinol. Pract. 20(4):e69-e74 (2014).

Abcam CP 154526 Hydrochloride, Non-Peptide CRF1 Receptor Antagonist AB141429. [Internet] ABCAM. Retrieved from URL:

(56) References Cited

OTHER PUBLICATIONS https://www.abcam.com/products/biochemicals/cp-154526-hydrochloride-non-peptide-crf1-receptor-antagonist-ab141429.html. 2 pages.
Auchus, Richard J. et al. Phase 3 trial of crinecerfont in adult congenital adrenal hyperplasia. New England Journal of Medicine 391(6):504-514 (2024).
Auchus, Richard J. et al. Supplemental Information: Phase 3 trial of crinecerfont in adult congenital adrenal hyperplasia. New England Journal of Medicine 391(6):504-514 (2024).
Auchus, Richard J. Management Considerations for the Adult With Congenital Adrenal Hyperplasia. Molecular and Cellular Endocrinology 408:190-197 (2015).
Avila, N. A. et al. Testicular adrenal rest tissue in congenital adrenal hyperplasia: serial sonographic and clinical findings. AJR. American journal of roentgenology 172(5):1235-1238 (1999).
Aycan, Zehra et al. Prevalence and long-term follow-up outcomes of testicular adrenal rest tumours in children and adolescent males with congenital adrenal hyperplasia. Clinical endocrinology 78(5):667-672 (2013).
Bornstein et al. Diagnosis and Treatment of Primary Adrenal Insufficiency: An Endocrine Society Clinical Practice Guideline. J Clin Endocrinol Metab 101(2):364-389 (2016).
Chen, C., Recent Advances in Small Molecule Antagonists of the Corticotropin-Releasing Factor Type-1 Receptor-Focus on Pharmacology and Pharmacokinetics. Current Medicinal Chemistry 13:1261-1282 (2006).
Chen et al. Design of 2,5-Dimethyl-3-(6-dimethyl-4-methylpyridin-3-yl)-7-dipropyl aminopryazolo[1,5-a]pyrimidine (NBI 30775/R121919) and Structure-Activity Relationships of a Series of Potent and Orally Active Corticotropin-Releasing Factor Receptor Antagonists. J Med Chem 47(19):4787-4798 (2004).
Claahsen-Van Der Grinten, H. L. et al. Testicular adrenal rest tumours in congenital adrenal hyperplasia. International Journal of pediatric endocrinology 2009:624823, 1-8 (2009).
Claahsen-Van Der Grinten, Hedi L. et al. Prevalence of testicular adrenal rest tumours in male children with congenital adrenal hyperplasia due to 21-hydroxylase deficiency. European journal of endocrinology 157(3):339-344 (2007).
Claahsen-Van Der Grinten, Hedi L. et al. Repeated successful induction of fertility after replacing hydrocortisone with dexamethasone in a patient with congenital adrenal hyperplasia and testicular adrenal rest tumors. Fertility and Sterility 88(3):705.e5-705.e8 (2007).
ClinicalTrials.gov Identifier: NCT04457336. A Ph2b to Evaluate Clinical Efficacy and Safety of Tildacerfont in Adult CAH, Record created Jun. 25, 2020. pp. 1-17. [retrieved on Aug. 12, 2025] Available at URL: https://clinicaltrials.gov/study/NCT04457336.
Dave. Overview of pharmaceutical excipients used in tablets and capsules. https://www.drugtopics.com/view/overview-pharmaceutical-excipients-used-tablets-and-capsules (Oct. 24, 2008) 52 pages.
Delfino, Michele et al. Testicular adrenal rest tumors in patients with congenital adrenal hyperplasia: prevalence and sonographic, hormonal, and seminal characteristics. Journal of ultrasound in medicine 31(3):383-388 (2012).
Do, Hien-Quang et al. A General Method for Copper-Catalyzed Arylation of Arene C—H Bonds. J Am Chem Soc. 130(45):15185-15192 (2008).
Do, Hien-Quang et al. Copper-Catalyzed Arylation and Alkenylation of Polyfluoroarene C—H Bonds. Journal of American Chemical Society 130(4):1128-1129 (2008).
Do, Hien-Quang et al. Copper-catalyzed arylation of C—H bonds; Abstracts of Papers, 236th ACS National Meeting, New Orleans, LA, Apr. 6-10, 2008, Accession No. 2008:390596.
Do, Hien-Quang et al. Copper-Catalyzed Arylation of Heterocycle C—H Bonds. J Am Chem Soc. 129(41):12404-12405 (2007).
Engels, Manon et al. Testicular adrenal rest tumors: current insights on prevalence, characteristics, origin, and treatment. Endocrine Reviews 40(4):973-987 (2019).
EP19793181.9 Brief Communication—Opposition Proceedings dated Aug. 5, 2025.
EP19793181.9 Reply from the opponent to submission of proprietor dated Jul. 18, 2025.
EP19793181.9 Reply of the Patent Proprietor to the notice(s) of opposition dated Jun. 18, 2025.
EP19793181.9 Letter from the Opponent—Opposition Proceedings dated Mar. 6, 2025.
Escobar-Morreale, HF., Polycystic ovary syndrome: definition, aetiology, diagnosis and treatment. Nat Rev Endocrinol. 14(5):270-284 (2018).
Fahmy, Hesham et al. Structure and Function of Small Non-Peptide CRF Antagonists and their Potential Clinical Use. Current Molecular Pharmacology 10(4):270-281 (2017).
Fleck, Beth A. et al. Binding Kinetics Redefine the Antagonist Pharmacology of the Corticotropin-releasing Factor Type 1 Receptor. The Journal of Pharmacology and Experimental Therapeutics 341(2):518-531 (2012).
Fuqua et al. Duration of suppression of adrenal steroids after glucocorticoid administration. Int J Pediatr Endocrinol 2010:712549 (2010).
Gehlert, Donald R. et al. 3-(4-Chloro-2-morpholin-4-yl-thiazol-5-yl)-8-(1-ethylpropyl)-2,6-dimethyl-imidazo[1,2-b]pyridazine: a novel brain-penetrant, orally available corticotropin-releasing factor receptor 1 antagonist with efficacy in animal models of alcoholism. The Journal of neuroscience 27(10):2718-2726 (2007).
Gilligan P. et al., The Discovery of 4-(3-Pentylamino)-2,7-dimethyl-8-(2-methyl-4-methoxyphenyl)-pyrazolo-[1,5-alpha]-pyrimidine: A corticotrophin-Releasing Factor (hCRF1)Antagonist. Bioorganic & Medicinal Chemistry 8(1):181-189 (2000).
He, Liqi et al. 4-(1,3-Dimethoxyprop-2-ylamino)-2,7-dimethyl-8-(2,4-dichlorophenyl)pyrazolo[1,5-a]-1,3,5-triazine: A Potent, Orally Bioavailable CRF1 Receptor Antagonist. J Med Chem 43:449-456 (2000).
Hodgetts et al. Discovery of N-(1-ethylpropyl)-[3-methoxy-5-(2-methoxy-4-trifluoromethoxyphenyl)-6-methyl-pyrazin-2-yl]amine 59 (NGD 98-2): an orally active corticotropin releasing factor-1 (CRF-1) receptor antagonist. J Med Chem 54:4187-4206 (2011).
Joseph, Dana N., and Shannon Whirledge. Stress and the HPA axis: balancing homeostasis and fertility. International journal of molecular sciences 18(10):2224, 1-15 (2017).
Khadilkar et al., Can polycystic ovarian syndrome be cured? Unfolding the concept of secondary polycystic ovarian syndrome. J Obstet Gynaecol India 69(4):297-302 (2019).
Lee et al. Attenuated Forms of Congenital Adrenal Hyperplasia due to 21-Hydroxylase Deficiency. J Clin Endocrinol Metab. 55(5):866-871 (1982).
Ma, Li et al. Sonographic features of the testicular adrenal rests tumors in patients with congenital adrenal hyperplasia: a single-center experience and literature review. Orphanet Journal of Rare Diseases 14(1):242, 1-8 (2019).
Majo et al. Facile Palladium-Catalyzed Synthesis of 3-Arylpyrazolo-[1,5-a]pyrimidines. Adv. Synth. Catal. 345(5):620-624 (2003).
Malvern Instruments Worldwide. A Basic Guide to Particle Characterization. Inform—White Paper (pp. 1-26) (2012).
Mazzilli, Rossella et al. The High Prevalence of Testicular Adrenal Rest Tumors in Adult Men With Congenital Adrenal Hyperplasia Is Correlated With ACTH Levels. Front Endocrinol (Lausanne) 10:335 (2019).
Million, Mulugeta et al., A Novel Water-Soluble Selective CRF1 Receptor Antagonist, NBI 35965, Blunts Stress-Induced Visceral Hyperalgesia and Colonic Motor Function in Rats. Brain Research, 985(1):32-42 (2003).
Morabbi, Mohammad-Javad et al., Pexacerfont as a CRF1 Antagonist for the Treatment of Withdrawal Symptoms in Men With Heroin/Methamphetamine Dependence: A Randomized, Double-Blind, Placebo-Controlled Clinical Trial. International Clinical Psychopharmacology 1-9 (2017).
Nella et al. A Phase 2 Study of Continuous Subcutaneous Hydrocortisone Infusion in Adults With Congenital Adrenal Hyperplasia. J Clin Endocrinol Metab. 101(12):4690-4698 (2016).

(56) References Cited

OTHER PUBLICATIONS

*Neurocrine Biosciences, Inc.* (Claimant) v. *Spruce Biosciences, Inc.* (Defendant). Defence dated Mar. 13, 2025 (Claim No. HP-2025-000005) (pp. 1-3).
*Neurocrine Biosciences, Inc.* (Claimant) v. *Spruce Biosciences, Inc.* (Defendant). Grounds of Invalidity dated Jan. 31, 2025 (Claim No. HP-2025-000005) (pp. 1-10).
*Neurocrine Biosciences, Inc.* (Claimant) v. *Spruce Biosciences, Inc.* (Defendant). Particulars of Claim dated Jan. 31, 2025 (Claim No. HP-2025-000005) (pp. 1-10).
*Neurocrine Biosciences, Inc.* (Petitioner) v. *Spruce Biosciences, Inc.* (Patent Owner). Decision Granting Institution of Post-Grant Review of U.S. Pat. No. 10,849,908 dated Dec. 1, 2023 (pp. 1-57) (PGR2021-00088).
*Neurocrine Biosciences, Inc.* (Petitioner) v. *Spruce Biosciences, Inc.* (Patent Owner). Patent Owner's Response in U.S. Pat. No. 12,115,166 dated Jul. 8, 2025 (pp. 1-6) (PGR-2025-00032).
*Neurocrine Biosciences, Inc.* (Petitioner) v. *Spruce Biosciences, Inc.* (Patent Owner). Petition for Post Grant Review of U.S. Pat. No. 12,115,166 dated Feb. 10, 2025 (pp. 1-59).
*Neurocrine Biosciences, Inc.* (Petitioner) v. *Spruce Biosciences, Inc.* (Patent Owner). Petitioner's Reply to Patent Owner's Response in U.S. Pat. No. 10,849,908 dated Jun. 20, 2024 (pp. 1-38) (PGR2021-00088).
*Neurocrine Biosciences, Inc.* (Petitioner) v. *Spruce Biosciences, Inc.* (Patent Owner). Petitioner's Reply to Patent Owner's Response in U.S. Pat. No. 11,007,201 dated Jun. 20, 2024 (pp. 1-36) (PGR2022-00025).
*Neurocrine Biosciences, Inc.* (Plaintiff) v. *Spruce Biosciences, Inc.* (Defendant). Memorandum dated Jun. 9, 2025 (Case No. 1:25-cv-00059-JDW (pp. 1-10).
Nissen, Trygve et al. The clinical case report: a review of its merits and limitations. BMC Research Notes 7:264, 1-7 (2014).
O'Reilly, Michael W. et al. 11-oxygenated C19 steroids are the predominant androgens in polycystic ovary syndrome. J Clin Endocrinol Metab. 102(3):840-848 (2017).
PCT/US2007/078605 International Search Report and Written Opinion dated Jan. 31, 2008.
PCT/US2009/058722 International Search Report and Written opinion dated Jan. 25, 2010.
PCT/US2018/046707 International Search Report and Written Opinion dated Oct. 24, 2018.
PCT/US2018/046760 International Search Report and Written Opinion dated Oct. 24, 2018.
PCT/US2020/042820 International Search Report and Written Opinion dated Nov. 25, 2020.
PCT/US2021/045780 International Search Report and Written Opinion dated Dec. 17, 2021.
PCT/US2022/050436 International Search Report and Written Opinion dated Nov. 18, 2022.
Reisch, Nicole et al. High prevalence of reduced fecundity in men with congenital adrenal hyperplasia. The Journal of Clinical Endocrinology and Metabolism 94(5):1665-1670 (2009).
Rosenfield et al., The pathogenesis of polycystic ovary syndrome (PCOS): the hypothesis of PCOS as functional ovarian hyperandrogenism revisited. Endocrine Reviews 37(5):467-520 (2016).
Sarafoglou et al. SUN-LB064 A Phase 2, Dose-Escalation, Safety and Efficacy Study of Tildacerfont (SPR001) for the Treatment of Patients with Classic Congenital Adrenal Hyperplasia. Journal of the Endocrine Society 3(Supplement_1):SUN-LB064 (2017).
Sarafoglou, Kyriakie et al. Tildacerfont in Adults With Classic Congenital Adrenal Hyperplasia: Results from Two Phase 2 Studies. The Journal of Clinical Endocrinology and Metabolism 106(11):e4666-e4679 (2021).
Speiser, Phyllis W. et al. Congenital Adrenal Hyperplasia Due to Steroid 21-hydroxylase Deficiency: An Endocrine Society Clinical Practice Guideline. The Journal of Clinical Endocrinology and Metabolism 95(9):4133-4160 (2010).
Spruce Biosciences announces topline results from CAHMELIA-203 in adult classic CAH and CAHPTAIN-205 in pediatric classic CAH. Spruce Biosciences :1-7 (2024).
Spruce Biosciences announces topline results from CAHMELIA-204 in adult CAH and CAHPTAIN-205 in adult and pediatric CAH. Spruce Biosciences :1-4 (2024).
Spruce Biosciences, Inc. Study of SPR001 in Adults with Classic Congenital Adrenal Hyperplasia. 2017. pp. 1-7.
Spruce Biosciences, Inc. Study to Evaluate the Safety and Efficacy of SPR001 in Subjects with Classic Congenital Adrenal Hyperplasia. 2018. pp. 1-7.
Stikkelbroeck, Nike M. M. L. et al. High prevalence of testicular adrenal rest tumors, impaired spermatogenesis, and Leydig cell failure in adolescent and adult males with congenital adrenal hyperplasia. The Journal of Clinical Endocrinology and Metabolism 86(12):5721-5728 (2001).
Stikkelbroeck, Nike M. M. L. et al. Monitoring of menstrual cycles, ovulation, and adrenal suppression by saliva sampling in female patients with 21-hydroxylase deficiency. Fertility & sterility 80(4):1030-1036 (2003).
Thakral, Naveen K. et al. Salt Disproportionation in the Solid State: Role of Solubility and Counterion Volatility. Molecular pharmaceutics 13(12):4141-4151 (2016).
The Journal of Clinical Endocrinology and Metabolism Author Guidelines. Oxford Academic (2025); [retrieved on Jun. 9, 2025]. Available at URL: https://academic.oup.com/jcem/pages/author_guidelines.
Trapp et al. Congenital adrenal hyperplasia: an update in children. Curr Opin Endocrinol Diabetes Obes. 18(3):166-70 (2011).
Turcu, Adina F. and Richard J. Auchus. Adrenal steroidogenesis and congenital adrenal hyperplasia. Endocrinology and Metabolism Clinics 44(2):275-296 (2015).
Turcu, Adina F., and Richard J. Auchus. Novel treatment strategies in congenital adrenal hyperplasia. Current Opinion in Endocrinology, Diabetes and Obesity 23(3):225-232 (2016).
Turcu, Adina F. et al. Single-dose study of a corticotropin-releasing factor receptor-1 antagonist in women with 21-hydroxylase deficiency. The Journal of Clinical Endocrinology and Metabolism 101(3):1174-1180 (2016).
Turcu, Adina F. et al. Supplemental Information: Single-dose study of a corticotropin-releasing factor receptor-1 antagonist in women with 21-hydroxylase deficiency. The Journal of Clinical Endocrinology and Metabolism 101(3):1174-1180 (2016).
U.S. Appl. No. 62/822,815, filed Mar. 23, 2019.
U.S. Appl. No. 17/586,228 Office Action dated Jun. 10, 2022.
U.S. Appl. No. 13/063,226 Office Action dated Jan. 24, 2013.
U.S. Appl. No. 16/388,620 Office Action dated Jul. 15, 2019.
U.S. Appl. No. 16/388,620 Office Action dated Nov. 25, 2019.
U.S. Appl. No. 16/639,540 Office Action dated Jul. 11, 2022.
U.S. Appl. No. 16/639,540 Office Action dated Mar. 28, 2024.
U.S. Appl. No. 16/639,540 Office Action dated May 25, 2023.
U.S. Appl. No. 16/639,540 Office Action dated Nov. 16, 2021.
U.S. Appl. No. 16/639,540 Office Action dated Sep. 28, 2023.
U.S. Appl. No. 16/639,541 Office Action dated Apr. 4, 2022.
U.S. Appl. No. 17/063,592 Office Action dated Dec. 7, 2021.
U.S. Appl. No. 17/078,054 Office Action dated Dec. 14, 2020.
U.S. Appl. No. 17/359,411 Office Action dated Jan. 6, 2022.
U.S. Appl. No. 17/359,414 Office Action dated Nov. 16, 2021.
U.S. Appl. No. 17/586,228 Office Action dated Mar. 30, 2022.
U.S. Appl. No. 17/720,074 Office Action dated Aug. 26, 2022.
U.S. Appl. No. 18/078,649 Office Action dated Mar. 21, 2024.
U.S. Appl. No. 18/078,649 Office Action dated Oct. 9, 2024.
U.S. Appl. No. 18/078,649 Office Action dated Sep. 8, 2023.
U.S. Appl. No. 18/307,718 Office Action dated Oct. 12, 2023.
U.S. Appl. No. 18/310,463 Office Action dated Oct. 31, 2024.
U.S. Appl. No. 19/043,264 Office Action dated Apr. 25, 2025.
Varma. Excipients used in the Formulation of Tablets. https://www.rroij.com/openaccess/excipients-used-in-the-formulationof-tablets-.php?aid=78260 Revised date: Jul. 26, 2016.
Waldron, James. Spruce saws off only drug after 2nd hyperplasia fail, leaving biotech's direction in doubt. Fierce Biotech :1-2 (2024).

(56) References Cited

OTHER PUBLICATIONS

Wang, Zhu et al. Diagnosis of testicular adrenal rest tumors on ultrasound: a retrospective study of 15 cases report. Medicine 94(36):e1471, 1-6 (2015).
Williams, John P. Corticotropin-releasing factor 1 receptor antagonists: a patent review. Expert Opin Ther Pat 23(8):1057-68 (2013).
World Health Organization Drug Information, 32(2):369-370 (2018).
Yamada, Yasuki et al. New class of corticotropin-releasing factor (CRF) antagonists: small peptides having high binding affinity for CRF receptor. Journal of medicinal chemistry 47(5):1075-1078 (2004).
Yasir, Muhammad et al. Corticosteroid Adverse Effects. StatPearls, Jul. 3, 2023; [retrieved on Jun. 17, 2025]. Available at URL: https://www.ncbi.nlm.nih.gov/books/NBK531462/ pp. 1-14.
Yu, Min Kyung et al. Clinical manifestations of testicular adrenal rest tumor in males with congenital adrenal hyperplasia. Annals of pediatric endocrinology and metabolism 20(3):155-161 (2015).
Zhang et al. D-Level Essay in Statistics, 2009, How to Analyze Change from Baseline. Available at http://www.statistics.du.se/essays/D09 Zhang%20Ling%20&%20Han%20Kun.pdf (Jun. 10, 2009).
Zorrilla, Eric P. et al., Progress in Corticotropin-Releasing Factor-1 Antagonist Development. Drug Discov Today 15(9-10):371-383 (2010).
Zorrilla, Eric P. et al. The therapeutic potential of CRF1 antagonists for anxiety. Expert opinion on investigational drugs 13(7):799-828 (2004).
Bradley, D. Anawalt et al. Chapter 12: Testes. Greenspan's Basic & Clinical Endocrinology. 10th ed. New York: McGraw-Hill Education (pp. 413-442) (2018).
EP3784233 Case Details for ACT_34386/2025 (1 pg) (2025).
FDA Approves New Treatment for Congenital Adrenal Hyperplasia, US Food and Drug Administration, Dec. 13, 2024. Available at URL: https://www.fda.gov/news-events/press-announcements/fda-approves-new-treatment-congenital-adrenal-hyperplasia? pp. 1-2.
Speiser, Phyllis W. et al. Congenital adrenal hyperplasia due to steroid 21-hydroxylase deficiency: an endocrine society clinical practice guideline. The Journal of Clinical Endocrinology and Metabolism 103(11):4043-4088 (2018).
Spruce Power Holding Corporation. Quarterly Report (Form 10-Q) for the period ended Jun. 30, 2024. United States Securities and Exchange Commission, Aug. 13, 2024. Available at: https://www.sec.gov/Archives/edgar/data/1772720/000162828024037238/spru-20240630.htm pp. 1-53.
U.S. Appl. No. 19/043,264 Office Action dated Aug. 18, 2025.
U.S. Appl. No. 19/043,303 Office Action dated Sep. 5, 2025.
World Health Organization. Drug Information 33(1):122 (2019).
Čakir et al., Testicular Adrenal Rest Tumors in Patients with Congenital Adrenal Hyperplasia. J Clin Res Pediatr Endocrinol 4(2):94-100 (2012).
Anawalt, Bradley D. et al. Chapter 12: Testes. Extract from Textbook: Gardner & Shoback, Greenspan's Basic & Clinical Endocrinology, 10th ed. (McGraw-Hill Education), pp. 413, 440-441 (2018).
Bacon et al., Effect of Cortisol Treatment on Hormonal Relationships in Congenital Adrenal Hyperplasia. Clinical Endocrinology 6:113-126 (1977).
Benvenga et al., Testicular adrenal rests: evidence for luteinizing hormone receptors and for distinct types of testicular nodules differing for their autonomization. European Journal of Endocrinology 141:231-237 (1999).
Bhatt, Deepak L. et al. A Controlled Trial of Renal Denervation for Resistant Hypertension. N Engl J Med 370(15):1393-401 (2014).
Brown, Marie T. et al. Medication Adherence: WHO Cares? Mayo Clin Proc 86(4):304-314 (2011).
Chemical Abstracts Service. CAS Registry: 752253-39-7. 4-(2-Chloro-4-methoxy-5-methylphenyl)-N-((1S)-2-cyclopropyl-1-(3-fluoro-4-methylphenyl)ethyl)-5-methyl-N-2-propyn-1-yl-2-thiazolamine: pp. 1-35. STN Entry Date Oct. 11, 2005. Retrieved Oct. 14, 2025. Retrieved from :https://pubchem.ncbi.nlm.nih.gov/compound/5282340.
Claahsen et al., Testicular Tumors in Patients with Congenital Adrenal Hyperplasia due to 21-Hydroxylase Deficiency Show Functional Features of Adrenocortical Tissue. J Clin Endocrinol Metab. 92(9):3674-80 (2007).
Clinical Study Protocol SPR001-201. A Phase 2, Multiple-Dose, Dose-Escalation Study to Evaluate the Safety and Efficacy of SPR001 in Adults with Classic Congenital Adrenal Hyperplasia (CAH). (Aug. 23, 2018).
Declaration of Associate Professor Dr Henrik Falhammar dated Nov. 14, 2025.
Declaration of Professor Peter Hindmarsh dated Oct. 23, 2025.
Declaration of Vivian H. Lin, M.D. dated Nov. 14, 2025.
Fedorova, Olga et al. What is the need for adrenalectomy in patients with congenital adrenal hyperplasia in the era of CRF1/ACT inhibitors? Frontiers in Endocrinology (Lausanne) 16:1693063, 1-10 (2025).
Gupta et al., Corticosteroid Physiology and Principles of Therapy. Indian J Pediatr 75(10):1039-1044 (2008).
Gwathmey et al., Glucocorticoid-Induced Fetal Programming Alters the Functional Complement of Angiotensin Receptor Subtypes Within the Kidney. Hypertension 57(3):620-6 (2011).
Henrik Falhammar, M.D., Ph.D., FRACP, Curriculum Vitae (No date available).
Hindmarsh et al., Congenital Adrenal Hyperplasia A Comprehensive Guide. Elsevier, ISBN: 978-0-12-811483-4 (pp. 263-264 and 319-320) (2017).
Matsubara. Pathophysiological Role of Angiotensin II Type 2 Receptor in Cardiovascular and Renal Diseases. Circ Res. 83:1182-1191 (1998).
Meena, H. et al., Growth Pattern and Clinical Profile of Indian Children with Classical 21-Hydroxylase Deficiency Congenital Adrenal Hyperplasia on Treatment. Indian J Pediatr. 86(6):496-502 (2019).
Mesa et al., Immunophenotypic differences between neoplastic and non-neoplastic androgen-producing cells containing and lacking Reinke crystals. Virchows Arch. 469(6):679-686 (2016).
Morris, David. Steroid-induced Diabetes and Hyperglycaemia. Part 1: Mechanisms and Risks. Diabetes & Primary Care 20(4):151-153 (2018).
Nagurney et al., The Accuracy and completeness of Data Collected by Prospective and Retrospective Methods. Acad Emerg Med 12(9):884-95 (Sep. 2005).
*Neurocrine Biosciences, Inc.* (Petitioner) v. *Spruce Biosciences, Inc.* (Patent Owner). Decision Denying Institution of Inter Partes Review in U.S. Pat. No. 12,115,166 dated Oct. 3, 2025 (pp. 1-3) (PGR-2025-00032).
Newfield, Ron S. et al. Crinecerfont, a CRF1 Receptor Antagonist, Lowers Adrenal Androgens in Adolescents with Congenital Adrenal Hyperplasia. The Journal of Clinical Endocrinology & Metabolism 108(11):2871-2878 (2023).
Poyrazoglu et al., Prevalence of testicular microlithiasis in males with congenital adrenal hyperplasia and its association with testicular adrenal rest tumors. Horm Res Paediatr. 73:443-448 (2010).
Regulation (EC) No. 141/2000 of the European Parliament and of the Council of Dec. 16, 1999 on orphan medical products (pp. 1-5).
Sowers et al., Effect of dexamethasone on gonadotropin responsiveness to luteinizing hormone-releasing hormone and clomiphene in women with secondary amenorrhea. Am J Obstet Gynecol. 134(3):325-8 (Jun. 1, 1979).
Spierling, Samantha R, and Eric P Zorrilla et al. Don't stress about CRF: Assessing the translational failures of CRF1 antagonists. Psychopharmacology 234(9-10):1467-1481 (2017).
U.S. Appl. No. 17/578,149 Office Action dated Oct. 6, 2025.
U.S. Appl. No. 18/438,060 Office Action dated Oct. 7, 2025.
Vivian H. Lin, Curriculum Vitae (No date available).
Xavier et al., Gene Expression Control by Glucocorticoid Receptors during Innate Immune Responses. Front. Endocrinol. 7:31 (2016).
Xue et al. Glucocorticoid Modulates Angiotensin II Receptor Expression Patterns and Protects the Heart from Ischemia and Reperfusion Injury. PLoS One 9(9):e106827 (2014).

(56) References Cited

OTHER PUBLICATIONS

Deak, T. et al. The impact of the nonpeptide corticotropin-releasing hormone antagonist antalarmin on behavioral and endocrine responses to stress. Endocrinology 140(1):79-86 (1999).
U.S. Appl. No. 18/078,649 Office Action dated Nov. 18, 2025.

* cited by examiner

Subject in target range
* Subject entered study within target range

ACTH: 7.2-63.3 pg/mL 17-OHP: <1200 ng/dL A4: 41-262 ng/dL (M) 27-152 ng/dL (F)

METHODS FOR TREATING TESTICULAR AND OVARIAN ADRENAL REST TUMORS

CROSS-REFERENCE

This application is a continuation of U.S. application Ser. No. 18/941,832, filed Nov. 8, 2024, which is a continuation of U.S. application Ser. No. 17/667,285, filed on Feb. 8, 2022, which is a continuation of U.S. application Ser. No. 17/081,694 filed on Oct. 27, 2020, which issued as U.S. Pat. No. 11,304,950 on Apr. 19, 2022, and which is a continuation of International Application No. PCT/US2019/029486 filed on Apr. 26, 2019, which claims the benefit of U.S. Provisional Patent Application No. 62/663,951, filed Apr. 27, 2018, and U.S. Provisional Patent Application No. 62/822,815, filed Mar. 23, 2019, each of which is entirely incorporated herein by reference.

BACKGROUND

Corticotropes are basophilic cells in the anterior pituitary that produce melanocyte-stimulating hormone, adrenocorticotropic hormone (ACTH) and lipotropin. The cells produce pro-opiomelanocortin (POMC) which undergoes cleavage to ACTH and β-lipotropin (β-LPH). These cells respond to corticotropin-releasing factor (CRF) and make up about 20% of the cells in the anterior pituitary. CRF is a releasing hormone that belongs to the corticotropin-releasing factor family and is the primary physiological regulator of proopiomelanocortin (POMC).

CRF is produced by parvocellular neuroendocrine cells within the paraventricular nucleus of the hypothalamus and is released at the median eminence from neurosecretory terminals of these neurons into the primary capillary plexus of the hypothalamo-hypophyseal portal system. The portal system carries the CRF to the anterior lobe of the pituitary, where it stimulates corticotropes to secrete ACTH and other biologically-active substances. ACTH, in turn, stimulates the synthesis of cortisol, glucocorticoids, mineralocorticoids and DHEA.

Testicular adrenal rest tumors (TART) and ovarian adrenal rest tumors (OART) are ACTH-responsive lesions of the testes and ovaries derived from adrenal tissue interchelated within these organs during embryogenesis. In response to high ACTH, hyperplasia of this tissue occurs, resulting in single or multiple lesions that may cause pain and infertility. The identification of compounds that modulate CRF function and downstream processes is an ongoing challenge. Currently, there are no non-steroidal, non-surgical solutions to control, shrink, or reduce TART. Disclosed herein, inter alia, are solutions to these and other problems in the art.

SUMMARY

Congenital adrenal hyperplasia (CAH) due to 21-hydroxylase deficiency is a serious genetic disorder characterized by impaired adrenal synthesis of cortisol and consequent overproduction of adrenocorticotropic hormone (ACTH), 17-hydroxyprogesterone (17OHP), and adrenal androgens such as androstenedione (A4). CAH is an orphan condition with no FDA-approved therapy. To suppress androgen production, patients are often prescribed long-term supraphysiologic doses of glucocorticoid (GC), which has adverse effects and fail to suppress 17OHP and A4 in the majority of patients.

Compound 1 may be a potent, selective, nonsteroidal, oral corticotropin-releasing factor type-1 (CRF1) receptor antagonist that reduces excess ACTH, 17OHP, and A4 to improve clinical and biochemical sequelae of CAH. This may obviate the need for high dose steroids.

One aspect provided herein is a method of treating or preventing testicular adrenal rest tumors (TART) or ovarian adrenal rest tumors (OART), comprising administering to a subject in need thereof a corticotropin-releasing factor type-1 ($CRF_1$) antagonist or a pharmaceutically acceptable salt thereof.

In some embodiments, the subject has congenital adrenal hyperplasia (CAH). In some embodiments, the size and/or number of the tumors is decreased or reduced.

One aspect provided herein is a method of treating or preventing testicular adrenal rest tumors (TART) or ovarian adrenal rest tumors (OART), comprising administering to a subject in need thereof a compound of structural Formula (I):

(I)

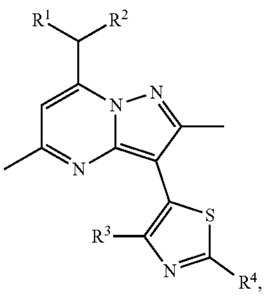

or a pharmaceutically acceptable salt thereof, wherein:

$R^1$ and $R^2$ are independently ethyl or n-propyl;

$R^3$ is hydrogen, Cl, Br, methyl, trifluoromethyl, or methoxy; and $R^4$ is hydrogen, Br, $R^aR^bN$—, methoxymethyl, n-butyl, acetamido, pyridin-4-yl, morpholin-4-yl,

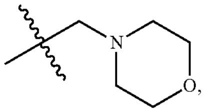

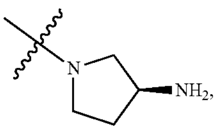

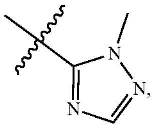

or

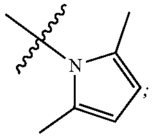

$R^a$ and $R^b$ are independently hydrogen, $C_1$-$C_3$alkyl, $H_2NCH_2CH_2$—, $(CH_3)_3COC(O)NHCH_2CH_2$—, or $CH_3CH_2CH_2NHCH_2CH_2$—.

In some embodiments, $R^3$ is Cl, Br, methyl, or trifluoromethyl. In some embodiments, $R^3$ is Cl, Br, or methyl. In some embodiments, $R^4$ is Br, $R^aR^bN$—, pyridin-4-yl, morpholin-4-yl, or

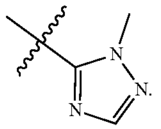

In some embodiments, $R^4$ is morpholin-4-yl or

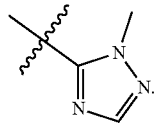 [SMILES: *c1ncnn1C]

In some embodiments, $R^4$ is hydrogen, Br, $R^aR^bN$— and $R^a$ and $R^b$ are independently $C_1$-$C_3$alkyl. In some embodiments, the compound is

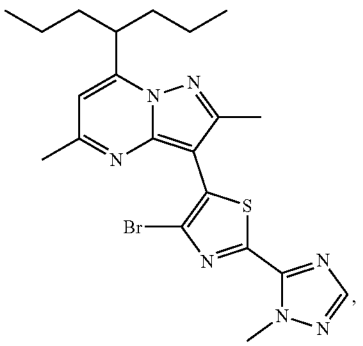 [SMILES: CCCC(CCC)c1cc(C)nc2c(-c3sc(-c4ncnn4C)nc3Br)c(C)nn12]

or a pharmaceutically acceptable salt thereof.

In some embodiments, the compound is

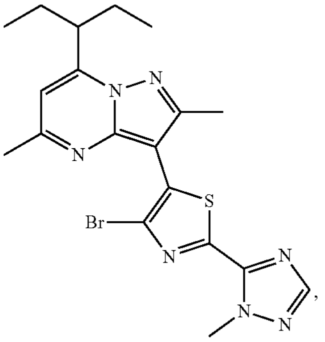 [SMILES: CCC(CC)c1cc(C)nc2c(-c3sc(-c4ncnn4C)nc3Br)c(C)nn12]

or a pharmaceutically acceptable salt thereof.

In some embodiments, the compound is

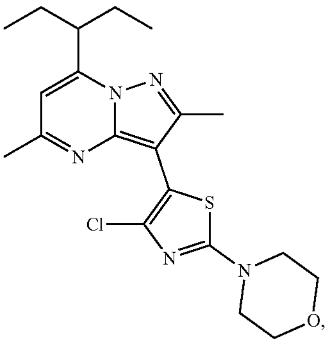 [SMILES: CCC(CC)c1cc(C)nc2c(-c3sc(N4CCOCC4)nc3Cl)c(C)nn12]

or a pharmaceutically acceptable salt thereof.

In some embodiments, the subject has congenital adrenal hyperplasia (CAH). In some embodiments, the size and/or number of the tumors is decreased or reduced.

In some embodiments, from about 5 mg to about 1000 mg of a compound of Formula (I), or a pharmaceutically acceptable salt thereof, is administered to the subject. In some embodiments, from about 5 mg to about 25 mg of a compound of Formula (I), or a pharmaceutically acceptable salt thereof, is administered to the subject. In some embodiments, from about 10 mg to about 400 mg of a compound of Formula (I), or a pharmaceutically acceptable salt thereof, is administered to the subject. In some embodiments, from about 100 mg to about 600 mg of a compound of Formula (I), or a pharmaceutically acceptable salt thereof, is administered to the subject.

In some embodiments, the compound of Formula (I), or a pharmaceutically acceptable salt thereof, is administered at a dose of from about 5 mg/day to about 1000 mg/day is administered to the subject. In some embodiments, the compound of Formula (I), or a pharmaceutically acceptable salt thereof, is administered at a dose from about 5 mg/day to about 25 mg/day is administered to the subject. In some embodiments, the compound of Formula (I), or a pharmaceutically acceptable salt thereof, is administered at a dose from about 10 mg/day to about 400 mg/day is administered to the subject. In some embodiments, the compound of Formula (I), or a pharmaceutically acceptable salt thereof, is administered at a dose of from about 100 mg/day to about 600 mg/day is administered to the subject.

In some embodiments, the compound is administered orally. In some embodiments, the compound is formulated as a capsule or tablet. In some embodiments, the compound of Formula (I), or a pharmaceutically acceptable salt thereof, is administered in the fed state. In some embodiments, the compound of Formula (I), or a pharmaceutically acceptable salt thereof, is administered in the fasted state.

In some embodiments, the compound of Formula (I), or a pharmaceutically acceptable salt thereof, is administered at least once per day. In some embodiments, the compound of Formula (I), or a pharmaceutically acceptable salt thereof, is administered at bedtime. In some embodiments, the compound of Formula (I), or a pharmaceutically acceptable salt thereof, is administered less than about 4 hours before sleep. In some embodiments, the compound of Formula (I), or a pharmaceutically acceptable salt thereof, is administered less than about 2 hours before sleep. In some embodiments, the compound of Formula (I), or a pharmaceutically acceptable salt thereof, is administered less than about 30 minutes before sleep. In some embodiments, the compound of Formula (I), or a pharmaceutically acceptable salt thereof, is administered in the evening. In some embodiments, the compound of Formula (I), or a pharmaceutically acceptable salt thereof, is administered at about 10 pm at night.

One aspect described herein is a method of treating or preventing testicular adrenal rest tumors (TART) or ovarian adrenal rest tumors (OART), comprising administering to a subject in need thereof a pharmaceutical composition, comprising a compound of structural Formula (I) and a pharmaceutically acceptable excipient:

(I)

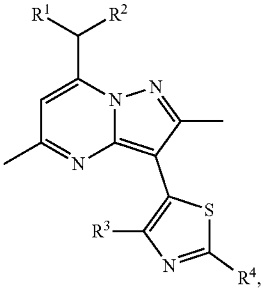

or a pharmaceutically acceptable salt thereof, wherein:

$R^1$ and $R^2$ are independently ethyl or n-propyl;

$R^3$ is hydrogen, Cl, Br, methyl, trifluoromethyl, or methoxy; and $R^4$ is hydrogen, Br, $R^aR^bN$—, methoxymethyl, n-butyl, acetamido, pyridin-4-yl, morpholin-4-yl,

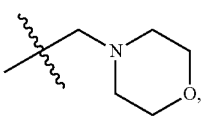,

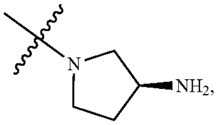,

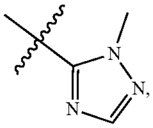 [SMILES: *c1ncnn1C], or

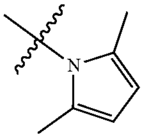;

$R^a$ and $R^b$ are independently hydrogen, $C_1$-$C_3$alkyl, $H_2NCH_2CH_2$—, $(CH_3)_3COC(O)NHCH_2CH_2$—, or $CH_3CH_2CH_2NHCH_2CH_2$—.

In some embodiments, the compound of Formula (I) has the structure:

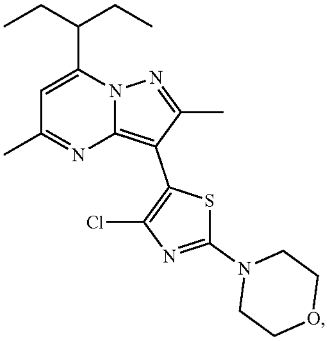, or a pharmaceutically acceptable salt thereof.

In some embodiments, the pharmaceutical composition comprises from about 5 mg to about 1000 mg of a compound of Formula (I), or a pharmaceutically acceptable salt thereof. In some embodiments, the pharmaceutical composition comprises from about 5 mg to about 25 mg of a compound of Formula (I), or a pharmaceutically acceptable salt thereof. In some embodiments, the pharmaceutical composition comprises from about 10 mg to about 400 mg of a compound of Formula (I), or a pharmaceutically acceptable salt thereof.

In some embodiments, the pharmaceutical composition comprises from about 100 mg to about 600 mg of a compound of Formula (I), or a pharmaceutically acceptable salt thereof.

In some embodiments, the pharmaceutical composition comprises about 5 mg, about 10 mg, about 15 mg, about 20 mg, 25 mg, about 50 mg, about 100 mg, about 150 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg about 500 mg, or about 600 mg of a compound of Formula (I), or a pharmaceutically acceptable salt thereof.

In some embodiments, the pharmaceutical composition is administered at a dose of from about 5 mg/day to about 1000 mg/day. In some embodiments, the pharmaceutical composition is administered at a dose of from about 5 mg/day to about 25 mg/day. In some embodiments, the pharmaceutical composition is administered at a dose of from about 10 mg/day to about 400 mg/day. In some embodiments, the pharmaceutical composition is administered at a dose of from about 100 mg/day to about 600 mg/day.

In some embodiments, the pharmaceutical composition is administered orally. In some embodiments, the pharmaceutical composition is formulated as capsule or a tablet. In some embodiments, the pharmaceutical composition is administered in the fed state. In some embodiments, the pharmaceutical composition is administered in the fasted state. In some embodiments, the pharmaceutical composition is administered at least once per day.

In some embodiments, the pharmaceutical composition is administered at bedtime. In some embodiments, the pharmaceutical composition is administered less than about 4 hours before sleep. In some embodiments, the pharmaceutical composition is administered less than about 2 hours before sleep. In some embodiments, the pharmaceutical composition is administered less than about 30 minutes before sleep. In some embodiments, the pharmaceutical composition is administered in the evening. In some embodiments, the pharmaceutical composition is administered at about 10 pm at night.

In some embodiments, the method further comprises administering to the subject an additional chemotherapeutic agent. In some embodiments, the additional chemotherapeutic agent is a glucocorticoid, a mineralocorticoid, an ACAT1 inhibitor, or an anti-androgen. In some embodiments, the glucocorticoid is beclomethasone, betamethasone, budesonide, cortisone, dexamethasone, hydrocortisone, methylprednisolone, prednisolone, prednisone, or triamcinolone. In some embodiments, the mineralocorticoid is fludrocortisone.

In some embodiments, the additional chemotherapeutic agent is another $CRF_1$ antagonist. In some embodiments, the $CRF_1$ antagonist is

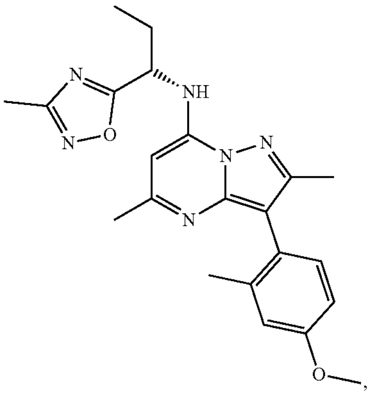

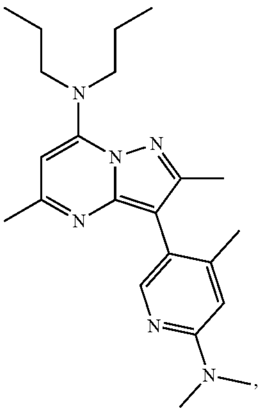

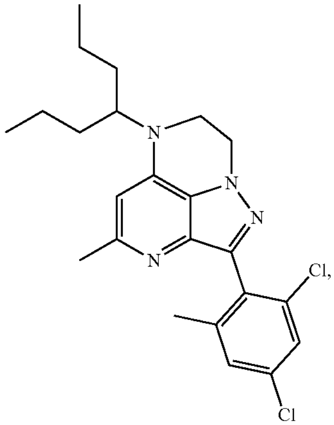

SSR-126374,

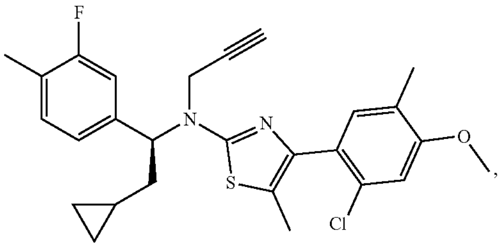

-continued

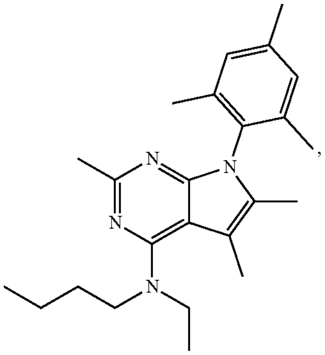

, or

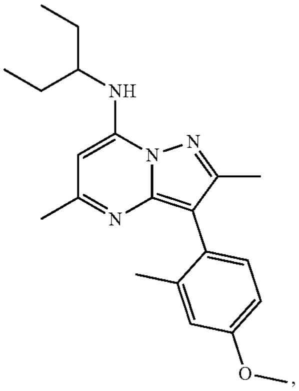

or a pharmaceutically acceptable salt thereof.

In some embodiments, the $CRF_1$ antagonist is

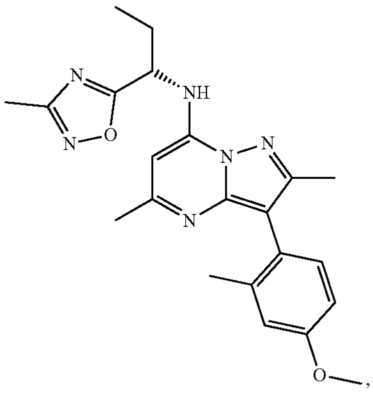

or a pharmaceutically acceptable salt thereof.

In some embodiments, the method further comprises an additional treatment selected from surgical resection of the tumors and radiation therapy, or a combination thereof.

In some embodiments, the additional therapy is surgical resection and the surgical resection is prior to, after, and/or concurrent with administration of the compound of structural Formula (I), or a pharmaceutically acceptable salt thereof or the pharmaceutical composition, or any combination thereof.

In some embodiments, the surgical resection is prior to administration of the compound of structural Formula (I), or a pharmaceutically acceptable salt thereof or the pharmaceutical composition. In some embodiments, the surgical resection is after administration of the compound of structural Formula (I), or a pharmaceutically acceptable salt thereof or the pharmaceutical composition. In some embodiments, the surgical resection is concurrent with administration of the compound of structural Formula (I), or a pharmaceutically acceptable salt thereof or the pharmaceutical composition.

In some embodiments, the additional treatment is radiation therapy and the radiation therapy is prior to, after, and/or concurrent with administration of the compound of structural Formula (I), or a pharmaceutically acceptable salt thereof or the pharmaceutical composition, or any combination thereof. In some embodiments, the radiation therapy is prior to administration of the $CRF_1$ antagonist of structural Formula (I), or a pharmaceutically acceptable salt thereof or the pharmaceutical composition.

In some embodiments, the radiation therapy is after administration of the compound of structural Formula (I), or a pharmaceutically acceptable salt thereof or the pharmaceutical composition. In some embodiments, the radiation therapy is concurrent with administration of the compound of structural Formula (I), or a pharmaceutically acceptable salt thereof or the pharmaceutical composition.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1A:
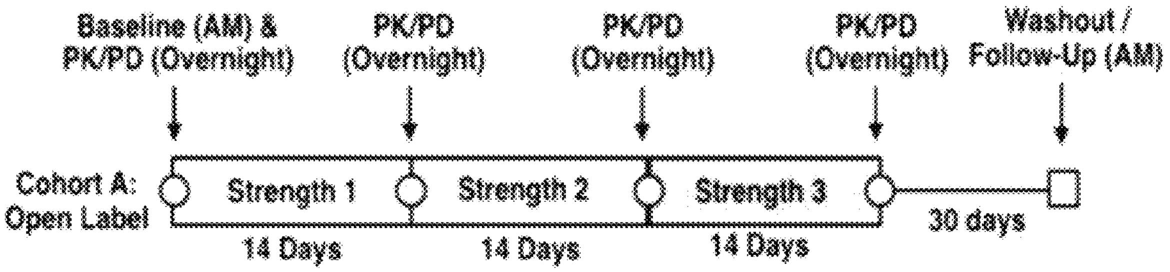
FIG. 1A-1B. A schematic representation of intra-patient dose escalation study to evaluate safety, pharmacokinetics, and pharmacodynamics (A). A schematic representation of inhibition of $CRF_1$ with a $CRF_1$ antagonist (Compound 1) (B).

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S$(O)_2$—$CH_3$, —CH═CH—O—$CH_3$, —Si$(CH_3)_3$, —$CH_2$—CH═N—$OCH_3$, —CH═CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si$(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C$(O)_2$R'— represents both —C$(O)_2$R'— and —R'C$(O)_2$—. As described above, heteroalkyl groups, as used herein, include those groups that are attached to the remainder of the molecule through a heteroatom, such as —C(O)R', —C(O)NR', —NR'R", —OR', —SR', and/or —$SO_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. "Cycloalkyl" is also meant to refer to bicyclic and polycyclic hydrocarbon rings such as, for example, bicyclo[2.2.1]heptane, bicyclo[2.2.2]octane, etc.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "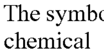" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

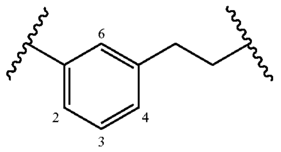

or

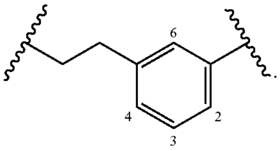

.

An alkylarylene moiety may be substituted (e.g. with a substituent group) on the alkylene moiety or the arylene linker (e.g. at carbons 2, 3, 4, or 6) with halogen, oxo, $—N_3$, $—CF_3$, $—CCl_3$, $—CBr_3$, $—CI_3$, —CN, —CHO, —OH, $—NH_2$, —COOH, $—CONH_2$, $—NO_2$, —SH, $—SO_2CH_3$—$SO_3H$, $—OSO_3H$, $—SO_2NH_2$, $—NHNH_2$, $—ONH_2$, $—NHC(O)NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', $—CO_2R'$, —CONR'R", —OC(O)NR'R", —NR"C(O)R', —NR'—C(O)NR"R"', $—NR"C(O)_2R'$, —NR—C(NR'R"R"')=NR"", —NR—C(NR'R")=NR"', —S(O)R', $—S(O)_2R'$, $—S(O)_2NR'R"$, $—NRSO_2R'$, —NR'NR"R"', —ONR'R", —NR'C(O)NR"NR"'R"", —CN, $—NO_2$, $—NR'SO_2R"$, —NR'C(O)R", —NR'C(O)—OR", —NR'OR", in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., $—CF_3$ and $—CH_2CF_3$) and acyl (e.g., $—C(O)CH_3$, $—C(O)CF_3$, $—C(O)CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C$(O)_2$R', —NR—C(NR'R"R'")=NR"", —NR—C(NR'R")=NR'", —S(O)R', —$S(O)_2$R', —$S(O)_2$NR'R", —NR$SO_2$R', —NR'NR"R'", —ONR'R", —NR'C(O)NR"NR'"R"", —CN, —$NO_2$, —R', —$N_3$, —$CH(Ph)_2$, fluoro($C_1$-$C_4$)alkoxy, and fluoro($C_1$-$C_4$)alkyl, —NR'$SO_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—$(CRR')_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —$S(O)_2$—, —$S(O)_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —$(CRR')_s$—X'—$(C"R"R'")_d$—, where s and d are independently integers of from 0 to 3, and X is —O—, —NR'—, —S—, —S(O)—, —$S(O)_2$—, or —$S(O)_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —$CF_3$, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC=(O)$NHNH_2$, —NHC=(O)$NH_2$, —$NHSO_2$H, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —$CF_3$, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC=(O)$NHNH_2$, —NHC=(O)$NH_2$, —$NHSO_2$H, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —$CF_3$, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC=(O)$NHNH_2$, —NHC=(O)$NH_2$, —$NHSO_2$H, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, $—OCF_3$, $—OCHF_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog" or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radiolabeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents. In embodiments, compounds of the present invention contain both basic and acidic functionalities that allow the compounds to be converted into either base or acid addition salts. The neutral forms of the compounds may be regenerated by contacting the salt with a base or acid and isolating the parent compound in a conventional manner. The parent form of the compounds differs from the various salt forms in certain physical properties, such as solubility in polar solvents, but, unless specifically indicated, the salts disclosed herein are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of a compound to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

A "CRF1 inhibitor" refers to a compound (e.g., compounds described herein) that reduces the activity of CRF1 when compared to a control, such as absence of the compound or a compound with known inactivity.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer. In embodiments, the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence; fusion proteins with heterologous and homologous leader sequences, with or without N-terminus methionine residues; immunologically tagged proteins; and the like.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway (e.g., MAP kinase pathway).

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist. In embodiments, an agonist is a molecule that interacts with a target to cause or promote an increase in the activation of the target. In embodiments, activators are molecules that increase, activate, facilitate, enhance activation, sensitize, or up-regulate, e.g., a gene, protein, ligand, receptor, or cell.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist. An antagonist prevents, reduces, inhibits, or neutralizes the activity of an agonist, and an antagonist can also prevent, inhibit, or reduce constitutive activity of a target, e.g., a target receptor, even where there is no identified agonist. In embodiments, inhibitors are molecules that decrease, block, prevent, delay activation, inactivate, desensitize, or down-regulate, e.g., a gene, protein, ligand, receptor, or cell. An inhibitor may also be defined as a molecule that reduces, blocks, or inactivates a constitutive activity. An "antagonist" is a molecule that opposes the action(s) of an agonist.

The terms "corticotropin-releasing factor type-1," "$CRF_1$," "corticotropin-releasing hormone receptor 1," and "CHHR1" refer to a protein (including homologs, isoforms, and functional fragments thereof) and is a receptor for corticotropin releasing-hormone. The terms include any recombinant or naturally-occurring form of $CRF_1$ variants thereof that maintain $CRF_1$ activity (e.g. within at least 30%, 40%, 50%, 60%, 70%, 80%, 90%, 95%, or 100% activity compared to wildtype CRF1). The terms include any mutant form of $CRF_1$ variants (e.g., frameshift mutations) thereof that maintain $CRF_1$ activity (e.g. within at least 30%, 40%, 50%, 60%, 70%, 80%, 90%, 95%, or 100% activity compared to wildtype $CRF_1$). In embodiments, the $CRF_1$ protein encoded by the CRHR1 gene has the amino acid sequence set forth in or corresponding to Entrez 1233, UniProt P34998.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The terms "disease" or "condition" refer to a state of being or health status of a patient or subject capable of being treated with the compounds or methods provided herein. The disease may be a malignant or benign tumor (e.g., testicular adrenal rest tumors (TART) or ovarian adrenal rest tumors (OART)). The disease may be cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, adrenal, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including MDS, AML, ALL, ATLL and CML), or multiple myeloma.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include adrenal cancer and tumors (e.g., testicular adrenal rest tumors (TART) or ovarian adrenal rest tumors (OART)) brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "congenital adrenal hyperplasia" or "CAH" are any of several autosomal recessive diseases resulting from mutations of genes for enzymes mediating the biochemical steps of production of mineralocorticoids, glucocorticoids or sex steroids from cholesterol by the adrenal glands (steroidogenesis). These conditions involve excessive or deficient production of sex steroids and can alter development of primary or secondary sex characteristics in some affected infants, children, or adults.

"Adrenal rest tumor" refers to a neoplasm of the testis (or ovaries) consisting of adrenal tissue. It may be secondary to hyperplasia of an adrenal gland.

"Testicular adrenal rest tumor(s)" or "TART" and/or ovarian adrenal rest tumor(s) are a complication of congenital adrenal hyperplasia (CAH), which may develop from ectopic remnants of intra-testicular adrenal tissue stimulated by adrenocorticotropic hormone (ACTH) hypersecretion. TART lesions are typically located within the rete testis and are bilateral, synchronous, nodular and multiple. TART can lead to testicular structural damage, spermatogenesis disorders, infertility and mass-forming lesions.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifomi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, or carcinoma *villosum*.

The terms "treating" or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "prevent" refers to a decrease in the occurrence of disease symptoms in a patient. As indicated above, the prevention may be complete (no detectable symptoms) or partial, such that fewer symptoms are observed than would likely occur absent treatment. In embodiments, prevent refers to slowing the progression of the disease, disorder or condition or inhibiting progression thereof to a harmful or otherwise undesired state.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins). The therapeutically effective amount can be ascertained by measuring relevant physiological effects, and it can be adjusted in connection with the dosing regimen and diagnostic analysis of the subject's condition, and the like. By way of example, measurement of the serum level of a CRF1 inhibitor (or, e.g., a metabolite thereof) at a particular time post-administration may be indicative of whether a therapeutically effective amount has been administered.

For any compound described herein, the therapeutically effective amount can be initially determined from cell culture assays. Target concentrations will be those concentrations of active compound(s) that are capable of achieving the methods described herein, as measured using the methods described herein or known in the art.

Therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan. Adjusting the dose to achieve maximal therapeutic window efficacy or toxicity in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

The terms "QD," "qd," and "q.d." refer to once a day, i.e., a drug or therapeutic agent is administered once a day for the duration of the therapeutic regimen.

The terms "BD," "bd," and "b.i.d." refer to twice a day, i.e., a drug or therapeutic agent is administered two times a day for the duration of the therapeutic regimen.

The terms "QID," "qid," and "q.i.d." refer to three times a day, i.e., a drug or therapeutic agent is administered three times a day for the duration of the therapeutic regimen.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent, chemotherapeutic, or treatment for a neurodegenerative disease). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J Microencapsul.* 13:293-306, 1996; Chonn, *Curr. Opin. Biotechnol.* 6:698-708, 1995; Ostro, *Am. J Hosp. Pharm.* 46:1576-1587, 1989). The compositions of the present invention can also be delivered as nanoparticles.

By "co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). The compositions of the present invention can be delivered transdermally, by a topical route, or formulated as applicator sticks, solutions, suspensions, emulsions, gels, creams, ointments, pastes, jellies, paints, powders, and aerosols.

For any compound described herein, the therapeutically effective amount can be initially determined from cell culture assays. Target concentrations will be those concentrations of active compound(s) that are capable of achieving the methods described herein, as measured using the methods described herein or known in the art.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer (e.g. colon cancer), cardiovascular disease, metabolic disease, immune or inflammatory disease or disorder.

In some embodiments, co-administration includes administering one active agent within 0.5, 1, 2, 4, 6, 8, 10, 12, 16, 20, 24 hours, 2 days, 4 days, 1 week or 1 month of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer (e.g. colon cancer), cardiovascular disease, metabolic disease, immune or inflammatory disease or disorder.

The compounds described herein can be administered to treat a fertility disease or disorder and/or cancer. In this regard, the compounds disclosed herein may be administered either alone to treat such diseases or disorders or may be co-administered with another therapeutic agent to treat such diseases or disorders.

The compounds disclosed herein may be co-administered with an agonist or antagonist of $CRF_1$ function. The compounds described herein can be co-administered with conventional anti-cancer/chemotherapeutic.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec.RTM.), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rlL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol.™ (i.e. paclitaxel), Taxotere.™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta *Medica*), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta *Medica*), D-68144 (Asta *Medica*), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta *Medica*), D-68836 (Asta *Medica*), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

The compounds disclosed herein may be co-administered with an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a *vinca* alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin); (ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5.alpha.-reductase such as finasteride; (iii) an agent which inhibits cancer cell invasion (for example a metalloproteinase inhibitor like marimastat or an inhibitor of urokinase plasminogen activator receptor function); (iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazoli-n-4-amine (gefitinib, AZD 1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazoli-n-4-amine (CI 1033)), an inhibitor of the platelet-derived growth factor family, or an inhibitor of the hepatocyte growth factor family; (v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin .alpha.v.beta.3 function or an angiostatin); (vi) a vascular damaging agent such as combretastatin A4, or a compound disclosed in WO 99/02166, WO 00/40529, WO 00/41669, WO 01/92224, WO 02/04434 or WO 02/08213; (vii) an agent used in antisense therapy, for example one directed to one of the targets listed above, such as ISIS 2503, an anti-ras antisense; (viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In embodiments, the compounds disclosed herein can be co-administered with an antibody, such as a monoclonal antibody targeting B-Lymphocytes (such as CD20 (rituximab), MRA-aIL16R and T-Lymphocytes, CTLA4-Ig, HuMax 11-15) or antibody modulating Ig function such as anti-IgE (for example omalizumab).

In embodiments, treatment of cancer includes administration of an effective amount of at least two of the following: a CRF1 inhibitor, an inhibitor of the PD-L1/PD-1 pathway, an inhibitor of CTLA-4, an agonistic antibody of CD137 (4-1BB). In some embodiments, the method may comprise the use of two or more combinations.

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

In addition, a $CRF_1$ inhibitor may be combined with the therapeutic administration of immune cells, sometimes referred to as adoptive cell transfer. These cells may be cells from the patient, a genetically related or unrelated donor, they may be genetically modified (e.g. CAR-T cells, NK cells, etc), cell lines, genetically modified cell lines and live or dead versions of the above. CRF1 inhibitors may also be combined with vaccines of any kind (e.g. protein/peptide, viral, bacterial, cellular) to stimulate immune responses to cancer.

The $CRF_1$ inhibitors/$CRF_1$ antagonists disclosed herein can be administered by any acceptable route, such oral, intraadiposal, intraarterial, intraarticular, intracranial, intradermal, intralesional, intramusculay, intranasal, intraoculamoney, intrapericardial, intraperitoneal, intrapleural, intraprostatical, intrarectal, intrathecal, intratracheal, intratumoral, intraumbilical, intravaginal, intravenousl, intravesicullar, intravitreal, liposomal, local, mucosal, parenteral, rectal, subconjunctival, subcutaneous, sublingual, topical, transbuccal, transdermal, vaginal, in cremes, in lipid compositions, via a catheter, via a lavage, via continuous infusion, via infusion, via inhalation, via injection, via local delivery, via localized perfusion, bathing target cells directly, or any combination thereof.

The $CRF_1$ inhibitors/$CRF_1$ antagonists disclosed herein can be administered by any acceptable route, such oral, intraadiposal, intraarterial, intraarticular, intracranial, intradermal, intralesional, intramusculay, intranasal, intraocularal, intrapericardial, intraperitoneal, intrapleural, intraprostatical, intrarectal, intrathecal, intratracheal, intratumoral, intraumbilical, intravaginal, intravenousl, intravesicullar, intravitreal, liposomal, local, mucosal, parenteral, rectal, subconjunctival, subcutaneous, sublingual, topical, transbuccal, transdermal, vaginal, in cremes, in lipid compositions, via a catheter, via a lavage, via continuous infusion, via infusion, via inhalation, via injection, via local delivery, via localized perfusion, bathing target cells directly, or any combination thereof.

The $CRF_1$ inhibitors/$CRF_1$ antagonists disclosed herein may be administered once daily until study reached endpoint. The $CRF_1$ inhibitors/$CRF_1$ antagonists disclosed herein may be administered at least three times but in some studies four or more times depending on the length of the study and/or the design of the study.

The methods disclosed herein may be used in combination with additional cancer therapy. In some embodiments, the distinct cancer therapy comprises surgery, radiotherapy, chemotherapy, toxin therapy, immunotherapy, cryotherapy or gene therapy. In some embodiments, the cancer is a chemotherapy-resistant or radio-resistant cancer.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule. In some embodiments, a CRF1 associated disease modulator is a compound that reduces the severity of one or more symptoms of a disease associated with $CRF_1$ (e.g. an endocrine disorder, a cancer including but not limited to TART or OART). A $CRF_1$ modulator is a compound that increases or decreases the activity or function or level of activity or level of function of $CRF_1$. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an activator.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule. In embodiments, the terms "modulate", "modulation" and the like refer to the ability of a molecule (e.g., an activator or an inhibitor) to increase or decrease the function or activity of $CRF_1$, either directly or indirectly, relative to the absence of the molecule.

The term "associated" or "associated with" in the context of a substance or substance activity or function associated with a disease (e.g. a protein associated disease, an endocrine disorder, a disease associated with $CRF_1$ activity, a $CRF_1$ associated disease (e.g., testicular adrenal rest tumors (TART) or ovarian adrenal rest tumors (OART)) means that the disease (e.g., testicular adrenal rest tumors (TART) or ovarian adrenal rest tumors (OART)) is caused by (in whole or in part), or a symptom of the disease is caused by (in whole or in part) the substance or substance activity or function. For example, an endocrine disorder associated with $CRF_1$ activity or function may be an endocrine disorder that results (entirely or partially) from aberrant $CRF_1$ function (e.g. enzyme activity, protein-protein interaction, signaling pathway) or an endocrine disorder wherein a particular symptom of the disease is caused (entirely or partially) by aberrant $CRF_1$ activity or function. As used herein, what is described as being associated with a disease, if a causative agent, could be a target for treatment of the disease. For example, an endocrine disorder associated with $CRF_1$ activity or function or a $CRF_1$ associated disease (e.g., an endocrine disorder including but not limited to TART or OART), may be treated with a compound described herein (e.g., $CRF_1$ modulator, $CRF_1$ inhibitor, or $CRF_1$ antagonist), in the instance where increased $CRF_1$ activity or function (e.g. signaling pathway activity) causes the disease (e.g., an endocrine disorder such as TART or OART). For example, an endocrine disorder associated with $CRF_1$ activity or function or a $CRF_1$ associated endocrine disorder, may be treated with an $CRF_1$ modulator or $CRF_1$ inhibitor, in the instance where increased $CRF_1$ activity or function (e.g. signaling pathway activity) causes the disease.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propogated to other signaling pathway components. For example, binding of a $CRF_1$ with a compound as described herein may reduce the level of a product of the $CRF_1$ catalyzed reaction or the level of a downstream derivative of the product or binding may reduce the interactions between the $CRF_1$ or a reaction product and downstream effectors or signaling pathway components (e.g., MAP kinase pathway), resulting in changes in cell growth, proliferation, or survival.

As used herein, the terms "corticotropin-releasing factor type-1," "$CRF_1$," "corticotropin-releasing hormone receptor 1," and "CHHR1" and all other related art-accepted terms, many of which are set forth below, refer to a compound capable of modulating, either directly or indirectly, the $CRF_1$ receptor in an in vitro assay, an in vivo model, and/or other means indicative of therapeutic efficacy. The terms also refer to a compound that exhibits at least some therapeutic benefit in a human subject.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

"Substantially pure" indicates that a component makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition (percentage in a weight per weight basis).

The terms "specifically binds" and "selectively binds," when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least 10-times greater, at least 20-times greater, or at least 100-times greater than the affinity with any other antibody, or binding composition derived therefrom. In embodiments, the antibody will have an affinity that is greater than about $10^9$ liters/mol, as determined by, e.g., Scatchard analysis (Munsen, et al. (1980) Analyt. Biochem. 107:220-239).

The terms "DNA," "nucleic acid," "nucleic acid molecule," "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

As used herein, the terms "variants" and "homologs" are used interchangeably to refer to amino acid or nucleic acid sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring amino acid and nucleic acid sequences encoded thereby and their isoforms, as well as splice variants of a protein or gene. The terms also encompass nucleic acid sequences that vary in one or more bases from a naturally-occurring nucleic acid sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced (e.g., muteins); for example, the change is generated in the laboratory by human intervention ("hand of man"). Therefore, non-naturally occurring variants and homologs may also refer to those that differ from the naturally-occurring sequences by one or more conservative substitutions and/or tags and/or conjugates.

The term "muteins" as used herein refers broadly to mutated recombinant proteins. These proteins usually carry single or multiple amino acid substitutions and are frequently derived from cloned genes that have been subjected to site-directed or random mutagenesis, or from completely synthetic genes.

II. Compounds

In an aspect provided herein, is a compound of Formula (I):

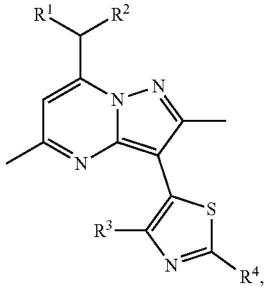

or a pharmaceutically acceptable salt thereof. $R^1$ and $R^2$ are independently ethyl or n-propyl. $R^3$ is hydrogen, Cl, Br, methyl, trifluoromethyl, or methoxy. $R^4$ is hydrogen, Br, $R^aR^bN$—, methoxymethyl, n-butyl, acetamido, pyridin-4-yl, morpholin-4-yl,

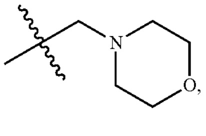 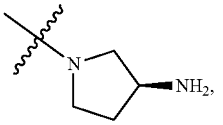

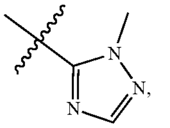 or 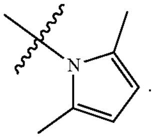

$R^a$ and $R^b$ are independently hydrogen, $C_1$-$C_3$alkyl, $H_2NCH_2CH_2$—, $(CH_3)_3COC(O)NHCH_2CH_2$—, or $CH_3CH_2CH_2NHCH_2CH_2$—In embodiments, the inhibitor forms an irreversible bond with the amino acid residue. In embodiments, the bond is a covalent bond.

In certain embodiments, $R^3$ is Cl, Br, methyl, or trifluoromethyl.

In certain embodiments, $R^3$ is Cl, Br, or methyl.

In certain embodiments, $R^4$ is Br, $R^aR^bN$—, pyridin-4-yl, morpholin-4-yl, or

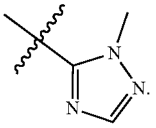

In certain embodiments, $R^4$ is morpholin-4-yl or

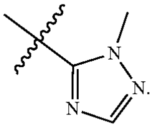

In certain embodiments, $R^4$ is hydrogen, Br, $R^aR^bN$— and $R^a$ and $R^b$ are independently $C_1$-$C_3$alkyl.

In certain embodiments, the compound is

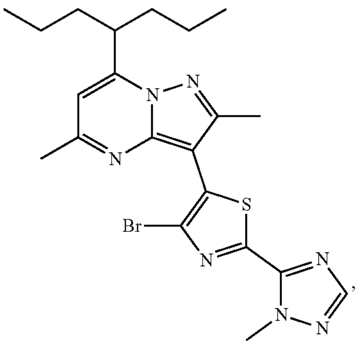 [SMILES: CCCC(CCC)c1cc(C)nc2c(-c3sc(-c4ncnn4C)nc3Br)c(C)nn12]

or a pharmaceutically acceptable salt thereof.

In certain embodiments, the compound is

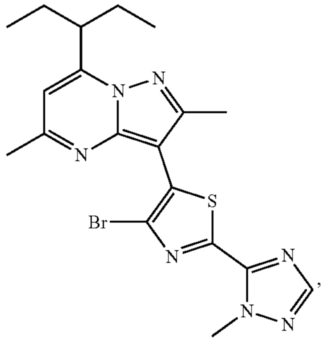 [SMILES: CCC(CC)c1cc(C)nc2c(-c3sc(-c4ncnn4C)nc3Br)c(C)nn12]

or a pharmaceutically acceptable salt thereof.

In certain embodiments, the compound is

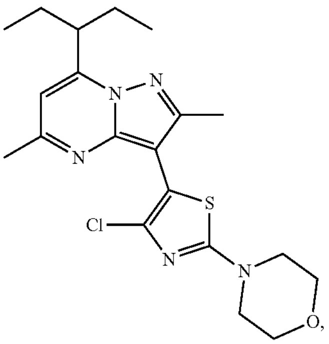 [SMILES: CCC(CC)c1cc(C)nc2c(-c3sc(N4CCOCC4)nc3Cl)c(C)nn12]

or a pharmaceutically acceptable salt thereof.

In one aspect described herein, there is a method of treating a subject in need thereof comprising administering an astressin or a pharmaceutically acceptable salt or solvate thereof. An astressin generally refers to a nonselective corticotropin releasing hormone antagonist that reduces the synthesis of ACTH and cortisol.

In one aspect described herein, there is a method of treating congenital adrenal hyperplasia (CAH) in a subject in need thereof, comprising administering an astressin or a variant having at least about 70% identity thereto or a pharmaceutically acceptable salt or solvate thereof. In one aspect described herein, there is a method of treating congenital adrenal hyperplasia (CAH) in a subject in need thereof, the method comprising: (i) measuring a hormone level in the subject in need thereof; (ii) administering an astressin or a variant having at least about 70% identity thereto, or a pharmaceutically acceptable salt or solvate thereof; and repeating steps (i) and (ii) until the hormone level reaches a pre-determined range followed by a maintenance therapy of a daily dosing of said astressin.

In one aspect described herein, there is a method of improving hyperandrogenic symptoms in a subject in need thereof, comprising administering an astressin or a variant having at least about 70% identity thereto, or a pharmaceutically acceptable salt or solvate thereof. In one aspect described herein, there is a method of treating menstrual irregularity, ovulatory dysfunction or infertility, in a subject in need thereof, comprising administering an astressin or a variant having at least about 70% identity thereto, or a pharmaceutically acceptable salt or solvate thereof. In one aspect described herein, there is a method of improving metabolic symptoms in a subject in need thereof, comprising administering an astressin or a variant having at least about 70% identity thereto; or a pharmaceutically acceptable salt or solvate thereof.

In one aspect described herein, there is a method of improving quality of life in a subject in need thereof, comprising administering an astressin or a variant having at least about 70% identity thereto, or a pharmaceutically acceptable salt or solvate thereof.

III. Pharmaceutical Compositions

In an aspect, there is provided a pharmaceutical composition, including a compound as described herein, including embodiments, or the structural Formula (I), and a pharmaceutically acceptable excipient.

The compounds (e.g., $CRF_1$ inhibitors/antagonists) of the present disclosure may be in the form of compositions suitable for administration to a subject. In general, such compositions are "pharmaceutical compositions" comprising a compound (e.g., $CRF_1$ inhibitor(s)/antagonist(s)) and one or more pharmaceutically acceptable or physiologically acceptable diluents, carriers or excipients. In certain embodiments, the compound (e.g., $CRF_1$ inhibitor/antagonist) are present in a therapeutically acceptable amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

In one aspect described herein, there is a pharmaceutical composition in the form of a capsule comprising an astressin or a variant having at least about 70% identity thereto, or a pharmaceutically acceptable salt or solvate thereof. In one aspect described herein, there is a pharmaceutical composition in the form of a tablet comprising an astressin or a variant having at least about 70% identity thereto, or a pharmaceutically acceptable salt or solvate thereof.

The pharmaceutical compositions of the present disclosure can be formulated to be compatible with the intended method or route of administration; exemplary routes of administration are set forth herein.

The pharmaceutical compositions containing the active ingredient (e.g., an inhibitor of $CRF_1$ function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture thereof. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated to delay disintegration and absorption in the gastrointestinal tract and thereby provide a sustained action. For example, a time-delay material such as glyceryl monostearate or glyceryl distearate may be employed. They may also be coated to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation.

Dispersible powders and granules suitable for preparation of an aqueous suspension by the addition of water provide the active ingredient in admixture with a dispersing or wetting agent, and optionally one or more suspending agents and/or preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of a $CRF_1$ inhibitor/antagonist contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate-buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer; N-(2-Hydroxyethyl)piperazine-N'-(2-ethanesulfonic acid) (HEPES); 2-(N-Morpholino)ethanesulfonic acid (MES); 2-(N-Morpholino)ethanesulfonic acid sodium salt (MES); 3-(N-Morpholino)propanesulfonic acid (MOPS); and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time-delay material such as glyceryl monostearate or glyceryl stearate alone, or in combination with a wax, may be employed. Any drug delivery apparatus may be used to deliver a $CRF_1$ inhibitor/antagonist, including implants (e.g., implantable pumps) and catheter systems, slow injection pumps and devices, all of which are well known to the skilled artisan.

Depot injections, which are generally administered subcutaneously or intramuscularly, may also be utilized to release the compound (e.g., $CRF_1$ inhibitor/antagonist) disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor® EL (BASF, Parsippany, NJ) or phosphate buffered saline (PBS), ethanol, polyol (e.g., glycerol, propylene glycol, and liquid polyethylene glycol), and suitable mixtures thereof. In addition, sterile fixed oils are conventionally employed as a solvent or suspending medium; for this purpose, any bland fixed oil may be employed, including synthetic mono- or diglycerides. Moreover, fatty acids, such as oleic acid, find use in the preparation of injectables. Prolonged absorption of particular injectable formulations can be achieved by including an agent that delays absorption (e.g., aluminum monostearate or gelatin).

The present disclosure contemplates the administration of the compound (e.g., $CRF_1$ inhibitor/antagonist) in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The compound (e.g., $CRF_1$ inhibitor/antagonist) contemplated by the present disclosure may be in the form of any other suitable pharmaceutical composition (e.g., sprays for nasal or inhalation use) currently known or developed in the future.

IV. Methods

In certain embodiments, provided herein are methods for treating or preventing a disease comprising administering an effective amount of a compound of Formula (I), or an isotopic variant thereof or a pharmaceutically acceptable salt, solvate, hydrate, or prodrug thereof.

In one embodiment, provided herein are methods for treating or preventing a tumor, comprising administering a compound of Formula (I), or an isotopic variant thereof; or a pharmaceutically acceptable salt, solvate, hydrate, or prodrug thereof. In one embodiment, provided herein are methods for treating or preventing a benign tumor, comprising administering a compound of Formula (I), or an isotopic variant thereof; or a pharmaceutically acceptable salt, solvate, hydrate, or prodrug thereof. In one embodiment, provided herein are methods for treating or preventing a malignant tumor, comprising administering a compound of Formula (I), or an isotopic variant thereof; or a pharmaceutically acceptable salt, solvate, hydrate, or prodrug thereof. In one embodiment, provided herein are methods for treating or preventing an adrenal tumor, comprising administering a compound of Formula (I), or an isotopic variant thereof; or a pharmaceutically acceptable salt, solvate, hydrate, or prodrug thereof. In one embodiment, provided herein are methods for treating or preventing an adrenal rest tumor, comprising administering a compound of Formula (I), or an isotopic variant thereof; or a pharmaceutically acceptable salt, solvate, hydrate, or prodrug thereof.

In one embodiment, provided herein are methods for treating or preventing infertility, comprising administering a compound of Formula (I), or an isotopic variant thereof; or a pharmaceutically acceptable salt, solvate, hydrate, or prodrug thereof. In one embodiment, provided herein are methods for treating or preventing male infertility, comprising administering a compound of Formula (I), or an isotopic variant thereof; or a pharmaceutically acceptable salt, solvate, hydrate, or prodrug thereof. In one embodiment, provided herein are methods for improving or increasing sperm count, comprising administering a compound of Formula (I), or an isotopic variant thereof; or a pharmaceutically acceptable salt, solvate, hydrate, or prodrug thereof. In one embodiment, provided herein are methods for improving or increasing sperm motility, comprising administering a compound of Formula (I), or an isotopic variant thereof; or a pharmaceutically acceptable salt, solvate, hydrate, or prodrug thereof. In one embodiment, provided herein are methods for improving or increasing sperm morphology, comprising administering a compound of Formula (I), or an isotopic variant thereof; or a pharmaceutically acceptable salt, solvate, hydrate, or prodrug thereof. In one embodiment, provided herein are methods for treating or preventing female infertility, comprising administering a compound of Formula (I), or an isotopic variant thereof; or a pharmaceutically acceptable salt, solvate, hydrate, or prodrug thereof.

In one embodiment, provided herein are methods for treating or preventing a proliferative or hyperproliferative disease or disorder, comprising administering a compound of Formula (I), or an isotopic variant thereof; or a pharmaceutically acceptable salt, solvate, hydrate, or prodrug thereof. In certain embodiments, the proliferative disease is cancer. In certain embodiments, the proliferative disease is a cancer of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system.

In certain embodiments, the cancer treatable with the methods provided herein includes, but is not limited to, (1) leukemias, including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome or a symptom thereof (such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia, and chronic myelomonocytic leukemia (CMML), (2) chronic leukemias, including, but not limited to, chronic myelocytic (granulocytic) leukemia, chronic lymphocytic leukemia, and hairy cell leukemia; (3) polycythemia vera; (4) lymphomas, including, but not limited to, Hodgkin's disease and non-Hodgkin's disease; (5) multiple myelomas, including, but not limited to, smoldering multiple myeloma, nonsecretory myeloma, osteosclerotic myeloma, plasma cell leukemia, solitary plasmacytoma, and extramedullary plasmacytoma; (6) Waldenstrom's macroglobulinemia; (7) monoclonal gammopathy of undetermined significance; (8) benign monoclonal gammopathy; (9) heavy chain disease; (10) bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, and synovial sarcoma; (11) brain tumors, including, but not limited to, glioma, astrocytoma, brain stem glioma, ependymoma, aligodendroglioma, nonglial tumor, acoustic neurinoma, craniopharyngioma, medulloblastoma, meningioma, pineocytoma, pineoblastoma, and primary brain lymphoma; (12) breast cancer, including, but not limited to, adenocarcinoma, lobular (small cell) carcinoma, intraductal carcinoma, medullary breast cancer, mutinous breast cancer, tubular breast cancer, papillary breast cancer, primary cancers, Paget's disease, and inflammatory breast cancer; (13) adrenal cancer, including, but not limited to, pheochromocytom and adrenocortical carcinoma; (14) thyroid cancer, including, but not limited to, papillary or follicular thyroid cancer, medullary thyroid cancer, and anaplastic thyroid cancer; (15) pancreatic cancer, including, but not limited to, insulinoma, gastrinoma, glucagonoma, vipoma, somatostatin-secreting tumor, and carcinoid or islet cell tumor; (16) pituitary cancer, including, but limited to, Cushing's disease, prol actin-secreting tumor, acromegaly, and diabetes insipius; (17) eye cancer, including, but not limited, to ocular melanoma such as iris melanoma, choroidal melanoma, and cilliary body melanoma, and retinoblastoma; (18) vaginal cancer, including, but not limited to, squamous cell carcinoma, adenocarcinoma, and melanoma; (19) vulvar cancer, including, but not limited to, squamous cell carcinoma, melanoma, adenocarcinoma, basal cell carcinoma, sarcoma, and Paget's disease; (20) cervical cancers, including, but not limited to, squamous cell carcinoma, and adenocarcinoma; (21) uterine cancer, including, but not limited to, endometrial carcinoma and uterine sarcoma; (22) ovarian cancer, including, but not limited to, ovarian epithelial carcinoma, borderline tumor, germ cell tumor, and stromal tumor; (23) esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; (24) stomach cancer, including, but not limited to, adenocarcinoma, fungating (polypoid), ulcerating, superficial spreading, diffusely spreading, malignant lymphoma, liposarcoma, fibrosarcoma, and carcinosarcoma; (25) colon cancer; (26) rectal cancer; (27) liver cancer, including, but not limited to, hepatocellular carcinoma and hepatoblastoma; (28) gallbladder cancer, including, but not limited to, adenocarcinoma; (29) cholangiocarcinomas, including, but not limited to, pappillary, nodular, and diffuse; (30) lung cancer, including, but not limited to, non-small cell lung cancer, squamous cell carcinoma (epidermoid carcinoma), adenocarcinoma, large-cell carcinoma, and small-cell lung cancer; (31) testicular cancer, including, but not limited to, germinal tumor, seminoma, anaplastic, classic (typical), spermatocytic, nonserninoma, embryonal carcinoma, teratoma carcinoma, and choriocarcinoma (yolk-sac tumor); (32) prostate cancer, including, but not limited to, adenocarcinoma, leiomyosarcoma, and rhabdomyosarcoma; (33) penal cancer; (34) oral cancer, including, but not limited to, squamous cell carcinoma; (35) basal cancer; (36) salivary gland cancer, including, but not limited to, adenocarcinoma, mucoepidermoid carcinoma, and adenoidcystic carcinoma; (37) pharynx cancer, including, but not limited to, squamous cell cancer and verrucous; (38) skin cancer, including, but not limited to, basal cell carcinoma, squamous cell carcinoma and melanoma, superficial spreading melanoma, nodular melanoma, lentigo malignant melanoma, and acral lentiginous melanoma; (39) kidney cancer, including, but not limited to, renal cell cancer, adenocarcinoma, hypemephroma, fibrosarcoma, and transitional cell cancer (renal pelvis and/or uterer); (40) Wilms' tumor; (41) bladder cancer, including, but not limited to, transitional cell carcinoma, squamous cell cancer, adenocarcinoma, and carcinosarcoma; and other cancer, including, not limited to, myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas (See Fishman et al., 1985, *Medicine,* 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

Depending on the disorder, disease, or condition to be treated, and the subject's condition, the compounds or pharmaceutical compositions provided herein can be administered by oral, parenteral (e.g., intramuscular, intraperitoneal, intravenous, ICV, intracistemal injection or infusion, subcutaneous injection, or implant), inhalation, nasal, vaginal, rectal, sublingual, or topical (e.g., transdermal or local) routes of administration and can be formulated, alone or together, in suitable dosage unit with pharmaceutically acceptable excipients, carriers, adjuvants, and vehicles appropriate for each route of administration as described elsewhere herein.

The suitability of a particular route of administration employed for a particular active agent will depend on the active agent itself (e.g., whether it can be administered orally without decomposing prior to entering the blood stream) and the disease being treated. Recommended routes of administration for the second active agents are known to those of ordinary skill in the art. See, e.g., Physicians' Desk Reference, 1755-1760 (56th ed., 2002).

In one embodiment, provided herein are methods for treating or preventing testicular adrenal rest tumors (TART) in a subject, comprising administering a compound of Formula (I), or an isotopic variant thereof; or a pharmaceutically acceptable salt, solvate, hydrate, or prodrug thereof, wherein the subject has congenital adrenal hyperplasia (CAH).

In one embodiment, provided herein are methods for treating or preventing ovarian adrenal rest tumors (OART) in a subject, comprising administering a compound of Formula (I), or an isotopic variant thereof; or a pharmaceutically acceptable salt, solvate, hydrate, or prodrug thereof, wherein the subject has congenital adrenal hyperplasia (CAH).

In an aspect provided herein, is a method of treating or preventing testicular adrenal rest tumors (TART), comprising administering to a subject in need thereof a corticotropin-releasing factor type-1 ($CRF_1$) antagonist or a pharmaceutically acceptable salt thereof.

In an aspect provided herein, is a method of treating or preventing ovarian adrenal rest tumors (OART), comprising administering to a subject in need thereof a corticotropin-releasing factor type-1 ($CRF_1$) antagonist or a pharmaceutically acceptable salt thereof.

In an aspect provided herein, is a method of treating or preventing testicular adrenal rest tumors (TART), comprising administering to a subject in need thereof a compound of structural Formula (I):

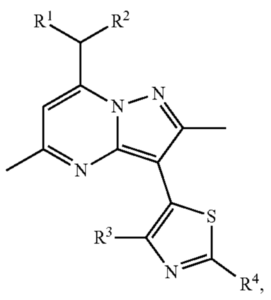

or a pharmaceutically acceptable salt thereof. $R^1$ and $R^2$ are independently ethyl or n-propyl. $R^3$ is hydrogen, Cl, Br, methyl, trifluoromethyl, or methoxy. $R^4$ is hydrogen, Br, $R^aR^bN$—, methoxymethyl, n-butyl, acetamido, pyridin-4-yl, morpholin-4-yl,

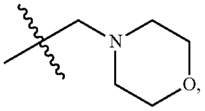 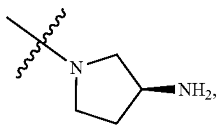

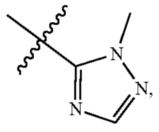 or 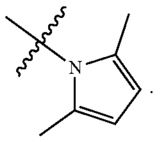

$R^a$ and $R^b$ are independently hydrogen, $C_1$-$C_3$alkyl, $H_2NCH_2CH_2$—, $(CH_3)_3COC(O)NHCH_2CH_2$—, or $CH_3CH_2CH_2NHCH_2CH_2$—.

In an aspect provided herein, is a method of treating or preventing ovarian adrenal rest tumors (OART), comprising administering to a subject in need thereof a compound of structural Formula (I):

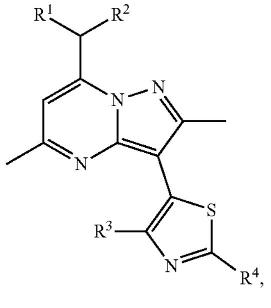

or a pharmaceutically acceptable salt thereof. $R^1$, $R^2$, $R^3$ and $R^4$ are as described herein, including embodiments.

In an aspect provided herein, is a method of decreasing or reducing adrenocorticotropic hormone (ACTH) levels in a subject in need thereof, comprising administering to the subject contacting the ACTH with a compound of structural Formula (I):

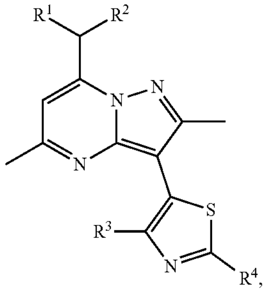

or a pharmaceutically acceptable salt thereof. $R^1$, $R^2$, $R^3$ and $R^4$ are as described herein, including embodiments. $R^1$, $R^2$, $R^3$ and $R^4$ are as described herein, including embodiments. In certain embodiments, at least about 50% of the subjects demonstrate reduction in ACTH. In certain embodiments, at least about 60% of the subjects demonstrate reduction in ACTH. In certain embodiments, at least about 70% of the subjects demonstrate reduction in ACTH. In certain embodiments, at least about 80% of the subjects demonstrate reduction in ACTH. In embodiments, at least about 10% of subjects were in the standard or normal range for ACTH after treatment.

In embodiments, at least about 20% of subjects were in the standard or normal range for ACTH after treatment. In embodiments, at least about 30% of subjects were in the standard or normal range for ACTH after treatment. In certain embodiments, ACTH levels are decreased or reduced within about 30 minutes post dosing. In certain embodiments, ACTH levels are decreased or reduced within about 1 hour post dosing. In certain embodiments, ACTH levels are decreased or reduced within about 90 minutes post dosing. In certain embodiments, ACTH levels are decreased or reduced within about 2 hours post dosing.

In an aspect provided herein, is a method of decreasing or reducing 17α-hydroxyprogesterone (17-OHP) levels in a subject in need thereof, comprising administering to the subject a compound of structural Formula (I):

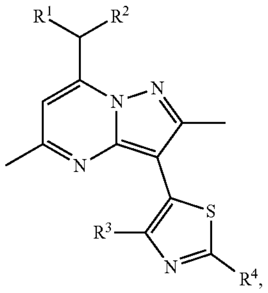

or a pharmaceutically acceptable salt thereof. $R^1$, $R^2$, $R^3$ and $R^4$ are as described herein, including embodiments. $R^1$, $R^2$, $R^3$ and $R^4$ are as described herein, including embodiments. In certain embodiments, at least about 50% of the subjects demonstrate reduction in 17-OHP. In certain embodiments, at least about 60% of the subjects demonstrate reduction in 17-OHP. In certain embodiments, at least about 70% of the subjects demonstrate reduction in 17-OHP. In certain embodiments, at least about 80% of the subjects demonstrate reduction in 17-OHP. In embodiments, at least about 30% of subjects were in the standard or normal range of 1200 ng/dL after treatment. In embodiments, at least about 40% of subjects were in the standard or normal range of 1200 ng/dL after treatment. In embodiments, at least about 50% of subjects were in the standard or normal range of 1200 ng/dL after treatment. In embodiments, at least about 60% of subjects were in the standard or normal range of 1200 ng/dL after treatment. In embodiments, at least about 30% of subjects demonstrated an at least about 25% reduction in 17-OHP after treatment. In embodiments, at least about 40% of subjects demonstrated an at least about 25% reduction in 17-OHP after treatment. In embodiments, at least about 50% of subjects demonstrated an at least about 25% reduction in 17-OHP after treatment. In embodiments, at least about 60% of subjects demonstrated an at least about 25% reduction in 17-OHP after treatment.

In an aspect provided herein, is a method of decreasing or reducing androstenedione levels in a subject in need thereof, comprising administering to the subject a compound of structural Formula (I):

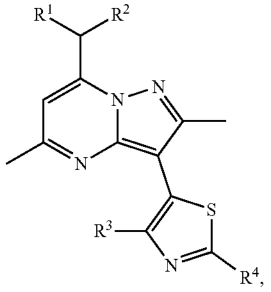

or a pharmaceutically acceptable salt thereof. $R^1$, $R^2$, $R^3$ and $R^4$ are as described herein, including embodiments. $R^1$, $R^2$, $R^3$ and $R^4$ are as described herein, including embodiments. In certain embodiments, at least about 50% of the subjects demonstrate reduction in androstenedione. In certain embodiments, at least about 60% of the subjects demonstrate reduction in androstenedione. In certain embodiments, at least about 70% of the subjects demonstrate reduction in androstenedione. In certain embodiments, at least about 80% of the subjects demonstrate reduction in androstenedione. In certain embodiments, at least about 90% of the subjects demonstrate reduction in androstenedione. In certain embodiments, at least 100% of the subjects demonstrate reduction in androstenedione. In embodiments, at least about 30% of subjects demonstrated an at least about 25% reduction in androstenedione after treatment. In embodiments, at least about 40% of subjects demonstrated an at least about 25% reduction in androstenedione after treatment. In embodiments, at least about 50% of subjects demonstrated an at least about 25% reduction in androstenedione after treatment. In embodiments, at least 60% of subjects demonstrated an at least about 25% reduction in androstenedione after treatment. In embodiments, at least about 30% of subjects were in the standard or normal range for androstenedione after treatment. In embodiments, at least about 40% of subjects were in the standard or normal range for androstenedione after treatment. In embodiments, at least about 50% of subjects were in the standard or normal range for androstenedione after treatment.

In certain embodiments, $R^3$ is Cl, Br, methyl, or trifluoromethyl.

In certain embodiments, $R^3$ is Cl, Br, or methyl.

In certain embodiments, $R^4$ is Br, $R^aR^bN$—, pyridin-4-yl, morpholin-4-yl, or

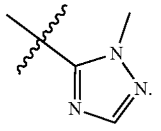 [SMILES: *c1ncnn1C]

In certain embodiments, $R^4$ is morpholin-4-yl or

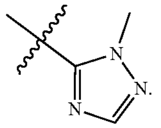 [SMILES: *c1ncnn1C]

In certain embodiments, $R^4$ is hydrogen, Br, $R^aR^bN$— and $R^a$ and $R^b$ are independently $C_1$-$C_3$alkyl.

In certain embodiments, the compound is

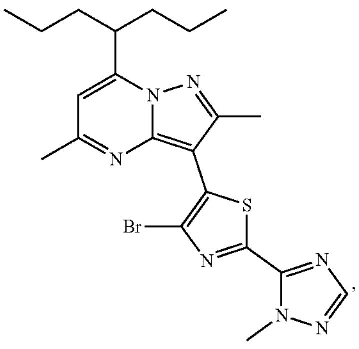 [SMILES: CCCC(CCC)c1cc(C)nc2c(-c3sc(-c4ncnn4C)nc3Br)c(C)nn12]

or a pharmaceutically acceptable salt thereof.

In certain embodiments, the compound is

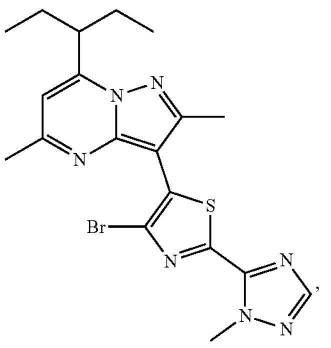 [SMILES: CCC(CC)c1cc(C)nc2c(-c3sc(-c4ncnn4C)nc3Br)c(C)nn12]

or a pharmaceutically acceptable salt thereof.

In certain embodiments, the compound is

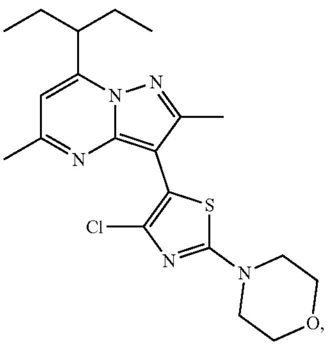 [SMILES: CCC(CC)c1cc(C)nc2c(-c3sc(N4CCOCC4)nc3Cl)c(C)nn12]

or a pharmaceutically acceptable salt thereof.

In certain embodiments, a compound of Formula (I), or an isotopic variant thereof; or a pharmaceutically acceptable salt, solvate, hydrate, or prodrug thereof is cyclically administered to a patient. Cycling therapy involves the administration of an active agent or a combination of active agents for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

In certain embodiments, in the treatment, prevention, or amelioration of one or more symptoms of the disorders, diseases, or conditions described herein (e.g., treatment or prevention of testicular adrenal rest tumors (TART) or treatment or prevention of ovarian adrenal rest tumors (OART)), an appropriate dosage level of a compound of Formula (I), or an isotopic variant thereof; or a pharmaceutically acceptable salt, solvate, hydrate, or prodrug thereof generally is ranging from about 1 mg to 3000 mg, from about 1 mg to 2000 mg, from about 1 mg to 1000 mg, from about 1 mg to about 500 mg, from about 5 mg to about 500 mg, from about 5 mg to about 400 mg, from about 5 mg to about 300 mg, from about 5 mg to about 250 mg, from about 5 mg to about 200 mg, from about 50 mg to about 200 mg, from about 10 mg to about 400 mg, from about 5 mg to about 25 mg, from about 10 mg to about 25 mg, or from about 25 to about 200 mg, which can be administered in single or multiple doses. In certain embodiments, the compound of Formula (I), or an isotopic variant thereof; or a pharmaceutically acceptable salt, solvate, hydrate, or prodrug thereof is administered in an amount of about 1 mg, about 5 mg, about 10 mg mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 450 mg, about 500 mg, about 600 mg, about 800 mg, or about 1000 mg. In certain embodiments, the compound of Formula (I), or an isotopic variant thereof; or a pharmaceutically acceptable salt, solvate, hydrate, or prodrug thereof is administered in an amount of about 1 mg, about 5 mg, about 10 mg mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 450 mg, about 500 mg, about 600 mg, about 800 mg, or about 1000 mg/day.

In certain embodiments, the compound of Formula (I), or an isotopic variant thereof; or a pharmaceutically acceptable salt, solvate, hydrate, or prodrug thereof is administered in an amount of about 5 mg. In certain embodiments, the compound of Formula (I), or an isotopic variant thereof; or a pharmaceutically acceptable salt, solvate, hydrate, or prodrug thereof is administered in an amount of about 10 mg. In certain embodiments, the compound of Formula (I), or an isotopic variant thereof; or a pharmaceutically acceptable salt, solvate, hydrate, or prodrug thereof is administered in an amount of about 15 mg. In certain embodiments, the compound of Formula (I), or an isotopic variant thereof; or a pharmaceutically acceptable salt, solvate, hydrate, or prodrug thereof is administered in an amount of about 20 mg. In certain embodiments, the compound of Formula (I), or an isotopic variant thereof; or a pharmaceutically acceptable salt, solvate, hydrate, or prodrug thereof is administered in an amount of about 25 mg. In certain embodiments, the compound of Formula (I), or an isotopic variant thereof; or a pharmaceutically acceptable salt, solvate, hydrate, or prodrug thereof is administered in an amount of about 50 mg. In certain embodiments, the compound of Formula (I), or an isotopic variant thereof; or a pharmaceutically acceptable salt, solvate, hydrate, or prodrug thereof is administered in an amount of about 100 mg. In certain embodiments, the compound of Formula (I), or an isotopic variant thereof; or a pharmaceutically acceptable salt, solvate, hydrate, or prodrug thereof is administered in an amount of about 150 mg. In certain embodiments, the compound of Formula (I), or an isotopic variant thereof; or a pharmaceutically acceptable salt, solvate, hydrate, or prodrug thereof is administered in an amount of about 200 mg. In certain embodiments, the compound of Formula (I), or an isotopic variant thereof; or a pharmaceutically acceptable salt, solvate, hydrate, or prodrug thereof is administered in an amount of about 210 mg. In certain embodiments, the compound of Formula (I), or an isotopic variant thereof; or a pharmaceutically acceptable salt, solvate, hydrate, or prodrug thereof is administered in an amount of about 220 mg. In certain embodiments, the compound of Formula (I), or an isotopic variant thereof; or a pharmaceutically acceptable salt, solvate, hydrate, or prodrug thereof is administered in an amount of about 230 mg. In certain embodiments, the compound of Formula (I), or an isotopic variant thereof; or a pharmaceutically acceptable salt, solvate, hydrate, or prodrug thereof is administered in an amount of about 240 mg. In certain embodiments, the compound of Formula (I), or an isotopic variant thereof; or a pharmaceutically acceptable salt, solvate, hydrate, or prodrug thereof is administered in an amount of about 250 mg. In certain embodiments, the compound of Formula (I), or an isotopic variant thereof; or a pharmaceutically acceptable salt, solvate, hydrate, or prodrug thereof is administered in an amount of about 260 mg. In certain embodiments, the compound of Formula (I), or an isotopic variant thereof; or a pharmaceutically acceptable salt, solvate, hydrate, or prodrug thereof is administered in an amount of about 270 mg. In certain embodiments, the compound of Formula (I), or an isotopic variant thereof; or a pharmaceutically acceptable salt, solvate, hydrate, or prodrug thereof is administered in an amount of about 280 mg. In certain embodiments, the compound of Formula (I), or an isotopic variant thereof; or a pharmaceutically acceptable salt, solvate, hydrate, or prodrug thereof is administered in an amount of about 290 mg. In certain embodiments, the compound of Formula (I), or an isotopic variant thereof; or a pharmaceutically acceptable salt, solvate, hydrate, or prodrug thereof is administered in an amount of about 300 mg. In certain embodiments, the compound of Formula (I), or an isotopic variant thereof; or a pharmaceutically acceptable salt, solvate, hydrate, or prodrug thereof is administered in an amount of about 310 mg. In certain embodiments, the compound of Formula (I), or an isotopic variant thereof; or a pharmaceutically acceptable salt, solvate, hydrate, or prodrug thereof is administered in an amount of about 320 mg. In certain embodiments, the compound of Formula (I), or an isotopic variant thereof; or a pharmaceutically acceptable salt, solvate, hydrate, or prodrug thereof is administered in an amount of about 330 mg. In certain embodiments, the compound of Formula (I), or an isotopic variant thereof; or a pharmaceutically acceptable salt, solvate, hydrate, or prodrug thereof is administered in an amount of about 340 mg. In certain embodiments, the compound of Formula (I), or an isotopic variant thereof; or a pharmaceutically acceptable salt, solvate, hydrate, or prodrug thereof is administered in an amount of about 350 mg. In certain embodiments, the compound of Formula (I), or an isotopic variant thereof; or a pharmaceutically acceptable salt, solvate, hydrate, or prodrug thereof is administered in an amount of about 360 mg. In certain embodiments, the compound of Formula (I), or an isotopic variant thereof; or a pharmaceutically acceptable salt, solvate, hydrate, or prodrug thereof is administered in an amount of about 370 mg. In certain embodiments, the compound of Formula (I), or an isotopic variant thereof; or a pharmaceutically acceptable salt, solvate, hydrate, or prodrug thereof is administered in an amount of about 380 mg. In certain embodiments, the compound of Formula (I), or an isotopic variant thereof; or a pharmaceutically acceptable salt, solvate, hydrate, or prodrug thereof is administered in an amount of about 390 mg. In certain embodiments, the compound of Formula (I), or an isotopic variant thereof; or a pharmaceutically acceptable salt, solvate, hydrate, or prodrug thereof is administered in an amount of about 400 mg. In certain embodiments, the compound of Formula (I), or an isotopic variant thereof; or a pharmaceutically acceptable salt, solvate, hydrate, or prodrug thereof is administered in an amount of about 450 mg. In certain embodiments, the compound of Formula (I), or an isotopic variant thereof; or a pharmaceutically acceptable salt, solvate, hydrate, or prodrug thereof is administered in an amount of about 500 mg. In certain embodiments, the compound of Formula (I), or an isotopic variant thereof; or a pharmaceutically acceptable salt, solvate, hydrate, or prodrug thereof is administered in an amount of about 600 mg. In certain embodiments, the compound of Formula (I), or an isotopic variant thereof; or a pharmaceutically acceptable salt, solvate, hydrate, or prodrug thereof is administered in an amount of about 700 mg. In certain embodiments, the compound of Formula (I), or an isotopic variant thereof; or a pharmaceutically acceptable salt, solvate, hydrate, or prodrug thereof is administered in an amount of about 800 mg. In certain embodiments, the compound of Formula (I), or an isotopic variant thereof; or a pharmaceutically acceptable salt, solvate, hydrate, or prodrug thereof is administered in an amount of about 900 mg. In certain embodiments, the compound of Formula (I), or an isotopic variant thereof; or a pharmaceutically acceptable salt, solvate, hydrate, or prodrug thereof is administered in an amount of about 1000 mg.

In certain embodiments, the compound of Formula (I), or an isotopic variant thereof; or a pharmaceutically acceptable salt, solvate, hydrate, or prodrug thereof is administered in an amount of about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, or about 1000 mg.

For oral administration, the pharmaceutical compositions provided herein can be formulated in the form of tablets or capsules containing from about 1.0 mg to about 1,000 mg of a compound of Formula (I), or an isotopic variant thereof; or a pharmaceutically acceptable salt, solvate, hydrate, or prodrug thereof. In certain embodiments, for oral administration, the pharmaceutical compositions provided herein can be formulated in the form of tablets or capsules containing about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, about 500 mg, about 505 mg, about 510 mg, about 515 mg, about 520 mg, about 525 mg, about 530 mg, about 535 mg, about 540 mg, about 545 mg, about 550 mg, about 555 mg, about 560 mg, about 565 mg, about 570 mg, about 575 mg, about 580 mg, about 585 mg, about 590 mg, about 595 mg, about 600 mg, about 605 mg, about 610 mg, about 615 mg, about 620 mg, about 625 mg, about 630 mg, about 635 mg, about 640 mg, about 645 mg, about 650 mg, about 655 mg, about 660 mg, about 665 mg, about 670 mg, about 675 mg, about 680 mg, about 685 mg, about 690 mg, about 695 mg, about 700 mg, about 705 mg, about 710 mg, about 715 mg, about 720 mg, about 725 mg, about 730 mg, about 735 mg, about 740 mg, about 745 mg, about 750 mg, about 755 mg, about 760 mg, about 765 mg, about 770 mg, about 775 mg, about 780 mg, about 785 mg, about 790 mg, about 795 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 990 mg, about 990 mg, or about 1000 mg of a compound of Formula (I), or an isotopic variant thereof; or a pharmaceutically acceptable salt, solvate, hydrate, or prodrug thereof for the symptomatic adjustment of the dosage to the patient to be treated. In certain embodiments, for oral administration, the pharmaceutical compositions provided herein can be formulated in the form of tablets or capsules containing about 50 mg of a compound of Formula (I), or an isotopic variant thereof; or a pharmaceutically acceptable salt, solvate, hydrate, or prodrug thereof. In certain embodiments, for oral administration, the pharmaceutical compositions provided herein can be formulated in the form of tablets or capsules containing about 200 mg of a compound of Formula (I), or an isotopic variant thereof; or a pharmaceutically acceptable salt, solvate, hydrate, or prodrug thereof. The pharmaceutical compositions can be administered on a regimen of one (1) to four (4) times per day, including once, twice, three times, and four times per day. In some embodiments, the compound of Formula (I), or an isotopic variant thereof; or a pharmaceutically acceptable salt, solvate, hydrate, or prodrug thereof is administered once per day. In some embodiments, about 5 mg, about 10 mg, about 15 mg, about 20 mg, about 25 mg, about 50 mg, about 100 mg, about 150 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, about 500 mg, about 505 mg, about 510 mg, about 515 mg, about 520 mg, about 525 mg, about 530 mg, about 535 mg, about 540 mg, about 545 mg, about 550 mg, about 555 mg, about 560 mg, about 565 mg, about 570 mg, about 575 mg, about 580 mg, about 585 mg, about 590 mg, about 595 mg, about 600 mg, about 605 mg, about 610 mg, about 615 mg, about 620 mg, about 625 mg, about 630 mg, about 635 mg, about 640 mg, about 645 mg, about 650 mg, about 655 mg, about 660 mg, about 665 mg, about 670 mg, about 675 mg, about 680 mg, about 685 mg, about 690 mg, about 695 mg, about 700 mg, about 705 mg, about 710 mg, about 715 mg, about 720 mg, about 725 mg, about 730 mg, about 735 mg, about 740 mg, about 745 mg, about 750 mg, about 755 mg, about 760 mg, about 765 mg, about 770 mg, about 775 mg, about 780 mg, about 785 mg, about 790 mg, about 795 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 990 mg, about 990 mg, or about 1000 mg of the compound of Formula (I), or an isotopic variant thereof; or a pharmaceutically acceptable salt, solvate, hydrate, or prodrug thereof is administered once per day. In some embodiments, about 5 mg, about 10 mg, about 15 mg, about 20 mg, about 25 mg, about 50 mg, about 100 mg, about 150 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, about 500 mg, about 505 mg, about 510 mg, about 515 mg, about 520 mg, about 525 mg, about 530 mg, about 535 mg, about 540 mg, about 545 mg, about 550 mg, about 555 mg, about 560 mg, about 565 mg, about 570 mg, about 575 mg, about 580 mg, about 585 mg, about 590 mg, about 595 mg, about 600 mg, about 605 mg, about 610 mg, about 615 mg, about 620 mg, about 625 mg, about 630 mg, about 635 mg, about 640 mg, about 645 mg, about 650 mg, about 655 mg, about 660 mg, about 665 mg, about 670 mg, about 675 mg, about 680 mg, about 685 mg, about 690 mg, about 695 mg, about 700 mg, about 705 mg, about 710 mg, about 715 mg, about 720 mg, about 725 mg, about 730 mg, about 735 mg, about 740 mg, about 745 mg, about 750 mg, about 755 mg, about 760 mg, about 765 mg, about 770 mg, about 775 mg, about 780 mg, about 785 mg, about 790 mg, about 795 mg, about 800 mg, about 850 mg, about 900 mg, about 950 mg, or about 1000 mg of the compound of Formula (I), or an isotopic variant thereof; or a pharmaceutically acceptable salt, solvate, hydrate, or prodrug thereof is administered twice per day. In some embodiments, about 5 mg, about 10 mg, about 15 mg, about 20 mg, about 25 mg, about 50 mg, about 100 mg, about 150 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, about 500 mg, about 505 mg, about 510 mg, about 515 mg, about 520 mg, about 525 mg, about 530 mg, about 535 mg, about 540 mg, about 545 mg, about 550 mg, about 555 mg, about 560 mg, about 565 mg, about 570 mg, about 575 mg, about 580 mg, about 585 mg, about 590 mg, about 595 mg, about 600 mg, about 605 mg, about 610 mg, about 615 mg, about 620 mg, about 625 mg, about 630 mg, about 635 mg, about 640 mg, about 645 mg, about 650 mg, about 655 mg, about 660 mg, about 665 mg, about 670 mg, about 675 mg, about 680 mg, about 685 mg, about 690 mg, about 695 mg, about 700 mg, about 705 mg, about 710 mg, about 715 mg, about 720 mg, about 725 mg, about 730 mg, about 735 mg, about 740 mg, about 745 mg, about 750 mg, about 755 mg, about 760 mg, about 765 mg, about 770 mg, about 775 mg, about 780 mg, about 785 mg, about 790 mg, about 795 mg, about 800 mg, about 850 mg, about 900 mg, about 950 mg, or about 1000 mg of the compound of Formula (I), or an isotopic variant thereof; or a pharmaceutically acceptable salt, solvate, hydrate, or prodrug thereof is administered three times per day.

In some embodiments, the compound of Formula (I), or an isotopic variant thereof; or a pharmaceutically acceptable salt, solvate, hydrate, or prodrug thereof is administered for a period of one day. In some embodiments, the compound of Formula (I), or an isotopic variant thereof; or a pharmaceutically acceptable salt, solvate, hydrate, or prodrug thereof is administered over a period of two days. In some embodiments, the compound of Formula (I), or an isotopic variant thereof; or a pharmaceutically acceptable salt, solvate, hydrate, or prodrug thereof is administered over a period of three days. In some embodiments, the compound of Formula (I), or an isotopic variant thereof; or a pharmaceutically acceptable salt, solvate, hydrate, or prodrug thereof is administered over a period of four days. In some embodiments, the compound of Formula (I), or an isotopic variant thereof; or a pharmaceutically acceptable salt, solvate, hydrate, or prodrug thereof is administered over a period of five days. In some embodiments, the compound of Formula (I), or an isotopic variant thereof; or a pharmaceutically acceptable salt, solvate, hydrate, or prodrug thereof is administered over a period of six days. In some embodiments, the compound of Formula (I), or an isotopic variant thereof; or a pharmaceutically acceptable salt, solvate, hydrate, or prodrug thereof is administered over a period of seven days. In some embodiments, the compound of Formula (I), or an isotopic variant thereof; or a pharmaceutically acceptable salt, solvate, hydrate, or prodrug thereof is administered over a period of eight days. In some embodiments, the compound of Formula (I), or an isotopic variant thereof; or a pharmaceutically acceptable salt, solvate, hydrate, or prodrug thereof is administered over a period of nine days. In some embodiments, the compound of Formula (I), or an isotopic variant thereof; or a pharmaceutically acceptable salt, solvate, hydrate, or prodrug thereof is administered over a period of ten days. In some embodiments, the compound of Formula (I), or an isotopic variant thereof; or a pharmaceutically acceptable salt, solvate, hydrate, or prodrug thereof is administered over a period of 11 days. In some embodiments, the compound of Formula (I), or an isotopic variant thereof; or a pharmaceutically acceptable salt, solvate, hydrate, or prodrug thereof is administered over a period of 12 days. In some embodiments, the compound of Formula (I), or an isotopic variant thereof; or a pharmaceutically acceptable salt, solvate, hydrate, or prodrug thereof is administered over a period of 13 days. In some embodiments, the compound of Formula (I), or an isotopic variant thereof; or a pharmaceutically acceptable salt, solvate, hydrate, or prodrug thereof is administered over a period of 14 days. In some embodiments, the compound of Formula (I), or an isotopic variant thereof; or a pharmaceutically acceptable salt, solvate, hydrate, or prodrug thereof is administered for a period of 15 days. In some embodiments, the compound of Formula (I), or an isotopic variant thereof; or a pharmaceutically acceptable salt, solvate, hydrate, or prodrug thereof is administered over a period of 16 days. In some embodiments, the compound of Formula (I), or an isotopic variant thereof; or a pharmaceutically acceptable salt, solvate, hydrate, or prodrug thereof is administered over a period of 17 days. In some embodiments, the compound of Formula (I), or an isotopic variant thereof; or a pharmaceutically acceptable salt, solvate, hydrate, or prodrug thereof is administered over a period of 18 days. In some embodiments, the compound of Formula (I), or an isotopic variant thereof; or a pharmaceutically acceptable salt, solvate, hydrate, or prodrug thereof is administered over a period of 19 days. In some embodiments, the compound of Formula (I), or an isotopic variant thereof; or a pharmaceutically acceptable salt, solvate, hydrate, or prodrug thereof is administered over a period of 20 days. In some embodiments, the compound of Formula (I), or an isotopic variant thereof; or a pharmaceutically acceptable salt, solvate, hydrate, or prodrug thereof is administered over a period of 21 days. In some embodiments, the compound of Formula (I), or an isotopic variant thereof; or a pharmaceutically acceptable salt, solvate, hydrate, or prodrug thereof is administered over a period of 22 days. In some embodiments, the compound of Formula (I), or an isotopic variant thereof; or a pharmaceutically acceptable salt, solvate, hydrate, or prodrug thereof is administered over a period of 23 days. In some embodiments, the compound of Formula (I), or an isotopic variant thereof; or a pharmaceutically acceptable salt, solvate, hydrate, or prodrug thereof is administered over a period of 24 days. In some embodiments, the compound of Formula (I), or an isotopic variant thereof; or a pharmaceutically acceptable salt, solvate, hydrate, or prodrug thereof is administered over a period of 25 days. In some embodiments, the compound of Formula (I), or an isotopic variant thereof; or a pharmaceutically acceptable salt, solvate, hydrate, or prodrug thereof is administered over a period of 26 days. In some embodiments, the compound of Formula (I), or an isotopic variant thereof; or a pharmaceutically acceptable salt, solvate, hydrate, or prodrug thereof is administered over a period of 27 days. In some embodiments, the compound of Formula (I), or an isotopic variant thereof; or a pharmaceutically acceptable salt, solvate, hydrate, or prodrug thereof is administered over a period of 28 days. In some embodiments, the compound of Formula (I), or an isotopic variant thereof; or a pharmaceutically acceptable salt, solvate, hydrate, or prodrug thereof is administered over a period of 29 days. In some embodiments, the compound of Formula (I), or an isotopic variant thereof; or a pharmaceutically acceptable salt, solvate, hydrate, or prodrug thereof is administered for a period of 30 days. In some embodiments, the compound of Formula (I), or an isotopic variant thereof; or a pharmaceutically acceptable salt, solvate, hydrate, or prodrug thereof is administered over a period of 31 days. In some embodiments, the compound of Formula (I), or an isotopic variant thereof; or a pharmaceutically acceptable salt, solvate, hydrate, or prodrug thereof is administered over a period of 32 days. In some embodiments, the compound of Formula (I), or an isotopic variant thereof; or a pharmaceutically acceptable salt, solvate, hydrate, or prodrug thereof is administered over a period of 33 days. In some embodiments, the compound of Formula (I), or an isotopic variant thereof; or a pharmaceutically acceptable salt, solvate, hydrate, or prodrug thereof is administered over a period of 34 days. In some embodiments, the compound of Formula (I), or an isotopic variant thereof; or a pharmaceutically acceptable salt, solvate, hydrate, or prodrug thereof is administered over a period of 35 days. In some embodiments, the compound of Formula (I), or an isotopic variant thereof; or a pharmaceutically acceptable salt, solvate, hydrate, or prodrug thereof is administered over a period of 36 days. In some embodiments, the compound of Formula (I), or an isotopic variant thereof; or a pharmaceutically acceptable salt, solvate, hydrate, or prodrug thereof is administered over a period of 37 days. In some embodiments, the compound of Formula (I), or an isotopic variant thereof; or a pharmaceutically acceptable salt, solvate, hydrate, or prodrug thereof is administered over a period of 38 days. In some embodiments, the compound of Formula (I), or an isotopic variant thereof; or a pharmaceutically acceptable salt, solvate, hydrate, or prodrug thereof is administered over a period of 39 days. In some embodiments, the compound of Formula (I), or an isotopic variant thereof; or a pharmaceutically acceptable salt, solvate, hydrate, or prodrug thereof is administered over a period of 40 days. In some embodiments, the compound of Formula (I), or an isotopic variant thereof; or a pharmaceutically acceptable salt, solvate, hydrate, or prodrug thereof is administered over a period of 41 days. In some embodiments, the compound of Formula (I), or an isotopic variant thereof; or a pharmaceutically acceptable salt, solvate, hydrate, or prodrug thereof is administered over a period of 42 days or more.

In certain embodiments, the compound of Formula (I), or an isotopic variant thereof; or a pharmaceutically acceptable salt, solvate, hydrate, or prodrug thereof is administered in an amount of about 25 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 50 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 100 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 150 mg once daily for a period of up to at least about 14 days.

In certain embodiments, the compound of Formula (I), or an isotopic variant thereof; or a pharmaceutically acceptable salt, solvate, hydrate, or prodrug thereof is administered in an amount of about 50 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 100 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 150 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 200 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 210 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 220 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 230 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 240 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 250 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 260 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 270 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 140 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 290 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 300 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 310 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 320 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 330 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 340 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 350 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 360 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 370 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 380 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 390 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 400 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 450 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 500 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 600 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 700 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 800 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 900 mg once daily for a period of up to at least about 14 days. In certain embodiments, the compound of Formula (I), or an isotopic variant thereof; or a pharmaceutically acceptable salt, solvate, hydrate, or prodrug thereof is administered in an amount of about 1000 mg once daily for a period of up to at least about 14 days.

In certain embodiments, the compound of Formula (I), or an isotopic variant thereof; or a pharmaceutically acceptable salt, solvate, hydrate, or prodrug thereof is administered in an amount of about 5 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 10 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 15 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 20 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 25 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 50 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 100 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 150 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 200 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 210 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 220 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 230 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 240 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 250 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 260 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 270 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 140 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 290 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 300 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 310 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 320 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 330 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 340 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 350 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 360 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 370 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 380 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 390 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 400 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 450 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 500 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 600 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 700 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 800 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 900 mg twice daily for a period of up to at least about 14 days. In certain embodiments, the compound of Formula (I), or an isotopic variant thereof; or a pharmaceutically acceptable salt, solvate, hydrate, or prodrug thereof is administered in an amount of about 1000 mg twice daily for a period of up to at least about 14 days.

In certain embodiments, the compound of Formula (I), or an isotopic variant thereof; or a pharmaceutically acceptable salt, solvate, hydrate, or prodrug thereof is administered in an amount of about 5 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 10 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 15 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 20 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 25 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 50 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 100 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 150 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 200 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 210 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 220 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 230 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 240 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 250 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 260 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 270 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 280 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 290 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 300 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 310 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 320 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 330 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 340 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 350 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 360 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 370 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 380 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 390 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 400 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 450 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 500 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 600 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 700 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 800 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 900 mg once daily for a period of up to at least about 28 days. In certain embodiments, the compound of Formula (I), or an isotopic variant thereof; or a pharmaceutically acceptable salt, solvate, hydrate, or prodrug thereof is administered in an amount of about 1000 mg once daily for a period of up to at least about 28 days.

In certain embodiments, the compound of Formula (I), or an isotopic variant thereof; or a pharmaceutically acceptable salt, solvate, hydrate, or prodrug thereof is administered in an amount of about 5 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 10 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 15 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 20 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 25 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 50 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 100 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 150 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 200 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 210 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 220 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 230 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 240 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 250 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 260 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 270 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 280 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 290 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 300 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 310 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 320 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 330 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 340 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 350 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 360 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 370 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 380 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 390 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 400 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 450 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 500 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 600 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 700 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 800 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 900 mg twice daily for a period of up to at least about 28 days. In certain embodiments, the compound of Formula (I), or an isotopic variant thereof; or a pharmaceutically acceptable salt, solvate, hydrate, or prodrug thereof is administered in an amount of about 1000 mg twice daily for a period of up to at least about 28 days.

In certain embodiments, the compound of Formula (I), or an isotopic variant thereof; or a pharmaceutically acceptable salt, solvate, hydrate, or prodrug thereof is administered in an amount of about 255 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 10 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 15 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 20 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 25 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 50 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 100 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 150 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 200 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 210 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 220 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 230 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 240 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 250 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 260 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 270 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 420 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 290 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 300 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 310 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 320 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 330 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 340 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 350 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 360 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 370 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 380 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 390 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 400 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 450 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 500 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 600 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 700 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 800 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 900 mg once daily for a period of up to at least about 42 days. In certain embodiments, the compound of Formula (I), or an isotopic variant thereof; or a pharmaceutically acceptable salt, solvate, hydrate, or prodrug thereof is administered in an amount of about 1000 mg once daily for a period of up to at least about 42 days.

In certain embodiments, the compound of Formula (I), or an isotopic variant thereof; or a pharmaceutically acceptable salt, solvate, hydrate, or prodrug thereof is administered in an amount of about 5 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 10 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 15 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 20 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 25 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 50 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 100 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 150 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 200 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 210 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 220 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 230 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 240 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 250 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 260 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 270 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 420 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 290 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 300 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 310 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 320 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 330 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 340 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 350 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 360 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 370 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 380 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 390 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 400 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 450 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 500 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 600 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 700 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 800 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 900 mg twice daily for a period of up to at least about 42 days. In certain embodiments, the compound of Formula (I), or an isotopic variant thereof; or a pharmaceutically acceptable salt, solvate, hydrate, or prodrug thereof is administered in an amount of about 1000 mg twice daily for a period of up to at least about 42 days.

In some embodiments, about 5 mg, about 10 mg, about 15 mg, about 20 mg, about 25 mg, about 50 mg, about 75 mg, about 100 mg, about 150 mg, about 200 mg, about 250 mg, about 300 mg, about 350 mg, or about 400 mg of the compound of Formula (I), or an isotopic variant thereof; or a pharmaceutically acceptable salt, solvate, hydrate, or prodrug thereof is administered twice per day. In some embodiments, about 5 mg, about 10 mg, about 15 mg, about 20 mg, about 25 mg, about 50 mg, about 75 mg, about 100 mg, about 150 mg, about 200 mg, about 300 mg, about 400 mg, about 500 mg, about 600 mg, about 700 mg, or about 800 mg of the compound of Formula (I), or an isotopic variant thereof; or a pharmaceutically acceptable salt, solvate, hydrate, or prodrug thereof is administered at least once per day.

In certain embodiments, from about 5 mg to about 1000 mg of a compound of Formula (I), or a pharmaceutically acceptable salt thereof, is administered to the subject. In certain embodiments, from about 25 mg to about 1000 mg of a compound of Formula (I), or a pharmaceutically acceptable salt thereof, is administered to the subject. In certain embodiments, from about 5 mg to about 25 mg of a compound of Formula (I), or a pharmaceutically acceptable salt thereof, is administered to the subject. In certain embodiments, from about 10 mg to about 400 mg of a compound of Formula (I), or a pharmaceutically acceptable salt thereof, is administered to the subject. In certain embodiments, from about 100 mg to about 600 mg of a compound of Formula (I), or a pharmaceutically acceptable salt thereof, is administered to the subject.

In certain embodiments, the compound of Formula (I), or a pharmaceutically acceptable salt thereof, is administered orally.

In certain embodiments, the compound of Formula (I), or a pharmaceutically acceptable salt thereof, is formulated as a capsule or tablet.

In certain embodiments, from about 25 mg to about 1000 mg of a compound of Formula (I), or a pharmaceutically acceptable salt thereof, is administered to the subject.

In certain embodiments, the compound of Formula (I), or a pharmaceutically acceptable salt thereof, is administered at a dose of from about 5 mg/day to about 1000 mg/day is administered to the subject. In certain embodiments, the compound of Formula (I), or a pharmaceutically acceptable salt thereof, is administered at a dose of from about 25 mg/day to about 1000 mg/day is administered to the subject. In certain embodiments, the compound of Formula (I), or a pharmaceutically acceptable salt thereof, is administered at a dose of from about 5 mg/day to about 25 mg/day is administered to the subject. In certain embodiments, the compound of Formula (I), or a pharmaceutically acceptable salt thereof, is administered at a dose of from about 10 mg/day to about 400 mg/day is administered to the subject. In certain embodiments, the compound of Formula (I), or a pharmaceutically acceptable salt thereof, is administered at a dose of from about 100 mg/day to about 600 mg/day.

In certain embodiments, the compound of Formula (I), or a pharmaceutically acceptable salt thereof, is administered in the fed state. In certain embodiments, the compound of Formula (I), or a pharmaceutically acceptable salt thereof, is administered in the fasted state. In certain embodiments, the compound of Formula (I), or a pharmaceutically acceptable salt thereof, is administered at least once per day.

In certain embodiments, the compound of Formula (I), or a pharmaceutically acceptable salt thereof, is administered at bedtime. In certain embodiments, the compound of Formula (I), or a pharmaceutically acceptable salt thereof, is administered less than about 6 hours before sleep. In certain embodiments, the compound of Formula (I), or a pharmaceutically acceptable salt thereof, is administered less than about 5 hours before sleep. In certain embodiments, the compound of Formula (I), or a pharmaceutically acceptable salt thereof, is administered less than about 4 hours before sleep. In certain embodiments, the compound of Formula (I), or a pharmaceutically acceptable salt thereof, is administered less than about 3 hours before sleep. In certain embodiments, the compound of Formula (I), or a pharmaceutically acceptable salt thereof, is administered less than about 2 hours before sleep. In certain embodiments, the compound of Formula (I), or a pharmaceutically acceptable salt thereof, is administered less than about 1 hour before sleep. In certain embodiments, the compound of Formula (I), or a pharmaceutically acceptable salt thereof, is administered less than about 30 minutes before sleep.

In certain embodiments, the compound of Formula (I), or a pharmaceutically acceptable salt thereof, is administered in the evening. In certain embodiments, the compound of Formula (I), or a pharmaceutically acceptable salt thereof, is administered at about 10 pm at night.

In another aspect is provided a method of treating or preventing testicular adrenal rest tumors (TART) or ovarian adrenal rest tumors (OART), comprising administering to a subject in need thereof a pharmaceutical composition, comprising a compound of structural Formula (I): and a pharmaceutically acceptable excipientcomprising with a compound as described herein, including embodiments, or the structural Formulae (I) and a pharmaceutically acceptable excipient:

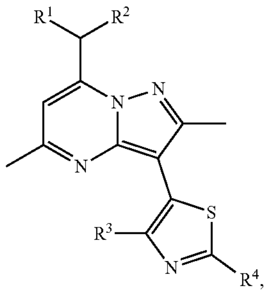

or a pharmaceutically acceptable salt thereof. $R^1$, $R^2$, $R^3$, and $R^4$ are as described herein, including embodiments.

In certain embodiments, the pharmaceutical composition comprises from about 25 mg to about 1000 mg of a compound of Formula (I), or a pharmaceutically acceptable salt thereof. In certain embodiments, the pharmaceutical composition comprises from about 25 mg to about 1000 mg of a compound of Formula (I), or a pharmaceutically acceptable salt thereof. In certain embodiments, the pharmaceutical composition comprises from about 5 mg to about 25 mg of a compound of Formula (I), or a pharmaceutically acceptable salt thereof. In certain embodiments, the pharmaceutical composition comprises from about 10 mg to about 400 mg of a compound of Formula (I), or a pharmaceutically acceptable salt thereof. In certain embodiments, the pharmaceutical composition comprises from about 100 mg to about 600 mg of a compound of Formula (I), or a pharmaceutically acceptable salt thereof.

In certain embodiments, the pharmaceutical composition comprises about 25 mg, about 50 mg, about 100 mg, about 150 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg about 500 mg, or about 600 mg of a compound of Formula (I), or a pharmaceutically acceptable salt thereof.

In certain embodiments, the pharmaceutical composition is administered orally.

In certain embodiments, the pharmaceutical composition is formulated as a capsule or tablet. In certain embodiments, the capsule or tablet comprises about 5 mg, about 10 mg, about 15 mg, about 20 mg, about 25 mg, about 50 mg, about 100 mg, about 150 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, or about 400 mg of a compound of Formula (I), or a pharmaceutically acceptable salt thereof. In certain embodiments, the capsule or tablet comprises about 50 mg of a compound of Formula (I), or a pharmaceutically acceptable salt thereof. In certain embodiments, the capsule or tablet comprises about 200 mg of a compound of Formula (I), or a pharmaceutically acceptable salt thereof.

In certain embodiments, the pharmaceutical composition is administered at a dose of from about 5 mg to about 1000 mg of a compound of Formula (I), or a pharmaceutically acceptable salt thereof, is administered to the subject. In certain embodiments, the pharmaceutical composition is administered at a dose of from about 25 mg to about 1000 mg of a compound of Formula (I), or a pharmaceutically acceptable salt thereof, is administered to the subject. In certain embodiments, the pharmaceutical composition is administered at a dose of from about 5 mg to about 25 mg of a compound of Formula (I), or a pharmaceutically acceptable salt thereof, is administered to the subject. In certain embodiments, the pharmaceutical composition is administered at a dose of from about 10 mg to about 400 mg of a compound of Formula (I), or a pharmaceutically acceptable salt thereof, is administered to the subject.

In certain embodiments, the pharmaceutical composition is administered at a dose of from about 5 mg/day to about 1000 mg/day is administered to the subject. In certain embodiments, the pharmaceutical composition is administered at a dose of from about 25 mg/day to about 1000 mg/day is administered to the subject. In certain embodiments, the pharmaceutical composition is administered at a dose of from about 5 mg/day to about 25 mg/day is administered to the subject. In certain embodiments, the pharmaceutical composition is administered at a dose of from about 10 mg/day to about 400 mg/day is administered to the subject. In certain embodiments, the pharmaceutical composition is administered at a dose of from about 100 mg/day to about 600 mg/day.

In certain embodiments, the pharmaceutical composition is administered in the fed state. In certain embodiments, the pharmaceutical composition is administered in the fasted state. In certain embodiments, the pharmaceutical composition is administered at least once per day.

In certain embodiments, the pharmaceutical composition is administered at bedtime. In certain embodiments, the pharmaceutical composition is administered less than about 6 hours before sleep. In certain embodiments, the pharmaceutical composition is administered less than about 5 hours before sleep. In certain embodiments, the pharmaceutical composition is administered less than about 4 hours before sleep. In certain embodiments, the pharmaceutical composition is administered less than about 3 hours before sleep. In certain embodiments, the pharmaceutical composition is administered less than about 2 hours before sleep. In certain embodiments, the pharmaceutical composition is administered less than about 1 hour before sleep. In certain embodiments, the pharmaceutical composition is administered less than about 30 minutes before sleep.

In certain embodiments, the pharmaceutical composition is administered in the evening. In certain embodiments, the pharmaceutical composition is administered at about 10 pm at night.

In certain embodiments, the subject has congenital adrenal hyperplasia (CAH).

In certain embodiments, the size and/or number of the tumors is decreased or reduced. In certain embodiments, the size of the tumors is decreased or reduced. In certain embodiments, the size of the tumors is decreased or reduced.

In certain embodiments of the methods disclosed herein, the method further comprises administering to the subject an additional chemotherapeutic agent.

In certain embodiments, the the additional chemotherapeutic agent is a glucocorticoid, a mineralocorticoid, an ACAT1 inhibitor, or an anti-androgen. In certain embodiments, the glucocorticoid is beclomethasone, betamethasone, budesonide, cortisone, dexamethasone, hydrocortisone, methylprednisolone, prednisolone, prednisone, or triamcinolone. In certain embodiments, the mineralocorticoid is fludrocortisone. In certain embodiments, the additional chemotherapeutic agent is another $CRF_1$ antagonist. In certain embodiments, the $CRF_1$ antagonist is:

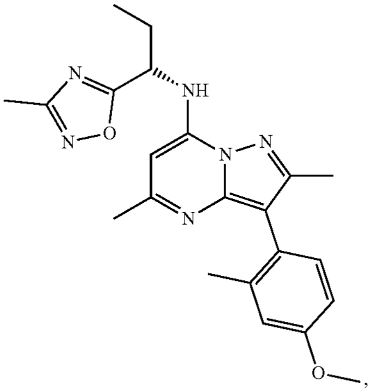

-continued

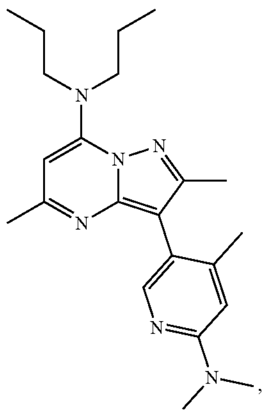

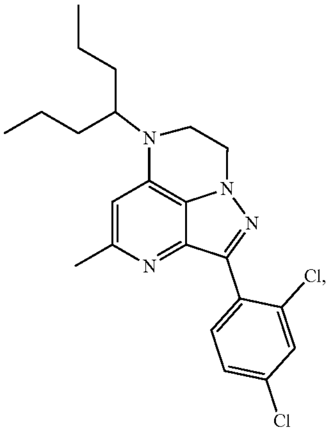

SSR-126374,

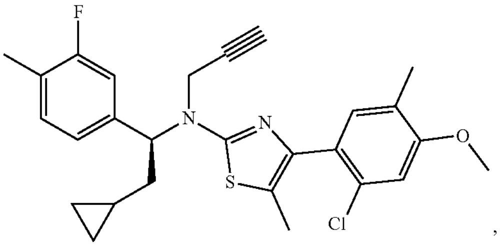

,

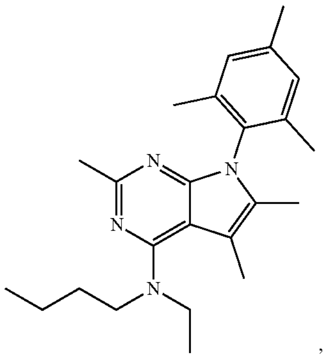

, or

-continued

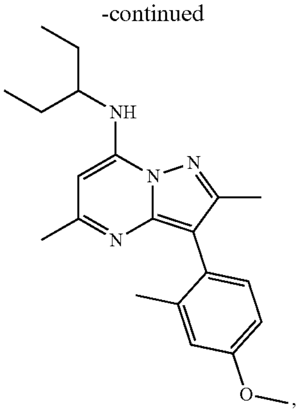

or a pharmaceutically acceptable salt thereof. In certain embodiments, the $CRF_1$ antagonist is

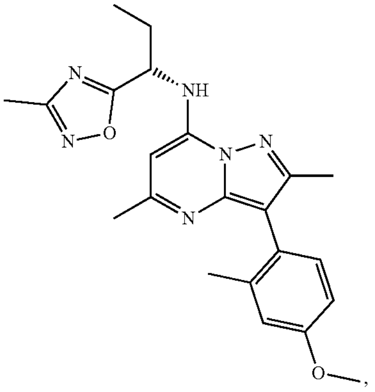

or a pharmaceutically acceptable salt thereof.

In certain embodiments of the methods disclosed herein, the method further comprises an additional treatment selected from surgical resection of the tumors and radiation therapy, or a combination thereof. In certain embodiments, the additional therapy is surgical resection and the surgical resection is prior to, after, and/or concurrent with administration of the compound of structural Formula (I), or a pharmaceutically acceptable salt thereof or the pharmaceutical composition, or any combination thereof. In certain embodiments, the surgical resection is prior to administration of the compound of structural Formula (I), or a pharmaceutically acceptable salt thereof or the pharmaceutical composition. In certain embodiments, the surgical resection is after administration of the compound of structural Formula (I), or a pharmaceutically acceptable salt thereof or the pharmaceutical composition. In certain embodiments, the surgical resection is concurrent with administration of the compound of structural Formula (I), or a pharmaceutically acceptable salt thereof or the pharmaceutical composition.

In certain embodiments, the additional treatment is radiation therapy and the radiation therapy is prior to, after, and/or concurrent with administration of the compound of structural Formula (I), or a pharmaceutically acceptable salt thereof or the pharmaceutical composition, or any combination thereof. In certain embodiments, the radiation therapy is prior to administration of the $CRF_1$ antagonist of structural Formula (I), or a pharmaceutically acceptable salt thereof or the pharmaceutical composition. In certain embodiments, the radiation therapy is after administration of the compound of structural Formula (I), or a pharmaceutically acceptable salt thereof or the pharmaceutical composition. In certain embodiments, the radiation therapy is concurrent with administration of the compound of structural Formula (I), or a pharmaceutically acceptable salt thereof or the pharmaceutical composition.

In one embodiment, the pharmaceutical compositions are provided in a dosage form for oral administration, which comprise a compound provided herein, and one or more pharmaceutically acceptable excipients or carriers. The pharmaceutical compositions provided herein that are formulated for oral administration may be in tablet, capsule, powder, or liquid form. In some embodiments, a tablet comprises a solid carrier or an adjuvant. Liquid pharmaceutical compositions generally comprise a liquid carrier such as water, petroleum, animal or vegetable oils, mineral oil, or synthetic oil. Physiological saline solution, dextrose or other saccharide solution, or glycols such as ethylene glycol, propylene glycol, or polyethylene glycol may be included. In some embodiments, a capsule comprises a solid carrier such as gelatin.

In another embodiment, the pharmaceutical compositions are provided in a dosage form for parenteral administration, which comprise a compound provided herein, and one or more pharmaceutically acceptable excipients or carriers. Where pharmaceutical compositions may be formulated for intravenous, cutaneous or subcutaneous injection, the active ingredient will be in the form of a parenterally acceptable aqueous solution, which is pyrogen-free and has a suitable pH, isotonicity, and stability. Those of relevant skill in the art are well able to prepare suitable solutions using, for example, isotonic vehicles, such as Sodium Chloride injection, Ringer's injection, or Lactated Ringer's injection. In some embodiments, preservatives, stabilisers, buffers, antioxidants, and/or other additives are included as required.

In yet another embodiment, the pharmaceutical compositions are provided in a dosage form for topical administration, which comprise a compound provided herein, and one or more pharmaceutically acceptable excipients or carriers.

The pharmaceutical compositions can also be formulated as modified release dosage forms, including delayed-, extended-, prolonged-, sustained-, pulsatile-, controlled-, accelerated-, fast-, targeted-, and programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology,* 2nd Edition, Rathbone et al., Eds., Marcel Dekker, Inc.: New York, NY, 2008).

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In certain embodiments, the pharmaceutical compositions provided herein further comprise one or more chemotherapeutic agents as defined herein.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, PA); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, MD) and CAB-O-SIL® (Cabot Co. of Boston, MA); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, MA), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, KS).

When the pharmaceutical compositions provided herein are formulated for multiple dosage administration, the multiple dosage parenteral formulations must contain an antimicrobial agent at bacteriostatic or fungi static concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and metliacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

V. Examples

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

Example 1. A Phase 2, Open-Label Study to Evaluate the Efficacy and Safety of Compound 1 in Subjects with Testicular Adrenal Rest Tumors Testicular adrenal rest tumors (TART) is a common complication in congenital adrenal hyperplasia (CAH) that is caused by adrenocorticotropin hormone (ACTH)-driven overstimulation of aberrant adrenal cells within the testes and results in impaired spermatogenesis and infertility. TARTS can be found anywhere on the testes, though a typical (very common) location is within the mediastinum. This is a particularly problematic location. Because of the central location of TARTs being in the mediastinum, compression of the nearby seminiferous tubules is common and can lead to obstructive azoospermia, irreversible damage to surrounding tissue, and permanent infertility in males.

Figure 12A:
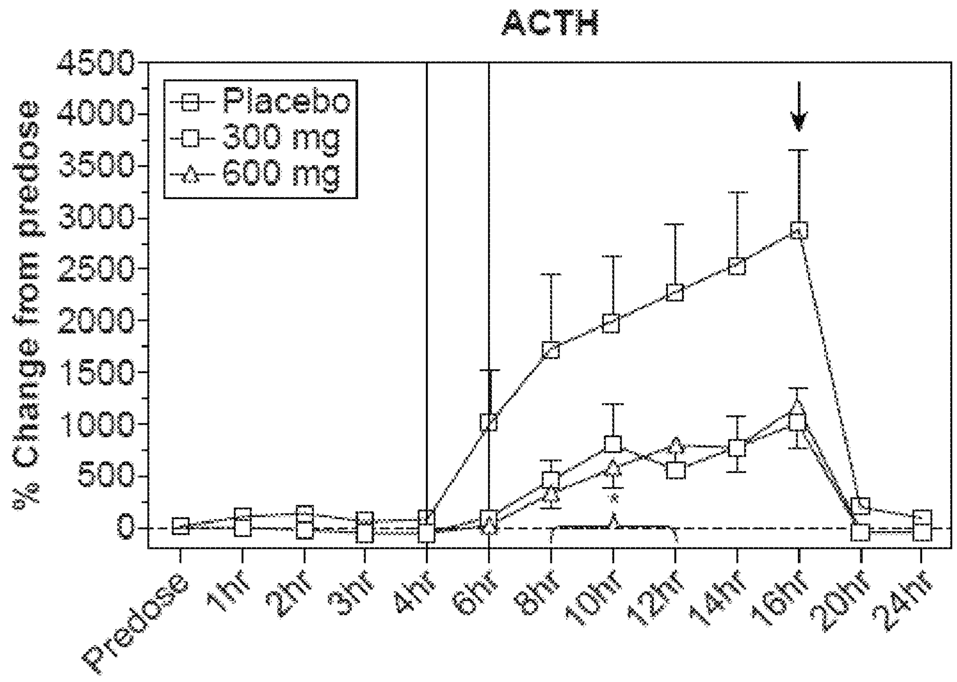
FIG. 12A-12B. Graphic representation of ACTH levels (A) and 17-OHP levels (B) after treatment with a $CRF_1$ antagonist.
Figure 12B:
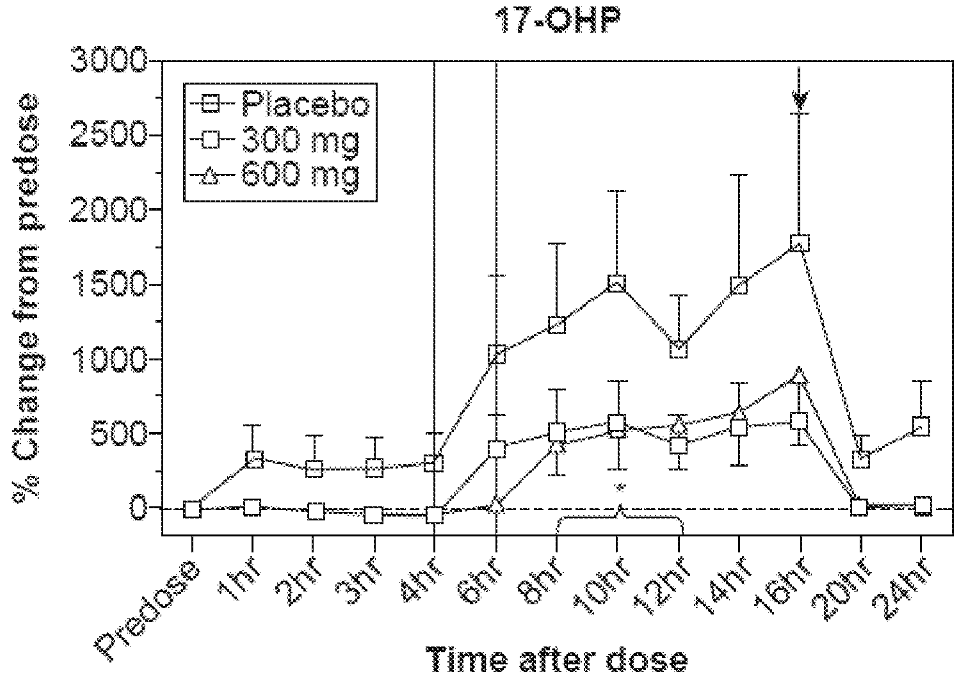

Current treatment for TART consists of chronic high-dose glucocorticoids, a problematic therapy with significant side effects and a narrow therapeutic window. Given the serious nature of TART and the limitations and risks of chronic steroid therapy, new treatment modalities are needed for patients with TART. Compound 1, a high-affinity and selective small-molecule antagonist of the corticotropin-releasing factor type-1 ($CRF_1$) receptor, may be effective in blocking ACTH synthesis, thereby reducing the size of testicular lesions in TART and reducing the need for chronic supraphysiologic doses of glucocorticoids. This mechanism of action has been validated in a previous proof-of-concept study using a similar small-molecule $CRF_1$ receptor antagonist, which produced dose-dependent reductions in ACTH and 17-hydroxyprogesterone (17-OHP) in subjects with CAH (FIG. 12A-12B). Compound 1 has been shown to have an acceptable safety and tolerability profile in nonclinical toxicology studies and in 2 completed Phase 1 clinical studies in healthy volunteers. These promising results provide a rationale for investigating the use of Compound 1 in the treatment of TART, in combination with replacement glucocorticoids and mineralocorticoids.

The structure of Compound 1 is.

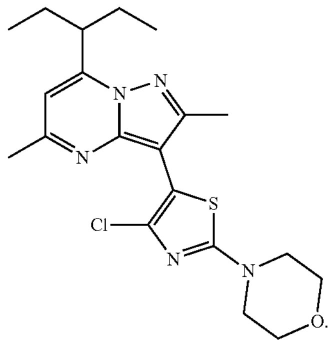 [SMILES: CCC(CC)c1cc(C)nc2c(-c3sc(N4CCOCC4)nc3Cl)c(C)nn12]

Building upon the 2 completed Phase 1 studies of Compound 1 in healthy volunteers and the ongoing Phase 2 proof-of-concept study of Compound 1 in subjects with CAH, this Phase 2 will study Compound 1 specifically in male CAH subjects with TART for the first time. A sample size of approximately 12 subjects was selected to provide sufficient data for an initial evaluation of efficacy and safety in subjects with TART while maintaining feasible subject recruitment goals for this rare condition. Given the rarity of the disease and thus the small sample size that can be recruited, this study will be open label, and all enrolled subjects will receive active study drug. Subjects will serve as their own controls in that their outcome measures after 12 weeks of study drug dosing will be compared to their baseline measures.

The schedule of study visits (every 2 weeks through Week 4, then every 4 weeks for the remainder of the study) provides an appropriate balance between minimizing subject burden and closely monitoring subject safety and response to therapy. The 4-week post-treatment washout period will allow for adequate safety follow-up and analysis of any HPA axis rebound after the last dose of study drug.

Figure 1B:
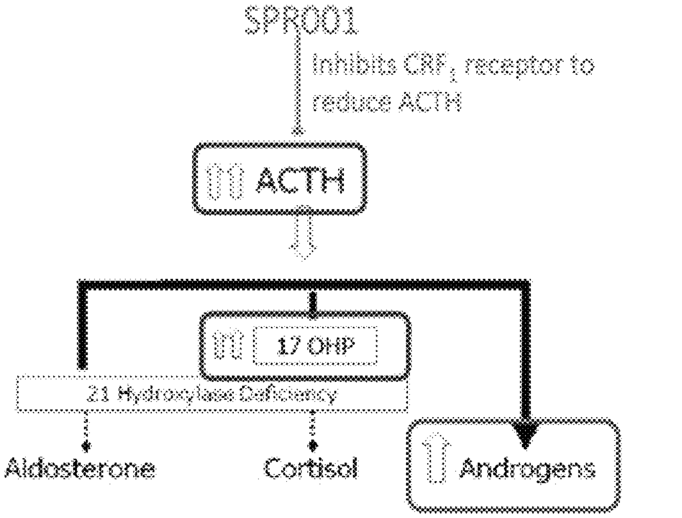

The specification of study drug dosing at 10 pm and after consumption of a snack is based on information from the Phase 1 studies in healthy volunteers. The plasma $C_{max}$ (maximum concentration) for Compound 1 in the Phase 1 studies occurred approximately 5 hours after dosing. Therefore, Compound 1 will be dosed daily at 10 pm in this study in order to achieve peak plasma study drug concentration at the time of day when most adrenal androgens are produced. Subjects will consume a standardized snack before taking study drug because the Phase 1 studies showed minimal study drug absorption when subjects were dosed in a fasted state. Specific dose reduction criteria, strict individual treatment stopping criteria, and appropriate laboratory and medical assessments have been established to ensure subject safety. (FIGS. 1A-1B).

| Objectives | Endpoints |
| --- | --- |
| Primary | |
| To assess the efficacy of Compound 1 in subjects with TART | Reduction in the size/volume of TART on testicular ultrasound from screening to Week 12 |
| Secondary | |
| To evaluate the safety of Compound 1 in subjects with TART | Adverse events (AEs), serious adverse events (SAEs), AEs leading to withdrawal, AEs of special interest (AESIs)<br>Physical examination findings<br>Vital signs<br>Changes in electrocardiogram (ECG)<br>Changes in clinical laboratory values |
| To assess the pharmacodynamic (PD) biomarker effects of Compound 1 | Changes in plasma concentrations of key PD biomarkers, including ACTH, 17-OHP, testosterone, androstenedione, luteinizing hormone (LH), follicle-stimulating hormone (FSH), inhibin B, sex hormone-binding globulin (SHBG), renin, and aldosterone from baseline to Week 12 |
| To assess changes on semen analysis | Changes in sperm count, morphology, and motility from baseline to Week 12 |
| To assess changes in metabolism | Changes in metabolic parameters, including fasting glucose, HbA1c, insulin sensitivity, and lipid profile (including LDL cholesterol, HDL cholesterol, and triglycerides), from baseline to Week 12<br>Changes in body weight, body mass index (BMI), waist circumference, and blood pressure |
| To evaluate changes in quality of life (QoL) and mood | Changes in QoL measured using the Short Form 36 (SF-36)<br>Changes in mood measured using the Hospital Anxiety and Depression Scale (HADS) |

Study Population

Approximately 12 male subjects with TART will be enrolled at approximately 6 investigative sites in the United States, United Kingdom, and possibly other countries. Up to 12 additional subjects may be added to further evaluate specific safety, PD, or efficacy findings.

Eligibility Criteria

Inclusion Criteria

- Adult male subjects aged 18 to 30, inclusive
- Documented historical diagnosis of CAH based on documented genetic mutation or historical documentation of elevated 17-OHP
- Diagnosis of TART via testicular ultrasound and/or magnetic resonance imaging (MRI) at screening with ≥1 lesion(s) measuring ≥2 cm in diameter
- On a stable regimen of GC replacement for ≥30 days before baseline
- Agree to follow contraception guidelines and refrain from donating sperm throughout the treatment period and for 90 days after the last dose of study drug
- Subject is able to understand all study procedures and risks involved and provides written informed consent indicating willingness to comply with all aspects of the protocol Exclusion Criteria

- Any clinically significant unstable medical condition, medically significant illness, or chronic disease within 30 days of screening, including but not limited to:
  - A malignancy or <3 years of remission history from any malignancy, other than successfully treated localized skin cancer
  - Presence of clinically significant renal disease, as evidenced by an estimated glomerular filtration rate (eGFR) of <60 mL/min/1.73 $m^2$
  - Current or chronic history of liver disease or known hepatic or biliary abnormalities (with the exception of Gilbert's syndrome or asymptomatic gallstones)
  - Confirmed positive test at screening for active hepatitis B, hepatitis C, or human immunodeficiency virus (HIV)
- Any clinically significant psychiatric disorders, including any current major depressive episode, bipolar disorder, schizophrenia, schizoaffective disorder, major depressive disorder with psychotic features, or any other psychotic disorder within the preceding 6 months
- HADS score >12 for either depression or anxiety
- At increased risk of suicide on the basis of the Investigator's judgment or the results of the Columbia-Suicide Severity Rating Scale (C-SSRS) conducted at screening and baseline (eg, C-SSRS Type 3, 4, or 5 ideation during the preceding 6 months or any suicidal behavior within the past 12 months)
- Clinically significant and abnormal clinical or laboratory assessments must be discussed with the Medical Monitor to determine eligibility for this study. Abnormal assessments that must be reviewed to determine eligibility include but are not limited to:
  - Clinically meaningful abnormal ECG results, in the opinion of the Investigator
  - Fridericia-corrected QT interval (QTcF) >450 msec
  - Alanine aminotransferase (ALT) >2× upper limit of normal (ULN)
  - Bilirubin >1.5×ULN (isolated bilirubin >1.5×ULN is acceptable if bilirubin is fractionated and direct bilirubin is <35%)
- A history that includes bilateral adrenalectomy or hypopituitarism
- Use of any other investigational drug within 30 days or 5 half-lives, whichever is longer, before initial screening
- Require use of prohibited concomitant medications, including strong inhibitors and/or inducers of CYP3A4

(with the exception of glucocorticoids, hydrocortisone, and dexamethasone) within 30 days or 5 half-lives (whichever is longer) of first dose of study drug. Medications that are sensitive substrates or substrates with narrow therapeutic ranges (metabolized by CYP3A4, 2C8, 2C9, or 2C19) should be discussed on a case-by-case basis with the Medical Monitor to determine whether the medication should be discontinued or may be continued with caution. If washout is feasible, then the medication should be withdrawn at least 30 days or 5 half-lives (whichever is longer) before the first dose of study drug.

Donation of blood within 60 days before first dose of study drug, or donation of platelets, white blood cells, or plasma within 15 days before first dose of study drug.

Study Duration

The expected duration of study participation for each subject is up to approximately 20 weeks. This includes a screening period of 54 weeks, a treatment period of 12 weeks, and a safety follow-up period of 4 weeks.

Study Design

This is a Phase 2, open-label efficacy and safety study of Compound 1 for the treatment of TART. All subjects will receive a daily oral dose of Compound 1 for 12 weeks. In-clinic study visits will occur for screening and at Day 1 (baseline) and Weeks 2, 4, 8, 12 (end of treatment), and 16 (follow-up).

Dose, Route, Regimen

All subjects will receive a daily oral dose of Compound 1 for 12 weeks. Subjects will receive 600 mg/day during the first 2 weeks and 1000 mg/day during the remaining 10 weeks of the treatment period. Study drug will be taken daily at 10 pm (or bedtime, if earlier), 5 to 15 minutes after consumption of a standardized snack.

On mornings of study visits with 8 am blood draws for laboratory assessments, subjects should take their morning glucocorticoid replacement after the blood draws. For all other days during the study, subjects may take their morning glucocorticoid replacement at their usual time (generally between 6 am and 8 am).

If a subject experiences a Grade 3 or higher TEAE considered at least possibly related to study drug, the Investigator may reduce the subject's daily dose of Compound 1 down in increments of 200 mg. Study drug will be discontinued in subjects who experience clinically significant liver chemistry, QTcF, or other individual treatment stopping criteria.

Investigational Drug

Compound 1 is a small-molecule $CRF_1$ receptor antagonist and will be supplied as 200-mg, size 1, white, hard gelatin capsules.

Example 2.

Since elevated ACTH is the primary driver for TART growth, blocking ACTH synthesis using Compound 1, a small-molecule antagonist of the $CRF_1$ receptor, may be effective in reducing ACTH levels, thereby reducing the size of testicular lesions in TART and reducing the need for chronic supraphysiologic doses of GCs. In CAH, this mechanism of action has been validated in a previous proof-of-concept study using a similar small-molecule $CRF_1$ receptor antagonist, which produced dose-dependent reductions in ACTH and 17-OHP in subjects with CAH (FIG. 12A-12B). The safety profile of Compound 1 has been established in nonclinical toxicology studies and in 2 completed Phase 1 clinical studies in healthy volunteers. A Phase 2 study in subjects with CAH is currently ongoing.

Nonclinical Toxicology of Compound 1

The nonclinical safety profile of Compound 1 has been evaluated in repeat-dose range-finding and definitive toxicology studies of up to 91 days in duration in rats and dogs using the clinically relevant route (oral) and schedule of administration (once daily). In rats and beagle dogs administered oral Compound 1 once daily for 91 consecutive days at doses up to 2000 mg/kg/day, toxicologic findings were all mild and limited to the male reproductive tract, and all Compound 1-related findings were reversible following a 6-week treatment-free recovery period.

Additionally, a fertility toxicology study was conducted in rats. In this study, male rats were administered oral Compound 1 once daily at 0, 5, 20, or 1000 mg/kg for 85 to 87 days (70 days before mating, during mating, and ≤4 days between mating and necropsy). Male reproductive performance (mean day of mating, mating and fertility indices, and conception rates) was unaffected by Compound 1 treatment. Untreated females mated with the Compound 1-treated males had no ovarian and uterine effects.

In addition, a complete battery of standard genotoxicity tests consisting of in vitro bacterial reverse mutation and chromosome aberration assays and an in vivo (rat) bone marrow micronucleus assay has been conducted. Exploratory and definitive embryo-fetal development studies in rabbits and a bovine corneal opacity and permeability assay have also been conducted.

Clinical Experience with Compound 1

To date, a total of 53 subjects, all healthy adults aged 21 to 65 years, have been treated with at least 1 dose of Compound 1 in 2 Phase 1 studies. The first-in-human study of Compound 1 (Study I3C-FW-BLAA) evaluated single ascending doses of 2 mg to 800 mg. In this study, a small number of subjects experienced diarrhea and headache of mild or moderate severity. A subsequent study (Study I3C-FW-BLAB) evaluated repeat doses of 50 mg, 100 mg, or 200 mg Compound 1 once daily for 14 consecutive days. A small number of subjects in the repeat-dose study experienced dyspnea, rhinorrhea, palpitations, and headache. The Phase 1 studies showed no clinically significant alterations in safety laboratory values, vital signs, or electrocardiograms (ECGs). Compound 1 has been well tolerated in healthy human subjects, with no SAEs, AEs leading to discontinuation, or dose-limiting toxicities (DLTs). A maximum tolerated dose has not been reached in humans.

Figure 2:
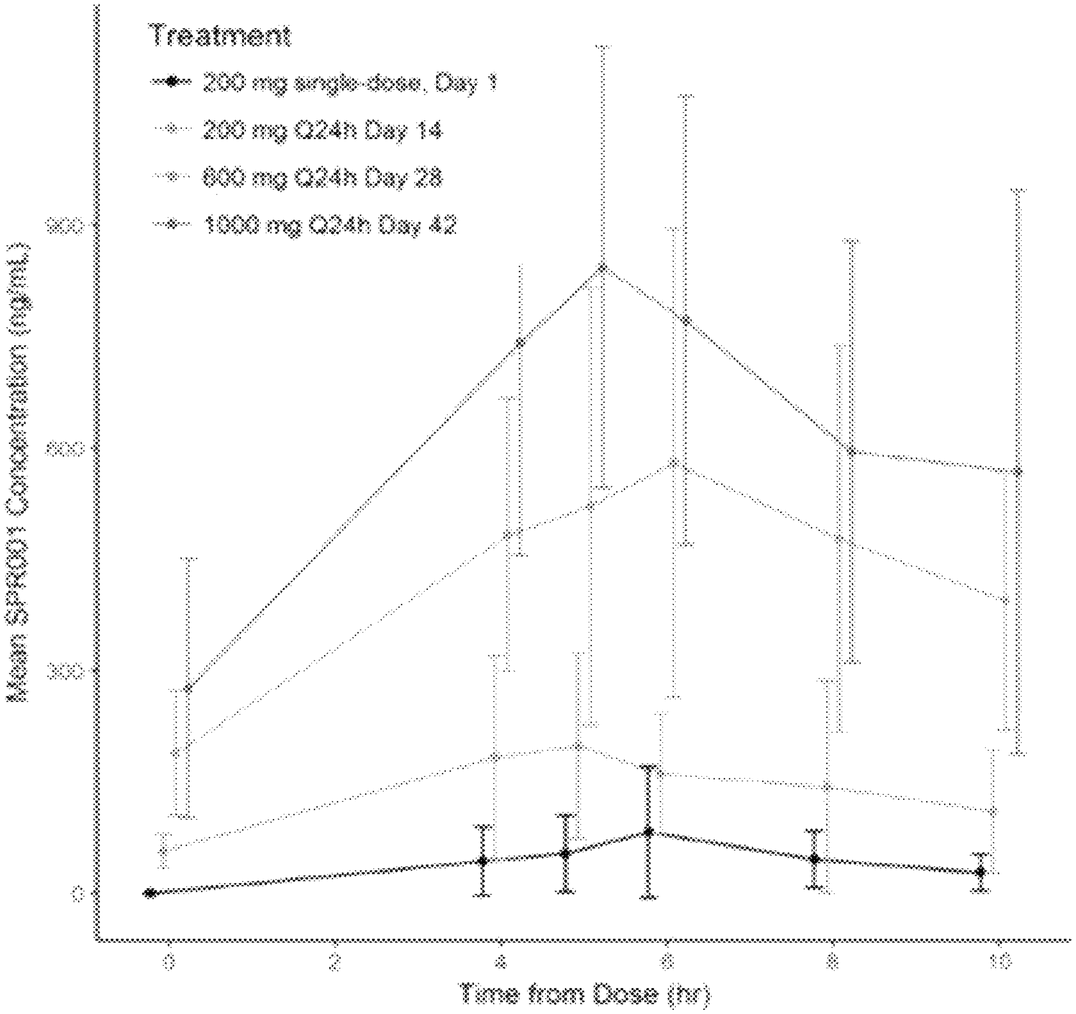
FIG. 2. Graphic representation of pharmacokinetics (dose-proportional, adequate exposure at safe doses) in patients with CAH following 14-days of once daily dosing at each dose level with a $CRF_1$ antagonist (Compound 1).
Figure 3:
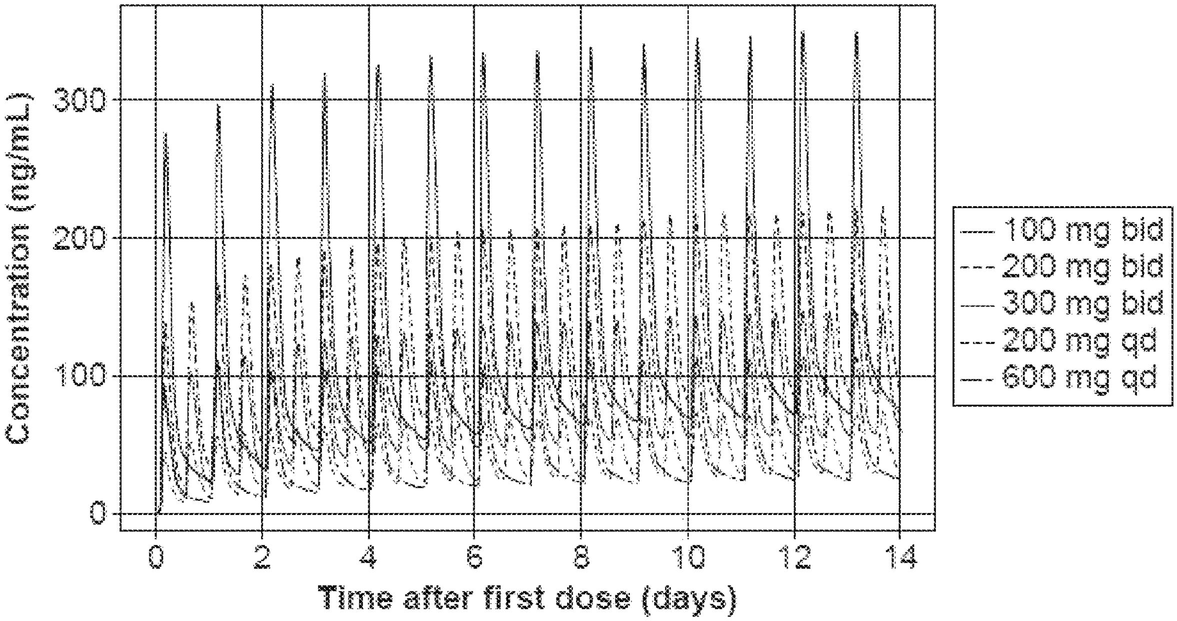
FIG. 3. Graphic representation of pharmacokinetics (dose-proportional, adequate exposure at safe doses) in patients with CAH following 14-days of once daily dosing at each dose level with a $CRF_1$ antagonist (Compound 1).

An ongoing Phase 2 open-label study (Study Compound 2) is currently evaluating the safety and efficacy of Compound 1 dosed once daily for 6 weeks in adults with classic CAH. In the initial Cohort A of this study, all subjects are dosed starting at 200 mg/day for 14 days, escalating for each subject to 600 mg/day for 14 days, then 1000 mg/day for 14 days if the subject experiences no DLTs at the previous dose level. (FIGS. 2-3).

Known Potential Risks

Because the reversible testicular effects (degeneration/atrophy) observed in rats and dogs treated with high-dose Compound 1 (2,000 mg/kg/day) are likely associated with on-target (mechanism-driven) effects, these effects are likely to be relevant to human risk. However, male reproductive studies in rodents showed no impairment in fertility at the highest dose tested (1,000 mg/kg/day). Additionally, there were no effects on clinical laboratory markers of testicular function (LH and FSH) when Compound 1 was administered to healthy male volunteers at doses up to 200 mg per day for 14 consecutive days. Clinical laboratory measures of testicular function (LH, FSH, inhibin B, and SHBG) will be assessed throughout this study to monitor the risk of testicular injury. Testicular ultrasounds and semen analysis will also be performed at screening/baseline and the end of the treatment period.

Laboratory abnormalities in liver function tests (LFTs) have been observed at significantly higher doses in nonclinical studies. However, these events were not observed in the Phase 1 clinical studies. Clinical laboratory measures of liver chemistry will be assessed throughout this study, and strict individual treatment stopping criteria for liver chemistry findings are in place.

Compound 1-induced effects on the thyroid gland were noted in dogs after 91 days of high-dose (2,000 mg/kg/day) treatment but not in any other nonclinical studies. Clinical pathology parameters of thyroid function (eg, T4, T3, thyroid-stimulating hormone [TSH]) were not evaluated in the Phase 1 studies but will be monitored throughout this study.

Known Potential Benefits

Early clinical studies suggests that Compound 1 is effective as a $CRF_1$ receptor antagonist, a mechanism of action that supports the clinical investigation of Compound 1 for treatment of TART. In CAH, this mechanism of action has been validated in a previous proof-of-concept study using a similar small-molecule $CRF_1$ receptor antagonist, which produced dose-dependent reductions in ACTH and 17-OHP in subjects with CAH (FIG. 12A-12B).

Assessment of Potential Risks and Benefits

The mild and reversible toxicologic effects of Compound 1 on the male reproductive tract in nonclinical studies occurred in the context of animals with normal, rather than elevated, baseline hormone function. As a $CRF_1$ receptor antagonist, Compound 1 is intended to reduce abnormally elevated ACTH levels, which in TART drives overstimulation of aberrant adrenal cells within the testes. In nonclinical models where baseline hormone levels are within normal ranges, clinical benefits are not expected, and indeed, toxicities may be expected as a result of androgen reduction outside of the normal range. In TART, where baseline ACTH and androgen levels are pathologically elevated, androgen reduction would be considered a positive, therapeutic effect.

Given the serious nature of TART and the limitations (and risks) of chronic steroid therapy, new treatment modalities are needed for patients with TART. Given the acceptable safety and tolerability profile of Compound 1 in healthy volunteers from the Phase 1 program, the low probability of demonstrating meaningful PD marker changes in healthy subjects, and the lack of any clear benefit to exposing more healthy subjects to study drug, the Sponsor believes the benefit-to-risk profile favors the entry of Compound 1 into Phase 2 in subjects with TART.

Example 3. Congenital Andrenal Hyperplasia (CAH)

CAH results from a genetic defect in the 21-hydroxylase enzyme. CAH patients are thus unable to produce cortisol. Without cortisol to provide negative feedback, patients over-produce ACTH. High ACTH promotes the overproduction of potent androgens (male sex hormones). Without wishing to be bound by theory, Compound 1 blocks $CRF_1$ receptor to prevent ACTH release by the pituitary and associated drive on the hypothalamic-pituitary-adrenal axis. Replacement of cortisol to physiological levels will correct cortisol deficiency, however, will not lower ACTH, resulting in hyperplasia of adrenal gland and associated overproduction of adrenal androgens.

Figure 4:
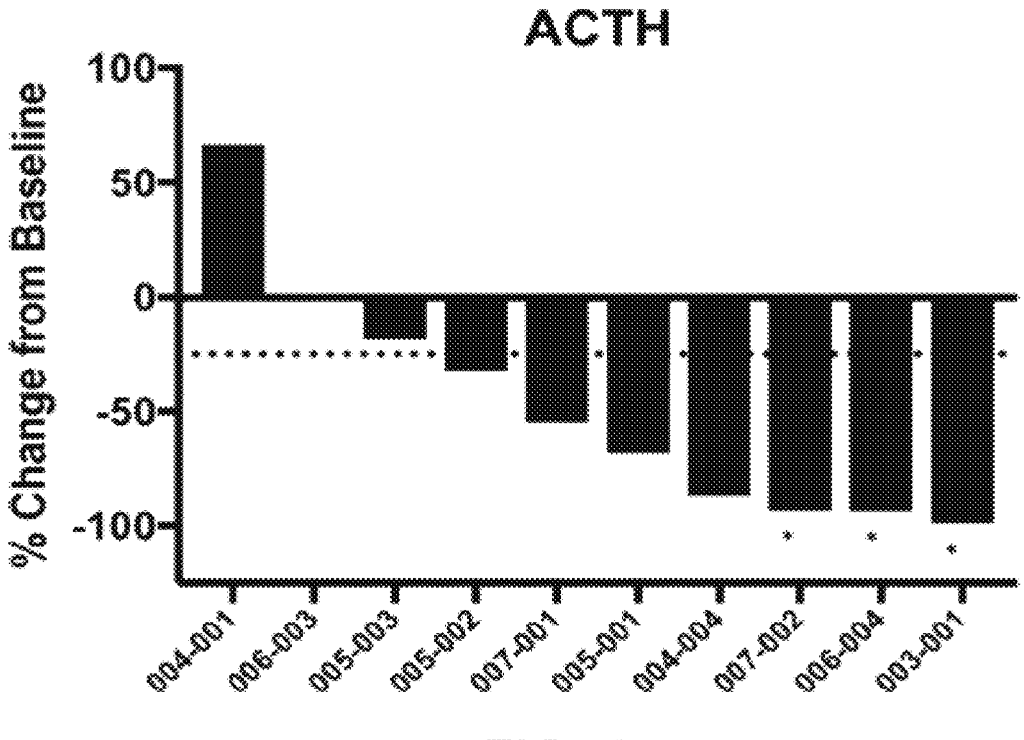
FIG. 4. Graphic representation of patient-level response (measuring ACTH levels) to a $CRF_1$ antagonist (Compound 1).
Figure 5A:
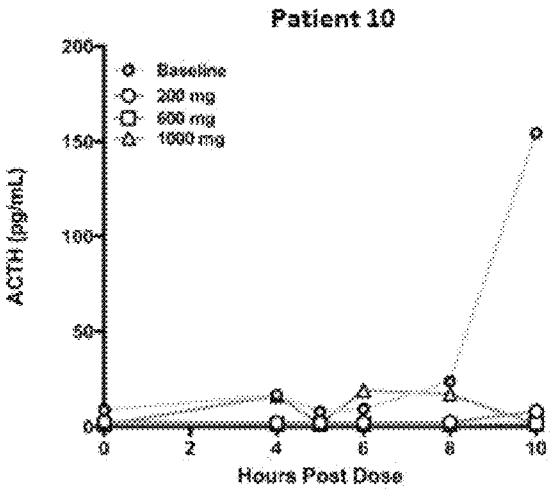
FIG. 5A-5B. Graphic representation of patient-level response of sample responders (measuring ACTH levels) to a $CRF_1$ antagonist [Patient 10 (A); Patient 8 (B)].
Figure 5B:
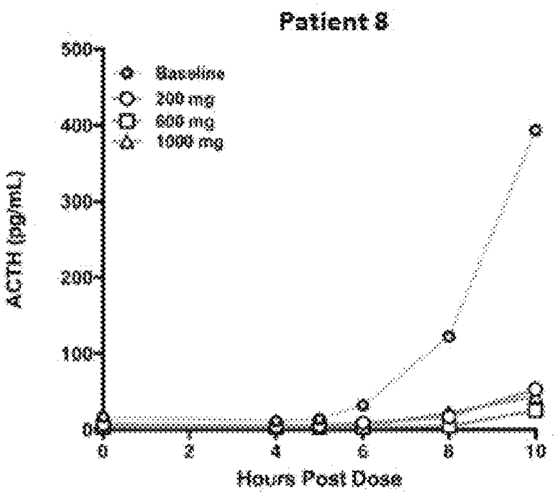

As shown in FIGS. 4 and 5A-5B, the attenuation of ACTH demonstrates target engagement and functional $CRF_1$ receptor antagonism. 80% of subjects demonstrated reduction in ACTH. 70% of subjects demonstrated >25% reduction in ACTH. 30% of subjects were in the normal range (*) after treatment with a $CRF_1$ receptor antagonist.

Figure 6:
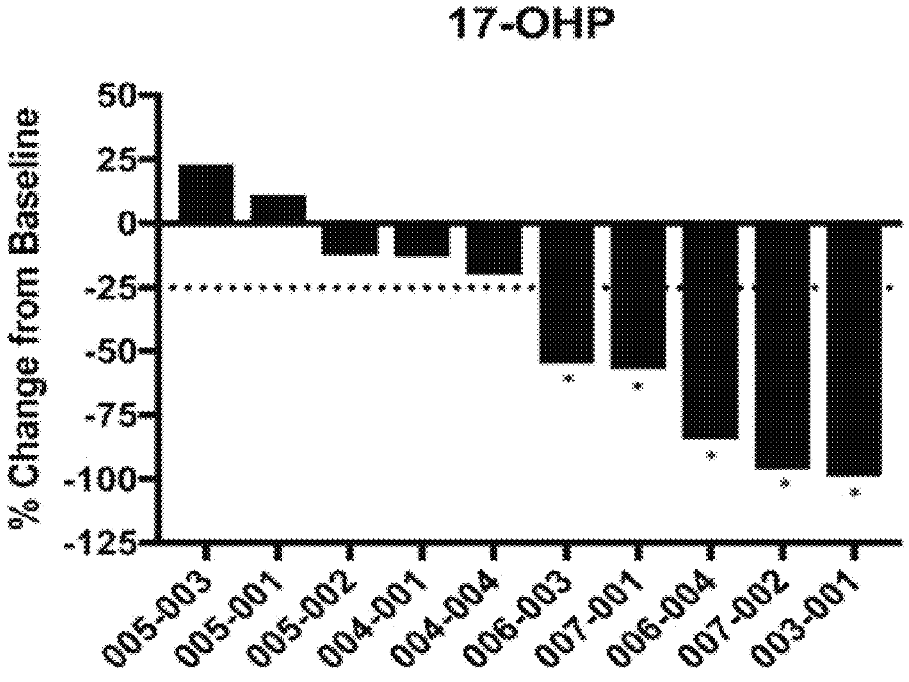
FIG. 6. Graphic representation of patient-level response (measuring 17-OHP levels) to a $CRF_1$ antagonist (Compound 1).
Figure 7A:
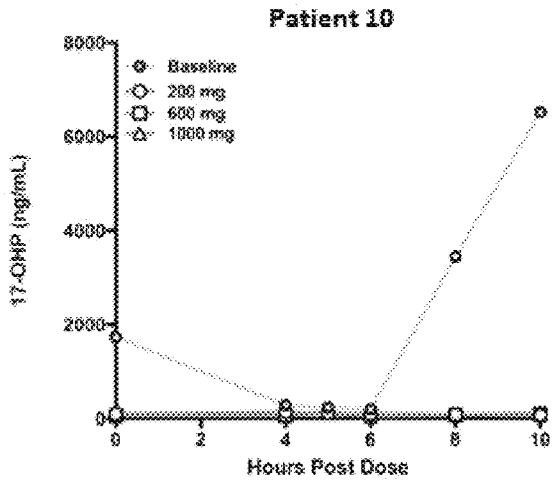
FIG. 7A-7B. Graphic representation of patient-level response of sample responders (measuring 17-OHP levels) to a $CRF_1$ antagonist [Patient 10 (A); Patient 8 (B)].
Figure 7B:
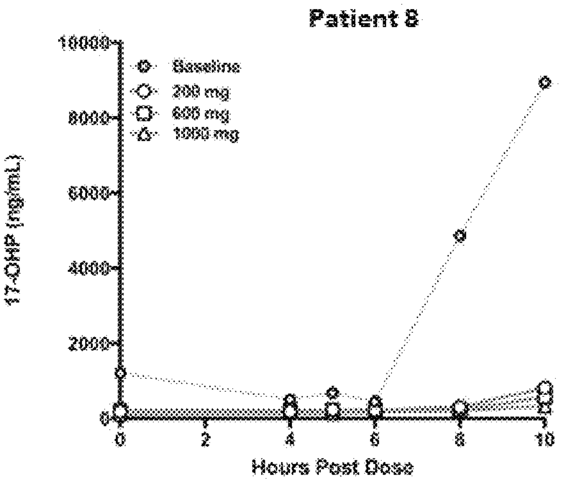

FIGS. 6 and 7A-7B demonstrate "control" of disease based on standard guidelines, which would then allow steroid taper. 80% of subjects demonstrated reduction in 17-OHP. 50% of subjects demonstrated >25% reduction in ACTH. 50% of subjects were in the guideline range (*; 1200 ng/dL) after treatment with a $CRF_1$ receptor antagonist.

Figure 8:
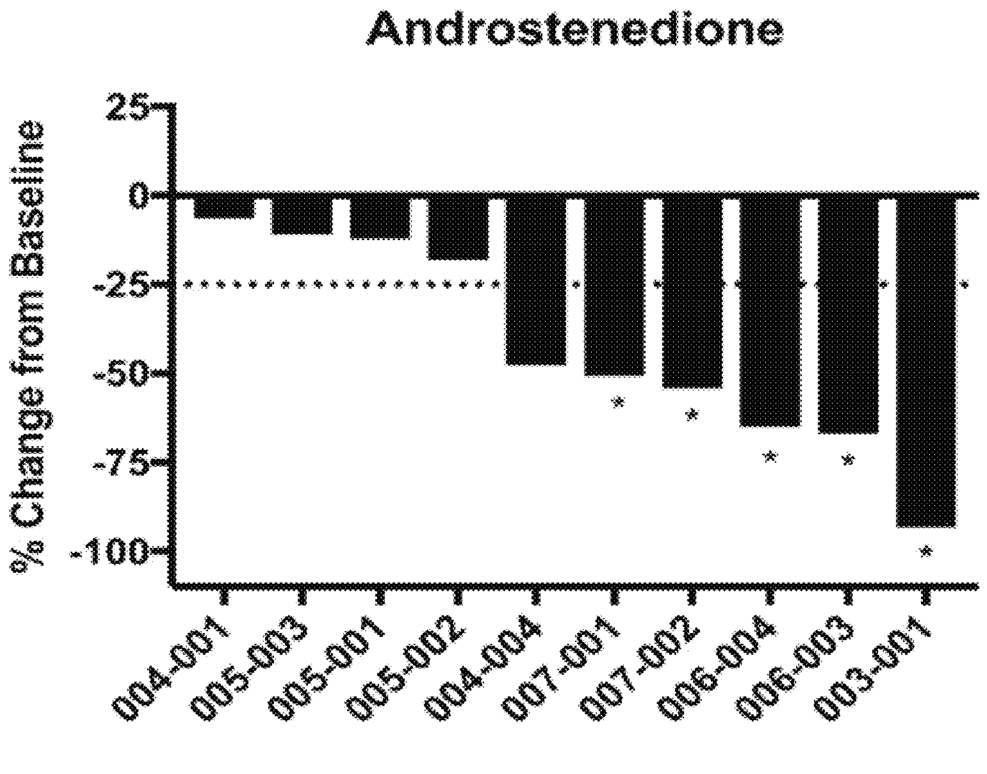
FIG. 8. Graphic representation of patient-level response (measuring androstenedione levels) to a $CRF_1$ antagonist (Compound 1).
Figure 9A:
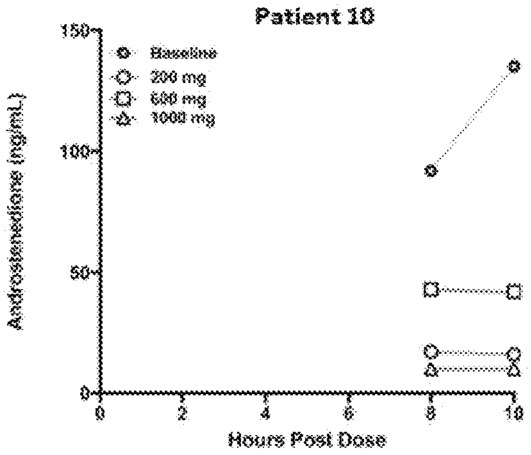
FIG. 9A-9B. Graphic representation of patient-level response of sample responders (measuring androstenedione levels) to a $CRF_1$ antagonist (Compound 1) [Patient 10 (A); Patient 8 (B)].
Figure 9B:
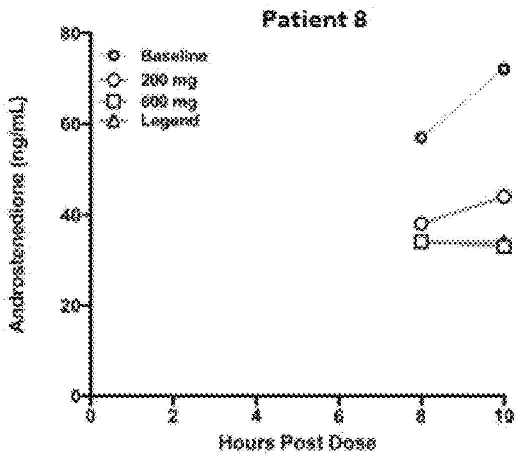

FIGS. 8 and 9A-9B demonstrate attenuation of morning rise in A4 upon treatment with a CRF1 antagonist, indicative of its ability to control excess androgen production and associated symptoms. 100% of subjects demonstrated reduction in androstenedione (at various doses). 60% of subjects demonstrated >25% reduction in androstenedione. 50% of subjects were within the normal reference range after treatment with a $CRF_1$ receptor antagonist.

Figure 10A:
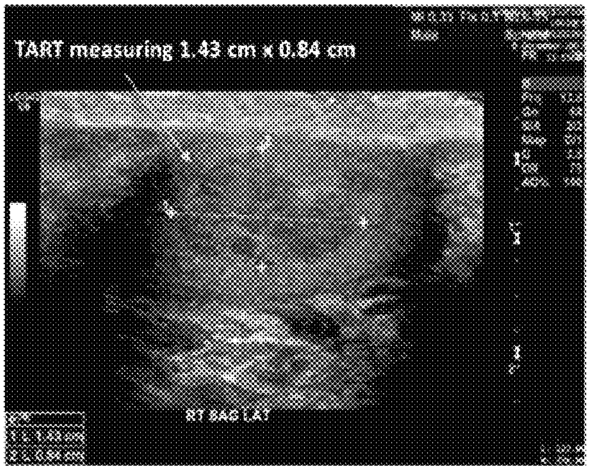
FIG. 10A-10B. Images of a patient with TART pre-treatment with a $CRF_1$ antagonist (Compound 1) (A) and 6-weeks post-treatment with a $CRF_1$ antagonist (Compound 1) (B).
Figure 10B:
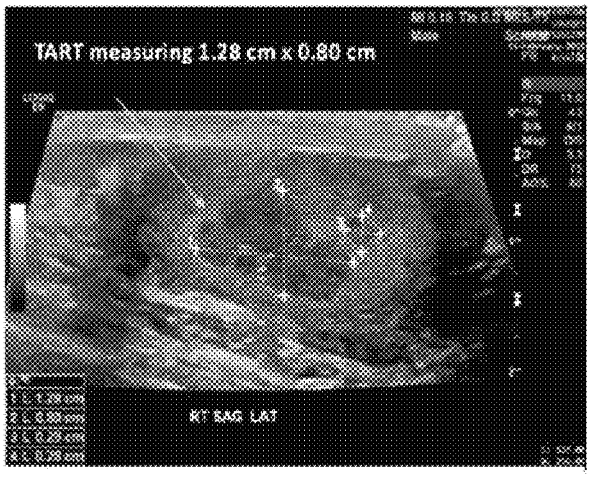

FIGS. 10A-10B show approximately 25% shrinkage in TART in a 25 year old male with classic congenital adrenal hyperplasia following 6 weeks treatment with a $CRF_1$ receptor antagonist.

Figure 11A:
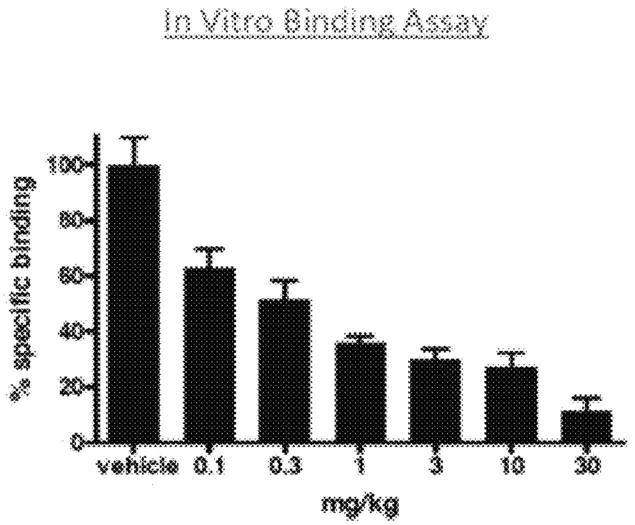
FIG. 11A-11B. Graphic representation of an in vitro binding assay of a $CRF_1$ antagonist (Compound 1); $^{125}$I-sauvagine binding to rat cerebellar membranes one hour after oral administration of increasing Compound 1 doses (A) and in vivo inhibition of CRF-induced activity after treatment with a $CRF_1$ antagonist; Compound 1 (oral, 10 mg/kg) (B).
Figure 11B:
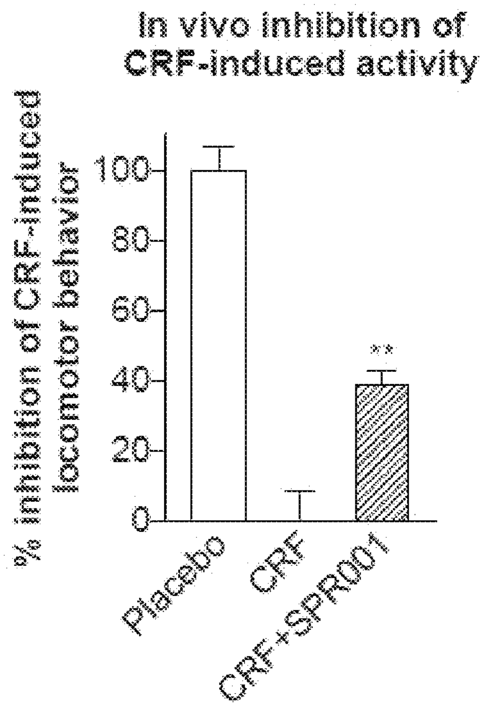

FIGS. 11A-11B demonstrate Compound 1 is a potent, selective, and functional $CRF_1$ receptor antagonist. In in vitro and ex vivo studies, Compound 1 was determined to be a potent and selective $CRF_1$ receptor antagonist with high affinity and selective for the $hCRF_1$ receptor. Compound 1 was found to have functional potency to inhibit adenylate cyclase activity ($CRF_1$ receptor-mediated downstream cascade), demonstrating in vitro efficacy as a $CRF_1$ receptor antagonist. Compound 1 was found to significantly inhibit CRF-induced locomotor behavior in response to i.e.v. administration of CRF (FIG. 11B).

FIGS. 12A-12B demonstrate single pill of $CRF_1$ receptor antagonist (i.e., as described in US 2017/0020877 A1) improves ACTH and 17-OHP in CAH patients.

Figure 13:
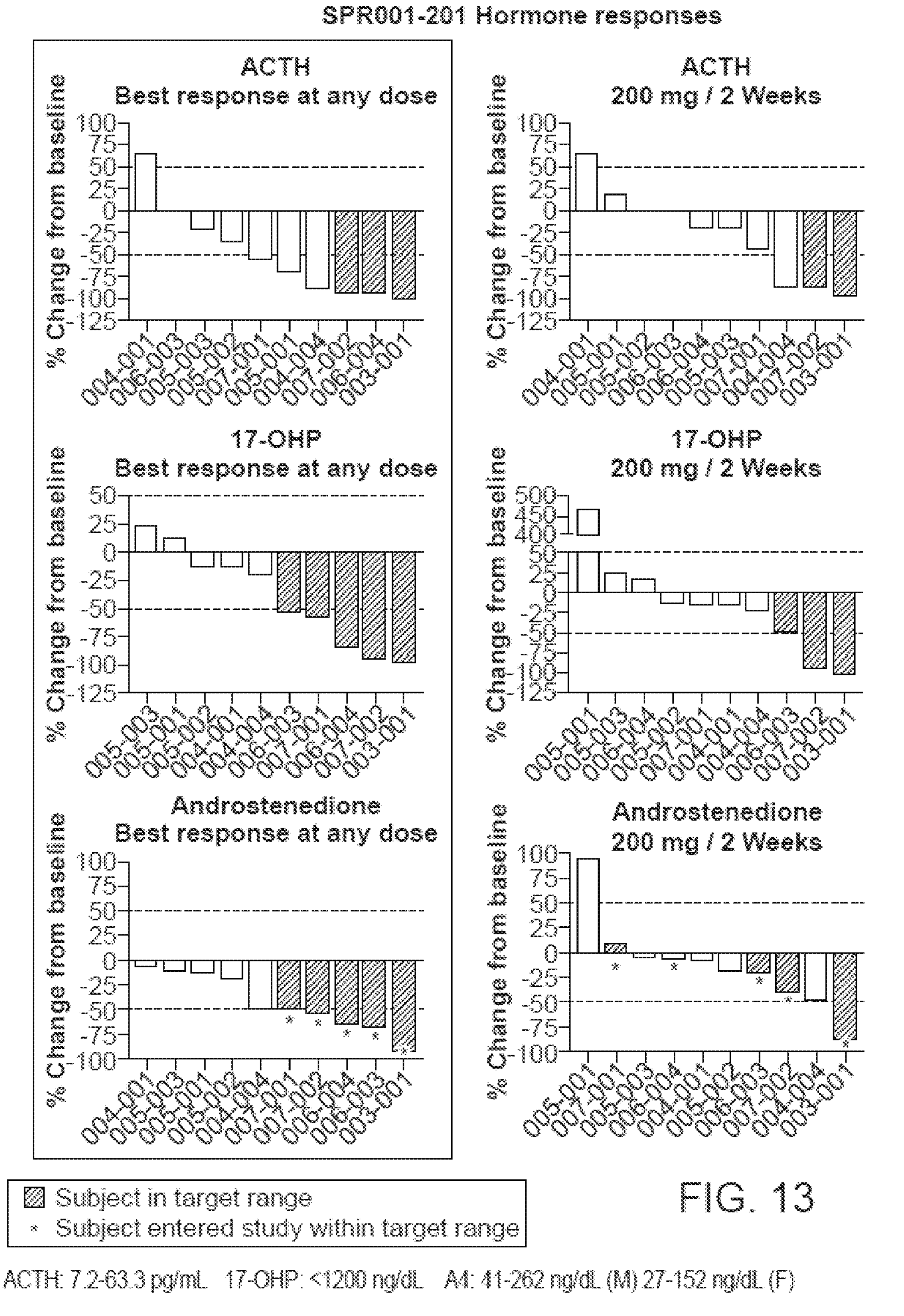
FIG. 13. Graphic representation of hormone responses after treatment with a $CRF_1$ antagonist (Compound 1).
Figure 13:
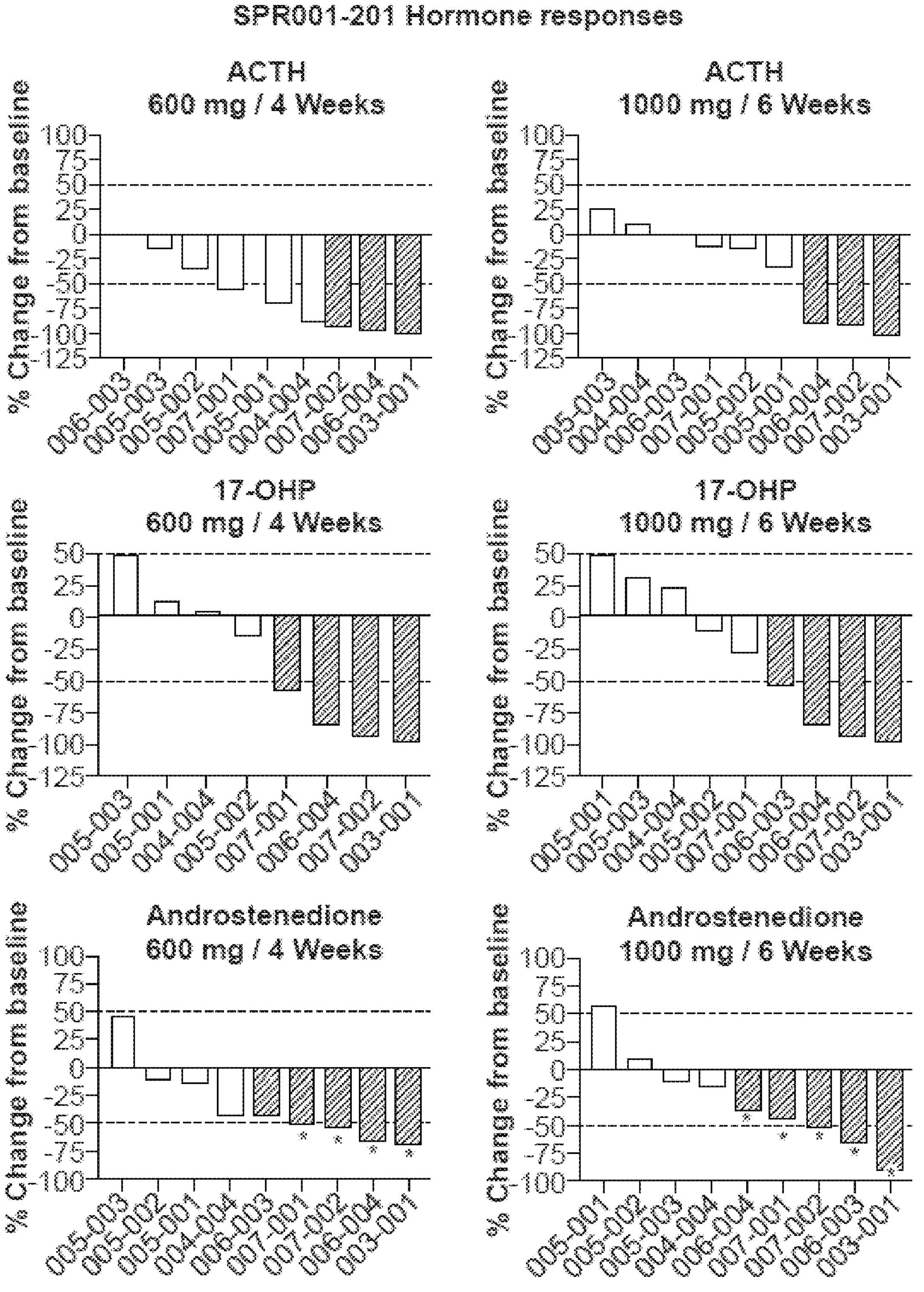

FIG. 13 shows the subject level hormone changes (ACTH, 17-OHP, and androstenedione) by dose of a $CRF_1$ receptor antagonist.

Example 4. Assess Reduction in Excess ACTH and Adrenal Steroid Production

The objectives of the study are: to assess the ability of Compound 1 to reduce excess ACTH and adrenal steroid production in participants with classic CAH on a stable glucocorticoid regimen; to evaluate the safety and tolerability of tildacerfont in participants with classic CAH; and to evaluate the pharmacokinetics (PK) of tildacerfont.

Eligibility Criteria

Figure 14:
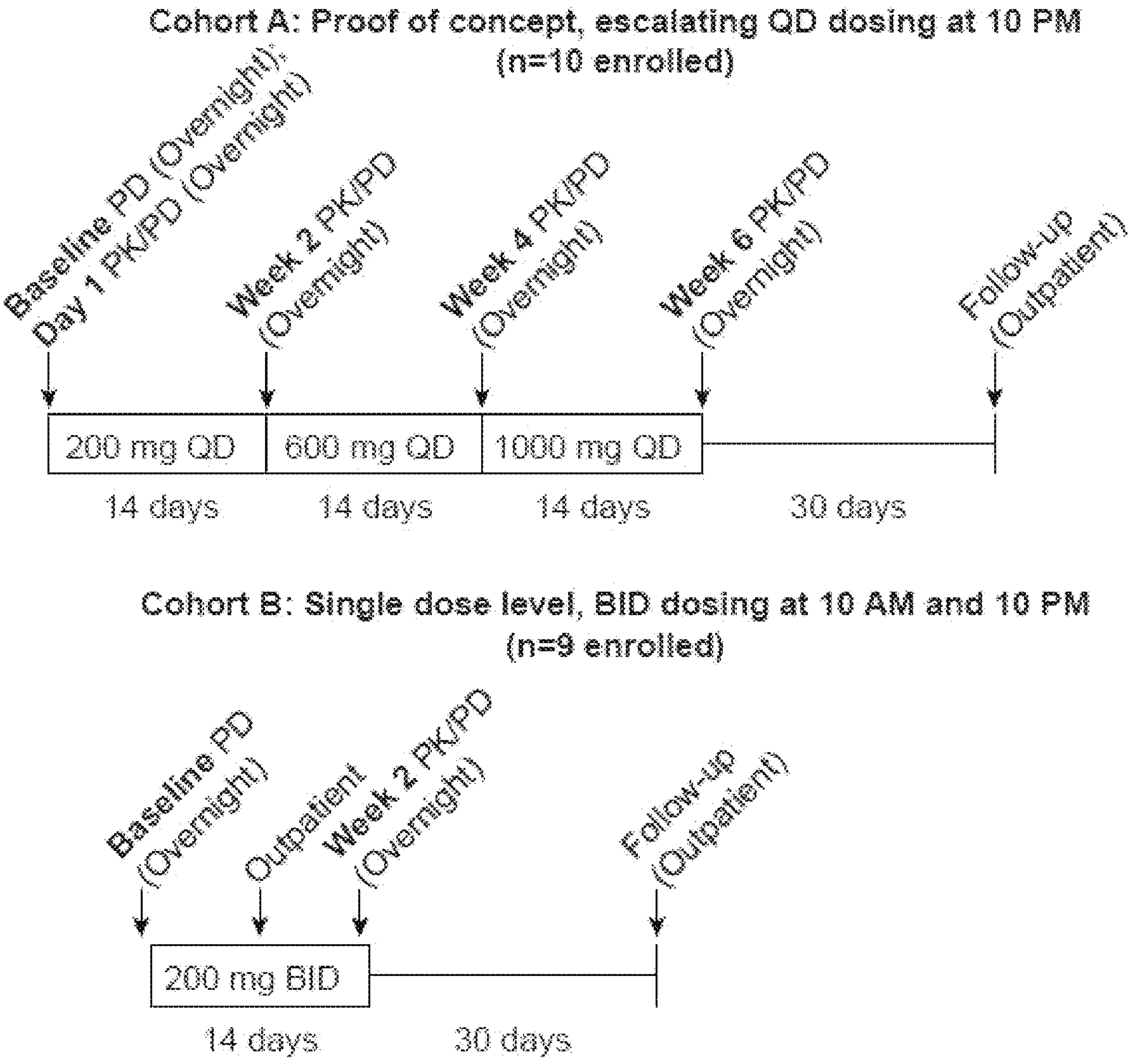
FIG. 14 depicts the proof of concept and escalating QD dosing at 10 pm for Cohort A and the single dose level and BID dosing at 10 am and 10 pm for Cohort B.
Figure 15A:
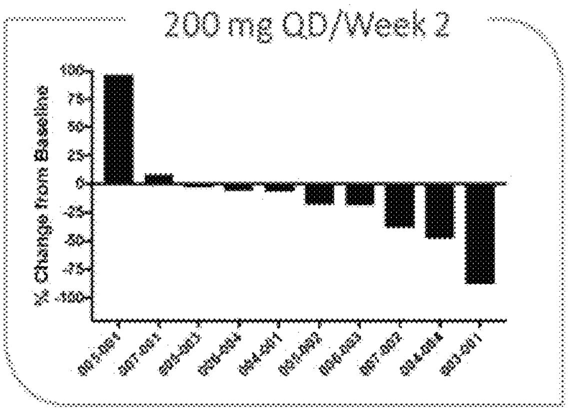
FIG. 15A-15D are graphic representations of changes in androstenedione seen in participants in Cohort A and Cohort B.
Figure 15B:
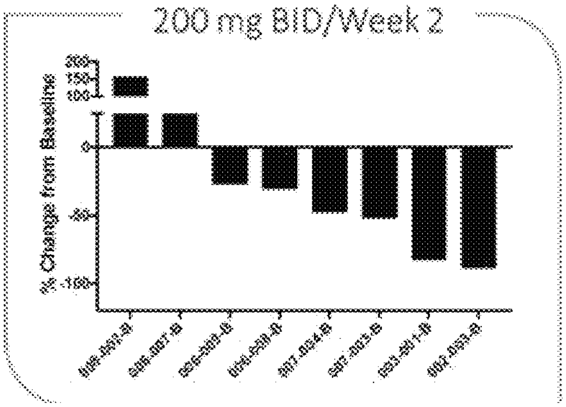
Figure 15C:
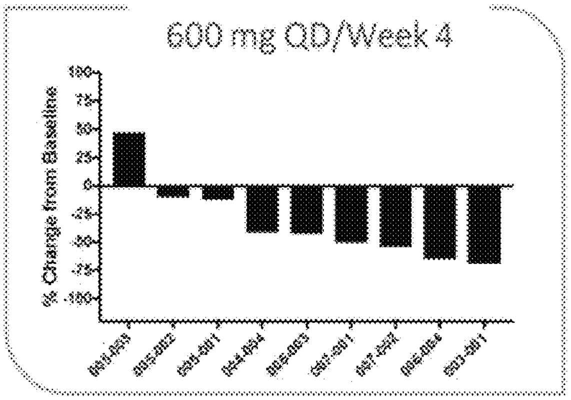
Figure 15D:
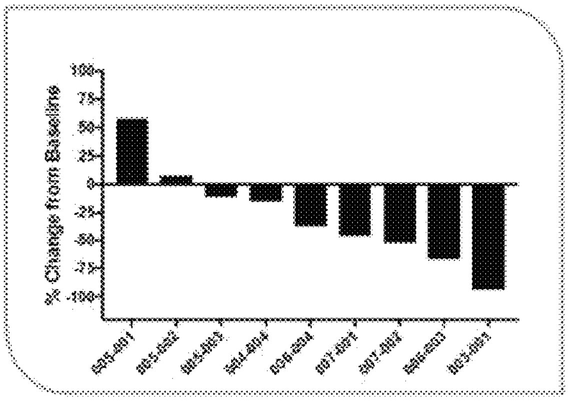
Figure 16A:
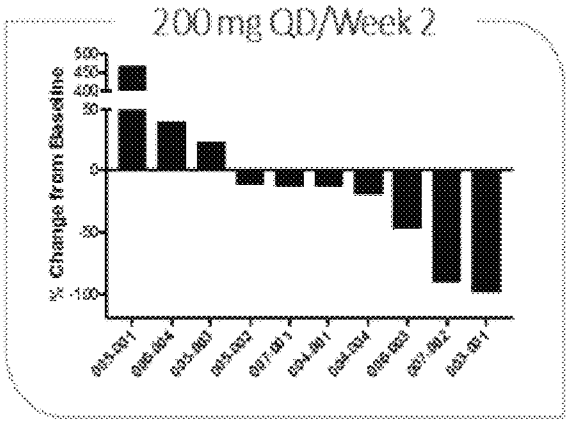
FIG. 16A-16D are graphic representations of changes in 17-hydroxyprogesterone seen in participants in Cohort A and Cohort B.
Figure 16B:
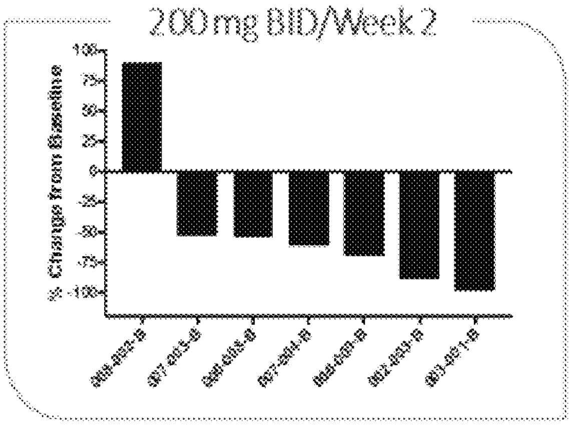
Figure 16C:
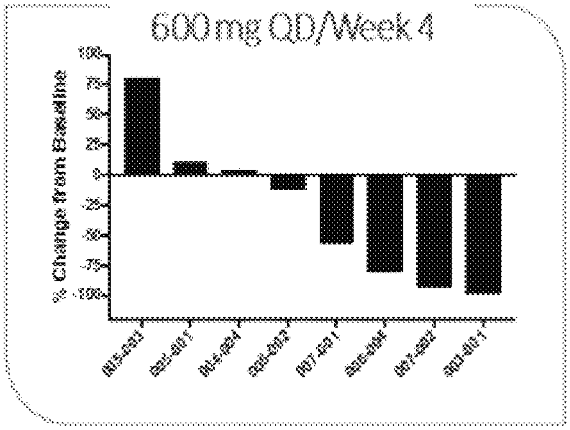
Figure 16D:
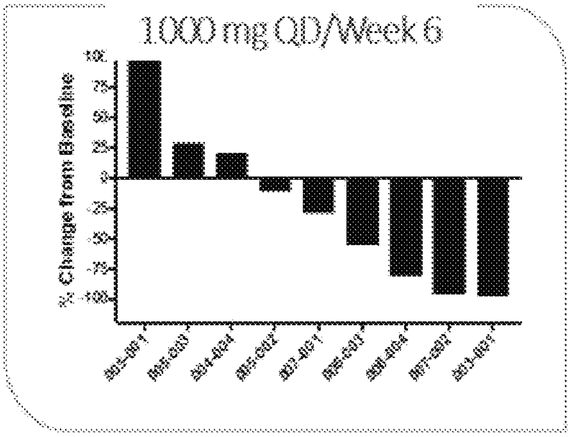
Figure 17A:
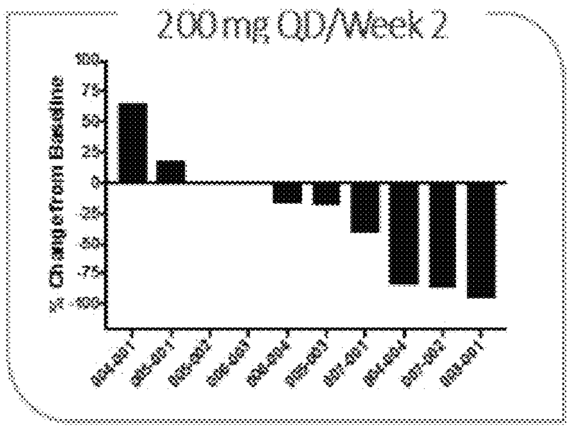
FIG. 17A-17D are graphic representations of changes in adrenocorticotropic hormone seen in participants in Cohort A and Cohort B.
Figure 17B:
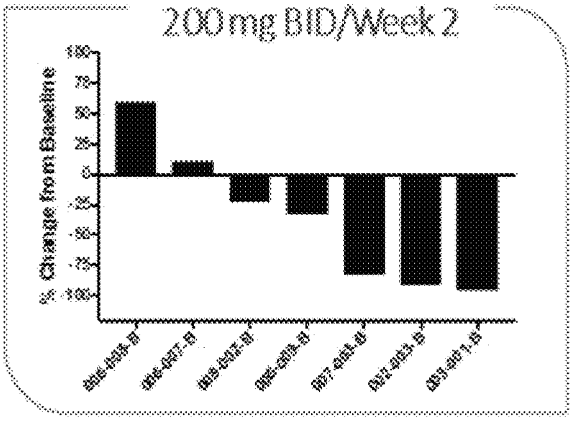
Figure 17C:
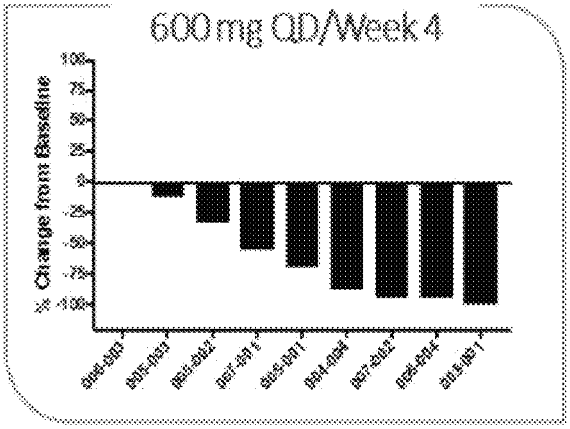
Figure 17D:
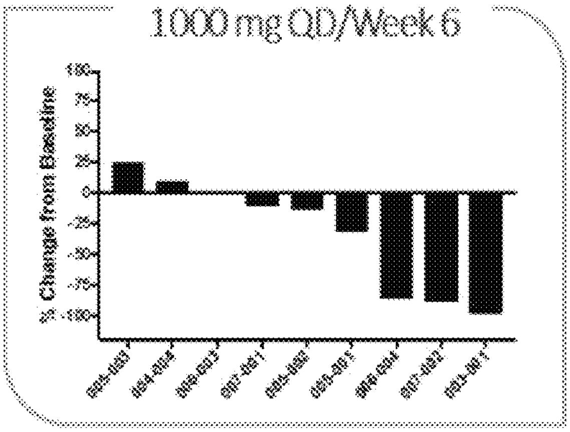

Inclusion Criteria:

- Adult males and females 18 years or older
- Diagnosis of classic CAH due to 21-hydroxylase deficiency
- Morning 17OHP ≥800 ng/dL, before taking any morning GC dose
- On a stable regimen of glucocorticoid replacement for ≥30 days before enrollment Exclusion Criteria:

- Clinically significant unstable medical condition, illness, or chronic disease within 30 days of screening
- Clinically significant psychiatric disorder
- History of bilateral adrenalectomy or hypopituitarism Study Design FIG. 14 depicts the proof of concept and escalating QD dosing at 10 PM for Cohort A and the single dose level and BID dosing at 10 AM and 10 pm for Cohort B.

Baseline Characteristics

Table 1 provides a description of the baseline characteristics displayed by Cohort A and Cohort B. In Cohort A, 10 partcipants were enrolled and received at least 1 dose of Compound 1. One participant withdrew early because of an occupation-related scheduling conflict. In Cohort B, 9 participants were enrolled and received at least one dose of Compound 1. One participant was withdrawn upon discovery of a major protocol violation at Baseline and did not have postbaseline efficacy/PK data. Thus, baseline characteristics are calculated for n=8 in Cohort B. One participant in Cohort B was taking both HC and prednisone.

TABLE 1

Baseline characteristics of each cohort

| Parameter | Cohort A (n = 10) | Cohort B (n = 8) |
|---|---|---|
| Demographics | | |
| Age (years), mean (range) | 39.3 (24-66) | 36.8 (19-66) |
| Sex | 5 M, 5 F | 1 M, 7 F |
| Bmi (kg/m$^2$), mean ± SD | 31.5 ± 12.0 | 31.1 ± 6.7 |
| Daily GC dose (mg HC equivalents), mean range | 28 (13-40) | 35 (20-50) |
| Types of GCs | 4 JC, 3 pred, 3 dex | 2 HC, 4 pred, 3 dex |
| 17OHP at screening[a] (ng/dl), mean ± SD | 5,985 ± 6,347 | 4,592 ± 4,624 |

Abbreviations:
17OHP: 17-hydroxyprogesterone;
BMI: body mass index;
dex: dexamethasone;
F: female;
GC: glucocorticoid;
HC: hydrocortisone;
M: male;
pred: prednisone;
SD: standard deviation.
[a]17OHP reference ranges: 27-199 ng/dL males, 15-290 ng/dL females.

Safety

Across both cohorts, Compound 1 was generally well tolerated. The most common type of adverse event (AE) was gastrointestinal disorders There were no serious AEs and no AEs leading to withdrawal.

Pharmacokinetics

Over a wide range of doses (200 to 1000 mg QD), Compound 1exhibited a predictable, dose-dependent PK profile.

Efficacy

FIG. 15A-15D show the changes in levels of Androstenedione (A4) across both cohorts. Levels of A4 improved at ≥1 dose level for 10 out of 10 participants in Cohort A and 6 out of 8 participants in Cohort B. Excess A4 is associated with clinical sequelae in CAH. Attenuation of A4 demonstrates control of adrenal androgen.

FIG. 16A-16D show the changes in levels of 17-hydroxyprogesterone (17-OHP) across both cohorts. Levels of 17OHP improved at 1 dose level for 8 out of 10 participants in Cohort A and 6 out of 7 participants in Cohort B. 17OHP is a critical hormone in CAH diagnosis and management. Attenuation of 17OHP demonstrates control of adrenal steroid production.

FIG. 17A-17D show the changes in levels of adrenocorticotropic hormone (ACTH) across both cohorts. Levels of ACTH improved at 1 dose level for 8 out of 10 participants in Cohort A and 5 out of 7 participants in Cohort B. Attenuation of ACTH demonstrates target engagement and fucntional CRF$_1$ receptor antagonism.

TABLE 2

Percentage change from baseline in ACTH, 17OHP and A4.

| | Cohort A | | | Cohort B |
|---|---|---|---|---|
| | 200 mg QD (Week 2) | 600 mg QD (Week 4) | 1000 mg QD (Week 6) | 200 mg BID (Weed 2) |
| ACTH | −25.7 (±51.6) | −60.1 (±37.5) | −32.7 (±47.0) | −36.5 (±58.0) |
| 17OHP | +22.2 (±172.3) | −23.7 (±64.2) | −13.8 (±74.7) | −47.8 (±63.3) |
| A4 | −12.1 (±47.4) | −33.2 (±36.5) | −28.6 (±44.6) | −16.0 (±81.4) |

CONCLUSIONS

Compound 1, a potent and selective CRF$_1$ receptor antagonist, offers a novel nonsteroidal oral treatment approach for CAH. Compound 1 was well tolerated and efficacious in reducing excess ACTH, 17OHP, and androstenedione in patients with classic CAH. Compound 1 exhibited a predictable, dose-dependent PK profile suitable for the target population.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of treating an endocrine disorder associated with corticotropin-releasing factor type-1 (CRF$_1$) activity, comprising administering to a subject in need thereof a small molecule CRF$_1$ antagonist, or a pharmaceutically acceptable salt thereof, wherein the small molecule CRF$_1$ antagonist is:

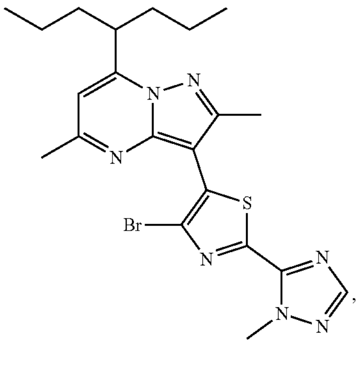
,

-continued
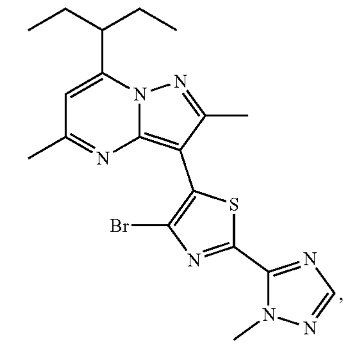
,
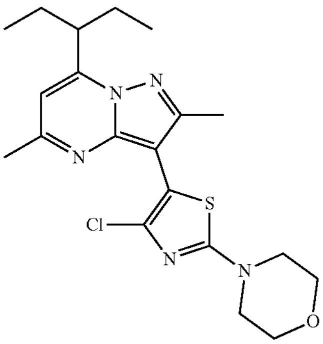
,
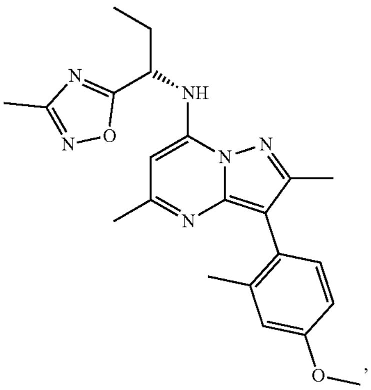
,
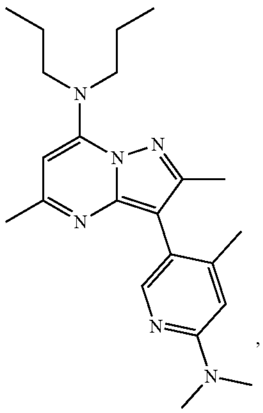
,
-continued
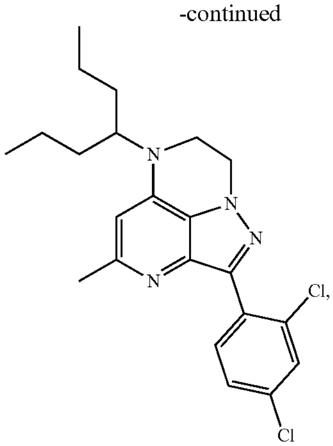
SSR-126374,
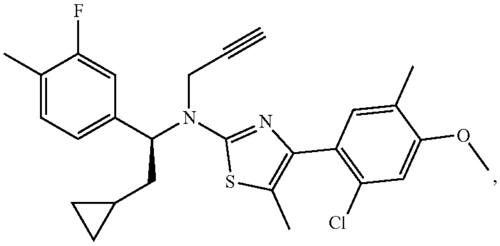
,
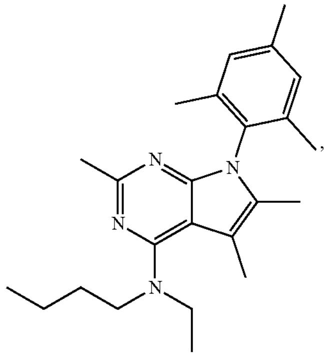
, or
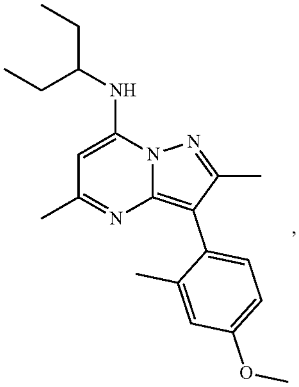
,
or a pharmaceutically acceptable salt thereof,
wherein the small molecule $CRF_1$ antagonist is administered to the subject twice per day, and
wherein the subject is in the fed state,
wherein the endocrine disorder associated with $CRF_1$ activity is a testicular adrenal rest tumor (TART) or an ovarian adrenal rest tumor (OART).

2. The method of claim 1, wherein the small molecule $CRF_1$ antagonist is:

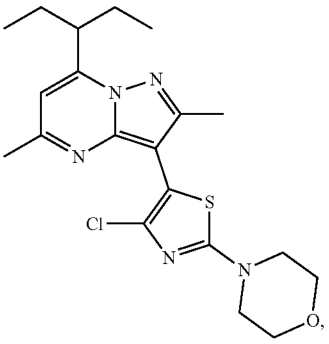 [SMILES: CCC(CC)c1cc(C)nc2c(-c3sc(N4CCOCC4)nc3Cl)c(C)nn12]

or a pharmaceutically acceptable salt thereof.

3. The method of claim 1, wherein the small molecule $CRF_1$ antagonist is:

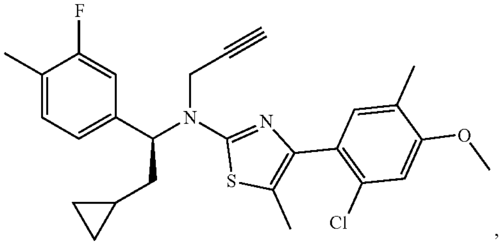

or a pharmaceutically acceptable salt thereof.

4. The method of claim 1, wherein the subject has congenital adrenal hyperplasia (CAH).

5. The method of claim 1, wherein the subject is receiving a glucocorticoid in conjunction with the administering of the small molecule $CRF_1$ antagonist.

6. The method of claim 5, wherein the glucocorticoid comprises beclomethasone, betamethasone, budesonide, cortisone, dexamethasone, hydrocortisone, methylprednisolone, prednisolone, prednisone, or triamcinolone, or a combination thereof.

7. The method of claim 6, wherein the glucocorticoid is hydrocortisone.

8. The method of claim 1, wherein the subject is an adolescent.

9. The method of claim 1, wherein the subject is at least 18 years old.

10. The method of claim 1, wherein the small molecule $CRF_1$ antagonist is administered at a dose of about 10 mg/day to about 400 mg/day to the subject.

11. The method of claim 10, wherein the small molecule $CRF_1$ antagonist is administered at a dose of about 50 mg.

12. The method of claim 10, wherein the small molecule $CRF_1$ antagonist is administered at a dose of about 100 mg.

13. The method of claim 10, wherein the small molecule $CRF_1$ antagonist is administered at a dose of about 200 mg.

14. The method of claim 1, wherein the small molecule $CRF_1$ antagonist is administered at a dose of about 400 mg.

15. The method of claim 1, wherein the small molecule $CRF_1$ antagonist is administered orally.

16. The method of claim 1, wherein the small molecule $CRF_1$ antagonist is formulated as a capsule or tablet.

17. The method of claim 1, wherein the small molecule $CRF_1$ antagonist is administered less than about 6 hours before sleep.

18. The method of claim 1, wherein the small molecule $CRF_1$ antagonist is administered less than about 3 hours before sleep.

19. The method of claim 1, wherein the small molecule $CRF_1$ antagonist is administered in the evening.

* * * * *